US012071621B2

(12) United States Patent
Darimont et al.

(10) Patent No.: US 12,071,621 B2
(45) Date of Patent: Aug. 27, 2024

(54) ANTI-TRANSFERRIN RECEPTOR ANTIBODY-PMO CONJUGATES FOR INDUCING DMD EXON 44 SKIPPING

(71) Applicant: Avidity Biosciences, Inc., San Diego, CA (US)

(72) Inventors: Beatrice Diana Darimont, San Diego, CA (US); Usue Etxaniz Irigoien, San Diego, CA (US); Venkata Ramana Doppalapudi, San Diego, CA (US); Michael Caramian Cochran, La Jolla, CA (US); Isaac Marks, San Diego, CA (US); Tyler Albin, San Diego, CA (US)

(73) Assignee: AVIDITY BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 18/130,757

(22) Filed: Apr. 4, 2023

(65) Prior Publication Data
US 2023/0364256 A1 Nov. 16, 2023

Related U.S. Application Data

(60) Provisional application No. 63/327,725, filed on Apr. 5, 2022.

(51) Int. Cl.
| | | |
|---|---|---|
| *C07K 16/28* | (2006.01) | |
| *A61K 31/7125* | (2006.01) | |
| *A61K 39/395* | (2006.01) | |
| *A61K 47/68* | (2017.01) | |
| *A61P 21/00* | (2006.01) | |
| *C07K 19/00* | (2006.01) | |
| *C12N 15/113* | (2010.01) | |
| *A61K 39/00* | (2006.01) | |

(52) U.S. Cl.
CPC ........ *C12N 15/113* (2013.01); *A61K 31/7125* (2013.01); *A61K 39/3955* (2013.01); *A61K 47/6807* (2017.08); *A61K 47/6849* (2017.08); *A61P 21/00* (2018.01); *C07K 16/2881* (2013.01); *C07K 19/00* (2013.01); *A61K 2039/505* (2013.01); *A61K 47/68* (2017.08); *A61K 47/6811* (2017.08); *C12N 2310/314* (2013.01); *C12N 2310/3233* (2013.01); *C12N 2320/33* (2013.01)

(58) Field of Classification Search
CPC .. C07K 16/2881; C07K 19/00; C12N 15/113; C12N 2310/314; C12N 2310/3233; A61K 39/3955; A61K 47/6807; A61K 47/6849; A61P 21/00
See application file for complete search history.

(56) References Cited

U.S. PATENT DOCUMENTS

| | | |
|---|---|---|
| 5,142,047 A | 8/1992 | Summerton et al. |
| 5,185,444 A | 2/1993 | Summerton et al. |
| 5,334,711 A | 8/1994 | Sproat et al. |
| 5,627,053 A | 5/1997 | Usman et al. |
| 5,716,824 A | 2/1998 | Beigelman et al. |
| 5,736,557 A | 4/1998 | Hofheinz et al. |
| 5,889,136 A | 3/1999 | Scaringe et al. |
| 6,008,400 A | 12/1999 | Scaringe et al. |
| 6,111,086 A | 8/2000 | Scaringe |
| 6,194,551 B1 | 2/2001 | Idusogie et al. |
| 6,528,624 B1 | 3/2003 | Idusogie et al. |
| 6,538,124 B1 | 3/2003 | Idusogie et al. |
| 6,821,783 B1 | 11/2004 | Comely et al. |
| 6,884,869 B2 | 4/2005 | Senter et al. |
| 7,364,731 B2 | 4/2008 | Idusogie et al. |
| 7,452,987 B2 | 11/2008 | Giese et al. |
| 7,498,298 B2 | 3/2009 | Doronina et al. |
| 7,833,992 B2 | 11/2010 | Vargeese et al. |
| 7,893,245 B2 | 2/2011 | Giese et al. |
| 7,923,547 B2 | 4/2011 | McSwiggen et al. |
| 7,943,762 B2 | 5/2011 | Weller et al. |
| 8,084,582 B2 | 12/2011 | Dahiyat et al. |
| 8,084,598 B1 | 12/2011 | Bentwich |
| 8,090,542 B2 | 1/2012 | Khvorova et al. |
| 8,202,979 B2 | 6/2012 | McSwiggen et al. |
| 8,273,866 B2 | 9/2012 | McSwiggen et al. |

(Continued)

FOREIGN PATENT DOCUMENTS

| | | |
|---|---|---|
| CN | 106459955 A | 2/2017 |
| EP | 0336675 A1 | 10/1989 |

(Continued)

OTHER PUBLICATIONS

Aartsma-Rus et al. Guidelines for antisense oligonucleotide design and insight into splice-modulating mechanisms. Mol Ther 17(3):548-53 (2009).
Aartsma-Rus et al. Targeted exon skipping as a potential gene correction therapy for Duchenne muscular dystrophy. Neuromuscul Disord. 12 Suppl 1:S71-7 (2002).
Abramova et al. Novel oligonucleotide analogues based on morpholino nucleoside subunits-antisense technologies: new chemical possibilities. Indian Journal of Chemistry 48B:1721-1726 (2009).
Agarwal et al. A Pictet-Spengler ligation for protein chemical modification. PNAS 110(1):46-51 (2013).

(Continued)

*Primary Examiner* — Zachary C Howard
(74) *Attorney, Agent, or Firm* — WILSON SONSINI GOODRICH & ROSATI

(57) ABSTRACT

Disclosed herein are antibody oligonucleotide conjugates and pharmaceutical compositions that induce an alteration in an incorrectly spliced dystrophin mRNA transcript to induce exon 44 skipping. Also described herein include methods for treating muscle dystrophy including Duchenne muscular dystrophy that comprises administering antibody oligonucleotide conjugates or a pharmaceutical composition that induces alteration in an incorrectly spliced dystrophin mRNA transcript to induce exon 44 skipping.

21 Claims, 11 Drawing Sheets

Specification includes a Sequence Listing.

(56) References Cited

U.S. PATENT DOCUMENTS

| | | |
|---|---|---|
| 8,288,352 B2 | 10/2012 | Doronina et al. |
| 8,324,370 B2 | 12/2012 | Giese et al. |
| 8,324,371 B2 | 12/2012 | Popplewell et al. |
| 8,361,979 B2 | 1/2013 | Aartsma-Rus et al. |
| 8,461,325 B2 | 6/2013 | Popplewell et al. |
| 8,501,703 B2 | 8/2013 | Bennett et al. |
| 8,501,930 B2 | 8/2013 | Rozema et al. |
| 8,609,105 B2 | 12/2013 | Senter et al. |
| 8,618,277 B2 | 12/2013 | Beigelman et al. |
| 8,648,185 B2 | 2/2014 | McSwigen et al. |
| 8,697,688 B2 | 4/2014 | Howard et al. |
| 8,895,722 B2 | 11/2014 | Iversen et al. |
| 8,933,215 B2 | 1/2015 | Giese et al. |
| 8,936,910 B2 | 1/2015 | Mitsch et al. |
| 8,969,526 B2 | 3/2015 | Baehner et al. |
| 9,078,911 B2 | 7/2015 | Lu |
| 9,089,614 B2 | 7/2015 | Lin et al. |
| 9,096,877 B2 | 8/2015 | Johnson et al. |
| 9,139,828 B2 | 9/2015 | Platenburg et al. |
| 9,175,286 B2 | 11/2015 | Wilton et al. |
| 9,181,551 B2 | 11/2015 | McSwiggen et al. |
| 9,222,092 B2 | 12/2015 | Giese et al. |
| 9,228,187 B2 | 1/2016 | Wilton et al. |
| 9,243,251 B2 | 1/2016 | Popplewell et al. |
| 9,243,252 B2 | 1/2016 | Popplewell et al. |
| 9,249,416 B2 | 2/2016 | Wilton et al. |
| 9,260,471 B2 | 2/2016 | Cancilla et al. |
| 9,416,361 B2 | 8/2016 | Iversen et al. |
| 9,434,948 B2 | 9/2016 | Sazani et al. |
| 9,441,229 B2 | 9/2016 | Wilton et al. |
| 9,447,415 B2 | 9/2016 | Wilton et al. |
| 9,447,417 B2 | 9/2016 | Sazani et al. |
| 9,499,818 B2 | 11/2016 | Van |
| 9,528,109 B2 | 12/2016 | De Kimpe et al. |
| 9,605,019 B2 | 3/2017 | Verdine et al. |
| 9,657,294 B2 | 5/2017 | Beigelman et al. |
| 9,695,211 B2 | 7/2017 | Wada et al. |
| 9,695,423 B2 | 7/2017 | Giese et al. |
| 9,732,344 B2 | 8/2017 | Beigelman et al. |
| 9,765,338 B2 | 9/2017 | Bennett et al. |
| 9,771,588 B2 | 9/2017 | McSwiggen et al. |
| 9,796,974 B2 | 10/2017 | Rajeev et al. |
| 9,890,379 B2 | 2/2018 | De Kimpe et al. |
| 9,926,557 B2 | 3/2018 | De Kimpe et al. |
| 9,982,257 B2 | 5/2018 | Butler et al. |
| 10,000,754 B2 | 6/2018 | Beigelman et al. |
| 10,913,800 B2 | 2/2021 | Darimont et al. |
| 10,994,020 B2 | 5/2021 | Levin et al. |
| 11,028,179 B2 | 6/2021 | Darimont et al. |
| 11,179,472 B2 | 11/2021 | Levin et al. |
| 11,311,627 B1 | 4/2022 | Levin et al. |
| 11,400,163 B2 | 8/2022 | Levin et al. |
| 2002/0142980 A1 | 10/2002 | Thompson et al. |
| 2008/0311557 A1 | 12/2008 | Elsemore et al. |
| 2011/0081362 A1 | 4/2011 | Elledge et al. |
| 2011/0263686 A1 | 10/2011 | Wilton et al. |
| 2011/0294753 A1 | 12/2011 | De Kimpe et al. |
| 2011/0301218 A1 | 12/2011 | Bozzoni et al. |
| 2012/0065169 A1 | 3/2012 | Hanson et al. |
| 2012/0094299 A1 | 4/2012 | Ranum et al. |
| 2012/0172415 A1 | 7/2012 | Voit et al. |
| 2012/0270925 A1 | 10/2012 | Wilton et al. |
| 2013/0028919 A1 | 1/2013 | Howard et al. |
| 2013/0172238 A1 | 7/2013 | Mitsch et al. |
| 2013/0309256 A1 | 11/2013 | Lyon et al. |
| 2014/0127239 A1 | 5/2014 | Howard |
| 2014/0286970 A1 | 9/2014 | Jeffrey et al. |
| 2014/0294851 A1 | 10/2014 | Nguyen |
| 2014/0296321 A1 | 10/2014 | Iversen |
| 2014/0315862 A1 | 10/2014 | Kaye |
| 2015/0037360 A1 | 2/2015 | Smith |
| 2015/0105539 A1 | 4/2015 | Miao et al. |
| 2015/0105540 A1 | 4/2015 | Miao et al. |
| 2016/0002637 A1 | 1/2016 | Sazani et al. |
| 2016/0053262 A1 | 2/2016 | Platenburg et al. |
| 2016/0102135 A1 | 4/2016 | Escobar-Cabrera |
| 2016/0298111 A1 | 10/2016 | Bestwick et al. |
| 2016/0304864 A1 | 10/2016 | De Kimpe et al. |
| 2016/0304877 A1 | 10/2016 | Swayze et al. |
| 2016/0367687 A1 | 12/2016 | Manoharan et al. |
| 2017/0107512 A1 | 4/2017 | De Kimpe et al. |
| 2017/0204410 A1 | 7/2017 | Watanabe et al. |
| 2017/0204414 A1 | 7/2017 | Van Deutekom et al. |
| 2017/0342416 A1 | 11/2017 | McSwiggen et al. |
| 2018/0016574 A1 | 1/2018 | Bestwick et al. |
| 2018/0044675 A1 | 2/2018 | Watanabe et al. |
| 2018/0112214 A1 | 4/2018 | De Kimpe et al. |
| 2018/0127758 A1 | 5/2018 | Bennett |
| 2018/0163209 A1 | 6/2018 | Bennett et al. |
| 2018/0305689 A1 | 10/2018 | Sætrom et al. |
| 2019/0240346 A1 | 8/2019 | Sugo et al. |
| 2020/0028074 A1 | 1/2020 | Defferriere et al. |
| 2020/0282074 A1 | 9/2020 | Levin et al. |
| 2021/0395742 A1 | 12/2021 | MacPherson |
| 2022/0313833 A1 | 10/2022 | Levin et al. |
| 2023/0201363 A1 | 6/2023 | Geall et al. |

FOREIGN PATENT DOCUMENTS

| | | |
|---|---|---|
| EP | 0334656 B1 | 3/1994 |
| EP | 1579015 A2 | 9/2005 |
| EP | 1068241 B1 | 10/2007 |
| EP | 2119783 A1 | 11/2009 |
| EP | 2049664 B1 | 9/2011 |
| EP | 2278004 B1 | 10/2012 |
| EP | 2344637 B1 | 12/2014 |
| EP | 1423406 B2 | 11/2015 |
| EP | 3031920 A1 | 6/2016 |
| EP | 2421971 B1 | 7/2016 |
| EP | 2287306 B2 | 10/2016 |
| EP | 3030658 A4 | 3/2017 |
| EP | 2287305 B2 | 11/2017 |
| EP | 2486141 B1 | 1/2018 |
| EP | 2902406 B1 | 1/2018 |
| EP | 2595664 B1 | 10/2018 |
| WO | WO-9104753 A1 | 4/1991 |
| WO | WO-9207065 A1 | 4/1992 |
| WO | WO-9315187 A1 | 8/1993 |
| WO | WO-9726270 A2 | 7/1997 |
| WO | WO-9734631 A1 | 9/1997 |
| WO | WO-9813526 A1 | 4/1998 |
| WO | WO-0149698 A1 | 7/2001 |
| WO | WO-2006000057 A1 | 1/2006 |
| WO | WO-2008036127 A2 | 3/2008 |
| WO | WO-2009026933 A1 | 3/2009 |
| WO | WO-2009054725 A2 | 4/2009 |
| WO | WO-2009099942 A2 | 8/2009 |
| WO | WO-2009099991 A2 | 8/2009 |
| WO | WO-2009144481 A2 | 12/2009 |
| WO | WO-2010048586 A1 | 4/2010 |
| WO | WO-2011130371 A1 | 10/2011 |
| WO | WO-2011150408 A2 | 12/2011 |
| WO | WO-2014080251 A1 | 5/2014 |
| WO | WO-2014140317 A2 | 9/2014 |
| WO | WO-2014144978 A2 | 9/2014 |
| WO | WO-2014145090 A1 | 9/2014 |
| WO | WO-2014177042 A1 | 11/2014 |
| WO | WO-2014197854 A1 | 12/2014 |
| WO | WO-2015021457 A2 | 2/2015 |
| WO | WO-2015038426 A1 | 3/2015 |
| WO | WO-2015057699 A2 | 4/2015 |
| WO | WO-2016187425 A1 | 11/2016 |
| WO | WO-2016207240 A1 | 12/2016 |
| WO | WO-2017148879 A1 | 9/2017 |
| WO | WO-2017173408 A1 | 10/2017 |
| WO | WO-2017192679 A1 | 11/2017 |
| WO | WO-2017221883 A1 | 12/2017 |
| WO | WO-2018002812 A1 | 1/2018 |
| WO | WO-2018129384 A1 | 7/2018 |
| WO | WO-2019060775 A1 | 3/2019 |
| WO | WO-2021142313 A1 * | 7/2021 ......... A61K 47/6807 |

(56) References Cited

FOREIGN PATENT DOCUMENTS

| WO | WO-2023283615 A1 | 1/2023 |
|---|---|---|
| WO | WO-2023196400 A2 | 10/2023 |

OTHER PUBLICATIONS

Alegre et al. Effect of a Single Amino Acid Mutation on the Activating and Immunosuppressive Properties of a "Humanized" OKT3 Monoclonal Antibody. J Immunol 148:3461-3468 (1992).
Arechavala-Gomeza et al. Comparative analysis of antisense oligonucleotide sequences for targeted skipping of exon 51 during dystrophin pre-mRNA splicing in human muscle. Hum Gene Ther. 18(9):798-810 (2007).
Axup et al. Synthesis of site-specific antibody-drug conjugates using unnatural amino acids. PNAS 109(40):16101-16106 (2012).
Beduneau et al. Design of targeted lipid nanocapsules by conjugation of whole antibodies and antibody Fab' fragments. Biomaterials 28(33):4978-4990 (2007).
Beigelman et al. Chemical modification of hammerhead ribozymes. Catalytic activity and nuclease resistance. J Biol Chem 270:25702-25708 (1995).
Bell et al. Epidermal Growth Factor Receptor Mutations and Gene Amplification in Non-Small-Cell Lung Cancer: Molecular Analysis of the IDEAL/INTACT Gefitinib Trials. J Clin Oncol 23(31):8081-8092 (2005).
Bird et al. Single-chain antigen-binding proteins. Science 242:423-442 (1988).
Blaney et al. Traceless solid-phase organic synthesis. Chem. Rev. 102:2607-2024 (2002.
Brain and Development 42:117-123 (2010).
Burlina et al. Chemical engineering of RNase resistant and catalytically active hammerhead ribozymes. Bioorg Med Chem 5:1999-2010 (1997).
Casi et al. Site-specific traceless coupling of potent cytotoxic drugs to recombinant antibodies for pharmacodelivery. J Am Chem Soc 134(13):5887-5892 (2012).
Clackson et al. Making antibody fragments using phage display libraries. Nature 352(6336):624-628 (1991).
Colberre-Garapin et al. A new dominant hybrid selective marker for higher eukaryotic cells. J Mol Biol 150:1-14 (1981).
Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).
Crouse et al. Expression and amplification of engineered mouse dihydrofolate reductase minigenes. Mol Cell Biol 3(2):257-266 (1983).
Darimont et al. 8-05 Abstract: A novel Antibody-Oligonucleotide Conjugate (AOC) platform enables efficient regulation of muscle targets in mice. Journal of Cachexia, Sarcopenia and Muscle 8:999-1080 (2017).
Dawson et al. Modulation of Reactivity in Native Chemical Ligation through the Use of Thiol Additives. J. Am. Chem. Soc. 119:4325-4329 (1997).
Dawson et al. Synthesis of proteins by native chemical ligation. Science 266(5186):776-779 (1994).
De Angelis et al. Chimeric snRNA molecules carrying antisense sequences against the splice junctions of exon 51 of the dystrophin pre-mRNA induce exon skipping and restoration of a dystrophin synthesis in Delta 48-50 DMD cells. PNAS USA 99:9456-9461 (2002).
Debinski et al. Monovalent immunotoxin containing truncated form of Pseudomonas exotoxin as potent antitumor agent. Cancer Research 52(19):5379-5385 (1992).
Den Dunnen et al. Topography of the Duchenne muscular dystrophy (DMD) gene: FIGE and cDNA analysis of 194 cases reveals 115 deletions and 13 duplications. Am J Hum Genet. 45(6):835-847 (1989).
Domingo et al. Transferrin receptor as a target for antibody-drug conjugates. Methods in Enzymology 112:238-247 (1985).
Earnshaw et al. Modified oligoribonucleotides as site-specific probes of RNA structure and function. Biopolymers (Nucleic Acid Sciences) 48:39-55 (1998).
Echigoya et al. In Silico Screening Based on Predictive Algorithms as a Design Tool for Exon Skipping Oligonucleotides in Duchenne Muscular Dystrophy. PLoS One 10(3):e0120058 (2015).
Feener et al. Alternative splicing of human dystrophin mRNA generates isoforms at the carboxy terminus. Nature 338:509-511 (Apr. 6, 1989).
Gao et al. Effective Dystrophin Restoration by a Novel Muscle-Homing Peptide-Morpholino Conjugate in Dystrophin-Deficient mdx Mice. Mol Ther. 22(7):1333-1341 (2014).
Goldspiel et al. Human gene therapy. Clin Pharm 12:488-505 (1993).
Gooding et al. Oligonucleotide conjugates—Candidates for gene silencing therapeutics. Eur J Pharm Biopharm. 107:321-40 (2016).
Griffey et al. 2'-0-aminopropyl ribonucleotides: a zwitterionic modification that enhances the exonuclease resistance and biological activity of antisense oligonucleotides, J. Med. Chem. 39(26):5100-5109 (1997).
Hackeng et al. Protein synthesis by native chemical ligation: Expanded scope by using straightforward methodology. PNAS USA 96:10068-10073 (1999).
Hanes et al. In vitro selection and evolution of functional proteins by using ribosome display. PNAS USA 94:4937-4942 (1997).
Hejesen et al. A traceless aryl-triazene linker for DNA-directed chemistry. Org Biomol Chem 11(15):2493-2497 (2013).
Hoffman et al. Restoring Dystrophin Expression in Duchenne Muscular Dystrophy Muscle: Progress in Exon Skipping and Stop Codon Read Through. Am J Pathol 179(1):12-22 (2011).
Hudson et al. Cellular delivery of hammerhead ribozymes conjugated to a transferrin receptor antibody. Int J Pharmaceuticals 182(1):49-58 (1999).
Huse et al. Generation of a large combinatorial library of the immunoglobulin repertoire in phage lambda. Science 246(4935):1275-1281 (1989).
Huston et al. Protein engineering of antibody binding sites: recovery of specific activity in an anti-digoxin single-chain Fv analogue produced in *Escherichia coli*. PNAS USA 85:5879-5883 (1988).
Idusogie et al., Engineered Antibodies with Increased Activity to Recruit Complement. J Immunol. 166(4):2571-5 (2001).
Ishikawa et al. Preparation of monomeric Fab'-horseradish peroxidase conjugate using thiol groups in the hinge and its evaluation in enzyme immunoassay and immunohistochemical staining. Ann N Y Acad Sci. 420:74-89 (1983).
Jearawiriyapaisarn et al. Sustained Dystrophin Expression Induced by Peptide-conjugated Morpholino Oligomers in the Muscles of mdx Mice. Mol Ther. 16(9): 1624-1629 (2008).
Kaneko et al. Optimizing Therapeutic Antibody Function: Progress With Fc Domain Engineering. Biodrugs 25(1):1-11 (2011).
Karpeisky et al. Highly efficient synthesis of 2'-O-amino nucleosides and their incorporation in hammerhead ribozymes. Tetrahedron Lett 39:1131-1134 (1998).
Kohler et al. Continuous cultures of fused cells secreting antibody of predefined specificity. Nature 256:495-497 (1975).
Koizumi. ENA oligonucleotides as therapeutics. Curr Opin Mol Ther 8(2):144-149 (2006).
Kozbor et al. The production of monoclonal antibodies from human lymphocytes. Immunology Today 4:72-79 (1983).
Kutmeier et al. Assembly of humanized antibody genes from synthetic oligonucleotides using a single-round PCR. BioTechniques 17:242 (1994).
Lazar et al. Engineered antibody Fc variants with enhanced effector function. PNAS USA 103(11):4005-10 (2006).
Lee et al. Antisense PMO cocktails effectively skip dystrophin exons 45-55 in myotubes transdifferentiated from DMD patient fibroblasts. PLoS One 13(5):e0197084 (2018).
Levin. Targeting Therapeutic Oligonucleotides. N Engl J Med 376:86-88 (2017).
Loakes. Survey and summary: The applications of universal DNA base analogues. Nucleic Acids Research 29:2437-2447 (2001).

(56) References Cited

OTHER PUBLICATIONS

Lowy et al., Isolation of transforming DNA: Cloning the hamster aprt gene. Cell 22:817-823 (1980).
Lyon et al. Self-hydrolyzing maleimides improve the stability and pharmacological properties of antibody-drug conjugates. Nat. Biotechnol. 32(10):1059-1062 (2014).
Martinez et al. Single-stranded antisense siRNAs guide target RNA cleavage in RNAi. Cell 110(5):563-574 (2002).
Miyata et al. Polymer nanotechnology for nucleic acid delivery. Drug Delivery System 31(1):44-53 (2016) (English Abstract).
Moore et al. Engineered Fc variant antibodies with enhanced ability to recruit complement and mediate effector functions. mAbs 2(2):181-189 (2010).
Morgan et al. Human gene therapy. Ann Rev Biochem 62:191-217 (1993).
Morrison et al. Chimeric human antibody molecules: mouse antigen-binding domains with human constant region domains. PNAS USA 81(21):6851-6855 (1984).
Mulligan et al. Selection for animal cells that express the *Escherichia coli* gene coding for xanthine-guanine phosphoribosyltransferase. PNAS USA 78(4):2072-2076 (1981).
Mulligan. The basic science of gene therapy. Science. 260(5110):926-932 (1993).
Natsume et al. Engineered Antibodies of IgG1/IgG3 Mixed Isotype With Enhanced Cytotoxic Activities. Cancer Res 68(10):3863-72 (2008).
Neuberger et al. Recombinant antibodies possessing novel effector functions. Nature 312(5995):604-608 (1984).
Normand-Sdiqui et al. Oligonucleotide delivery: Uptake of rat transferrin receptor antibody (OX / 26) conjugates into an in vitro immortalised cell line model of the blood, brain barrier. Int J Pharmaceuticals 163:63-71 (1998).
Obika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
O'Hare et al. Transformation of mouse fibroblasts to methotrexate resistance by a recombinant plasmid expressing a prokaryotic dihydrofolate reductase. PNAS USA 78:1527-1531 (1981).
PCT/US2018/012672 International Search Report and Written Opinion dated May 24, 2018.
PCT/US2018/012672 Invitation to Pay Additional Fees dated Mar. 20, 2018.
PCT/US2018/052289 International Search Report and Written Opinion dated Jan. 11, 2019.
Perrault et al. Mixed deoxyribo- and ribo-oligonucleotides with catalytic activity. Nature 344:565-568 (1990).
Pieken et al. Kinetic characterization of ribonuclease-resistant 2'-modified hammerhead ribozymes. Science 253:314-317 (1991).
Santerre et al. Expression of prokaryotic genes for hygromycin B and G418 resistance as dominant-selection markers in mouse L cells. Gene 30(1-3):147-156 (1984).
Schnyder et al. Targeting of skeletal muscle in vitro using biotinylated immunoliposomes. Biochem J 377(Pt.1):61-67 (2004).
Schwarz et al. Evidence that siRNAs function as guides, not primers, in the *Drosophila* and human RNAi pathways. Molecular Cell 10:537-548 (2002).
Sekyere et al. Examination of the distribution of the transferrin homologue, melanotransferrin (tumour antigen p97), in mouse and human. Biochimica et Biophysica Acta 1722(2):131-142 (2005).
Shields et al. High Resolution Mapping of the Binding Site on Human IgG1 for $F_{c\gamma}RI$, $F_{c\gamma}RII$, $F_{c\gamma}RIII$, and FcRn and Design of IgG1 Variants with Improved Binding to the $F_{c\gamma}R$. J Biol Chem 276(9):6591-6604 (2001).
Singh et al. Recent developments in oligonucleotide conjugation. Chem Soc Rev 39(6):2054-2070 (2010).
Skerra et al. Assembly of a functional Immunoglobulin Fv fragment in *Escherichia coli*. Science 240(4855):1038-1041 (1988).
Stavenhagen et al. Enhancing the potency of therapeutic monoclonal antibodies via Fc optimization. Adv Enzyme Regul. 48:152-64 (2008).
Stavenhagen et al. Fc Optimization of Therapeutic Antibodies Enhances Their Ability to Kill Tumor Cells In vitro and Controls Tumor Expansion In vivo via Low-Affinity Activating Fcγ Receptors. Cancer Res 67(18):8882-91 (2007).
Strop et al. Location matters: site of conjugation modulates stability and pharmacokinetics of antibody drug conjugates. Chem Biol 20(2):161-167 (2013).
Sugo et al. Development of antibody-siRNA conjugate targeted to cardiac and skeletal muscles. J Control release 237:1-13 (2016).
Summerton, et al. Morpholino antisense oligomers: design, preparation, and properties. Antisense Nucleic Acid Drug Dev. Jun. 1997;7(3):187-95.
Suñé-Pou et al. Targeting Splicing in the Treatment of Human Disease. Genes 8:E87 (2017).
Szybalska et al. Genetics of human cell line. IV. DNA-mediated heritable transformation of a biochemical trait. PNAS USA 48:2026-2034 (1962).
Takeda et al. Construction of chimaeric processed immunoglobulin genes containing mouse variable and human constant region sequences. Nature 314(6010):452-454 (1985).
Tolstoshev. Gene Therapy, Concepts, Current Trials and Future Directions. Ann. Rev. Pharmacol. Toxicol. 32:573-596 (1993).
U.S. Appl. No. 16/128,450 Miscellaneous Communication re: Third Party Submission dated Jul. 1, 2019.
U.S. Appl. No. 16/128,450 Office Action dated Apr. 19, 2019.
U.S. Appl. No. 16/128,450 Office Action dated Apr. 30, 2020.
U.S. Appl. No. 16/128,450 Office Action dated Dec. 16, 2020.
U.S. Appl. No. 16/128,450 Office Action dated Sep. 19, 2019.
U.S. Appl. No. 16/129,696 Miscellaneous Communication re: Third Party Submission dated Jul. 3, 2019.
U.S. Appl. No. 16/129,696 Office Action dated Apr. 13, 2020.
U.S. Appl. No. 16/129,696 Office Action dated Apr. 17, 2019.
U.S. Appl. No. 16/129,696 Office Action dated Dec. 14, 2020.
U.S. Appl. No. 16/129,696 Office Action dated May 26, 2021.
U.S. Appl. No. 16/129,696 Office Action dated Sep. 19, 2019.
U.S. Appl. No. 16/649,572 Miscellaneous Communication re: Third Party Submission dated Mar. 19, 2021.
U.S. Appl. No. 16/649,572 Office Action dated Feb. 22, 2023.
U.S. Appl. No. 17/463,473 Office Action dated Dec. 13, 2021.
U.S. Appl. No. 17/463,484 Office Action dated Jan. 4, 2022.
Usman et al. Exploiting the chemical synthesis of RNA. Trends Biochem Sci 17:334-339 (1992).
Van Deutekom et al. Antisense-induced exon skipping restores dystrophin expression in DMD patient derived muscle cells. Hum Mol Genet. 10(15):1547-54 (2001).
Van Vliet et al. Assessment of the feasibility of exon 45-55 multiexon skipping for duchenne muscular dystrophy. BMC Medical Genetics 9:105 (2008).
Verma et al. Modified oligonucleotides: synthesis and strategy for users. Annu Rev Biochem 67:99-134 (1998).
Walker et al. Improved cellular delivery of antisense oligonucleotides using transferrin receptor antibody-oligonucleotide conjugates. Pharmaceutical research 12(10):1548-1553 (1995).
Ward et al. Binding activities of a repertoire of single immunoglobulin variable domains secreted from *Escherichia coli*. Nature 341(6242):544-546 (1989).
Wigler et al. Transfer of purified herpes virus thymidine kinase gene to cultured mouse cells. Cell 11:223-232 (1977).
Wigler et al. Transformation of mammalian cells with an amplifiable dominant-acting gene. PNAS USA 77:3567-3570 (1980).
Wu et al. Building complex glycopeptides: Development of a cysteine-free native chemical ligation protocol. Angew. Chem. Int. Ed. 45:4116-4125 (2006).
Wu et al. Cell-penetrating peptides as transporters for morpholino oligomers: effects of amino acid composition on intracellular delivery and cytotoxicity. Nucleic Acids Res 35(15):5182-5191 (2007).
Wu et al. Delivery systems for gene therapy. Biotherapy 3:87-95 (1991).
Wu et al. Site-specific chemical modification of recombinant proteins produced in mammalian cells by using the genetically encoded aldehyde tag. PNAS USA 106(9):3000-3005 (2009).
Xia et al. Intravenous siRNA of brain cancer with receptor targeting and avidin-biotin technology. Pharm Res 24(12):2309-16 (2007).

(56) References Cited

OTHER PUBLICATIONS

PCT/US2023/017574 International Invitation to Pay Additional Fees dated Aug. 25, 2023.
PCT/US2023/017574 International Search Report and Written Opinion dated Oct. 31, 2023.
Rhodes et al. Bicyclic Peptides as Next-Generation Therapeutics. Chemistry 23(52):12690-12703 (2017).
U.S. Appl. No. 16/649,572 Office Action dated Aug. 31, 2023.
Meregalli et al. Duchenne muscular dystrophy caused by a frame-shift mutation in the acceptor splice site of intron 26. BMC Med Genet 17(1):55 (2016).
U.S. Appl. No. 16/649,572 Office Action dated Apr. 16, 2024.
U.S. Appl. No. 17/843,705 Office Action dated Feb. 9, 2024.

* cited by examiner

ANTI-TRANSFERRIN RECEPTOR ANTIBODY-PMO CONJUGATES FOR INDUCING DMD EXON 44 SKIPPING

CROSS-REFERENCE

This application claims the benefit of U.S. Provisional Application No. 63/327,725 filed Apr. 5, 2022, which is incorporated herein by reference in its entirety.

SEQUENCE LISTING

The instant application contains a Sequence Listing which has been submitted electronically in XML format and is hereby incorporated by reference in its entirety. Said XML copy, created on Jul. 28, 2023, is named 45532-762_201_SL.xml and is 109,244 bytes in size.

BACKGROUND OF THE DISCLOSURE

Duchenne Muscular Dystrophy (DMD) is a rare X-linked neuromuscular disease that manifests primarily in boys, affecting about 1:5000-10,000 males born worldwide. There are about 300,000 DMD patients worldwide. DMD is a monogenic disease; it is progressive, severe and irreversible. The disease is caused by mutations in the DMD gene, the longest gene in the human genome (79 exons), which encodes for the dystrophin protein (430 kDa). The central domain of dystrophin, called rod domain, is formed by 24 spectrin repeats that function as a shock-absorber and protect the sarcolemma from damage during movement.

DMD is caused by mutations (changes) within the dystrophin gene. Deletions of one or more exons are the most common type of mutation. Since there are a total of 79 exons in the dystrophin gene, there are many different deletions that can occur. However, there are certain areas of the gene that are more likely to have a deletion, and these areas are called "hot spots". The deletions in the DMD gene that are non-randomly distributed with many of the large gene deletions that occur in the DMD gene can be detected in specific hotspot areas of the gene. These hotspots are clustered within two main regions: about 20% of the deletions occur at the 5' proximal portion of the gene (exons 1, 3, 4, 5, 8, 13, 19); and about 80% of the deletions occur at the mid-distal region i.e. 42-45, 47, 48, 50-53 (Den Dunnen et al. Am J Hum Genet. 1989; 45(6):835-847). The mutated DMD gene fails to produce any functional dystrophin and lack of functional dystrophin results in progressive muscle weakness due to muscle injury, repair, inflammation changes and paralysis.

Current research for DMD therapy includes stem cell replacement therapy, analog up-regulation, gene replacement, and exon-skipping technology. Exon-skipping technology uses structural analogs of DNA called antisense oligonucleotides to help cells skip over a specific exon during RNA splicing. These antisense oligonucleotides allow faulty parts of the dystrophin gene to be skipped over when it is transcribed to RNA for protein production, permitting a still-truncated but more functional version of the dystrophin protein to be produced by the muscle cells.

There are several antisense oligonucleotides that have already been approved for DMD patients with amenable to exon 45, 51, or 53 skipping. The antisense oligonucleotide named Eteplirsen has been approved in the United States for the treatment of mutations amenable to dystrophin exon 51 skipping. The antisense oligonucleotide named Golodirsen was approved for medical use in the United States in 2019, for the treatment of cases that can benefit from skipping exon 53 of the dystrophin transcript. The antisense oligonucleotide named Casimersen was approved for treatment in the United States in February 2021 for patients who have a confirmed mutation of the DMD gene that is amenable to exon 45 skipping.

Despite extensive research using exon skipping for exon 44 (U.S. Pat. Nos. 9,447,417, 8,461,325, and 8,361,979), there is currently no FDA approved exon skipping therapy for DMD patients amenable to exon 44 skipping. Approximately 6% of the DMD patient population are amenable to exon 44 skipping and the majority of these DMD patients may also have a deletion of exon 45 of the DMD transcript.

A new class of therapeutics called antibody oligonucleotide conjugates (AOC) improves the delivery of antisense oligonucleotides. These AOCs target and deliver antisense oligonucleotides to specific tissue and cell types including muscle cells. These AOCs are being developed for the potential breakthrough therapy for DMD patients including patients that are amenable to exon 44 skipping. There is a need to provide therapy for DMD patients amenable to exon 44 skipping.

SUMMARY OF THE DISCLOSURE

Disclosed herein, in certain aspects, are phosphorodiamidate morpholino oligonucleotide (PMO) conjugates comprising an anti-transferrin receptor antibody or antigen binding fragment thereof conjugated to a PMO molecule, wherein the PMO molecule comprises a sequence selected from a group consisting of SEQ ID NOs:100-133. In some aspects, the PMO molecule hybridizes to an acceptor splice site, a donor splice site, or an exonic splice enhancer element of a pre-mRNA transcript of the DMD gene and induces exon 44 skipping in said pre-mRNA transcript to generate a mRNA transcript encoding a truncated DMD protein. In some aspects, the PMO molecule comprises at least from about 10 to about 30 nucleotides in length. In some aspects, the PMO molecule is delivered into a muscle cell. In some aspects, the PMO molecule hybridizes the exon 44 acceptor splice site of a pre-mRNA transcript of the DMD gene in said pre-mRNA transcript to generate a mRNA transcript encoding a truncated dystrophin protein. In some aspects, the anti-transferrin receptor antibody or antigen binding fragment thereof comprises a humanized antibody or antigen binding fragment thereof, chimeric antibody or antigen binding fragment thereof, monoclonal antibody or antigen binding fragment thereof, monovalent Fab', divalent Fab2, single chain variable fragment (scFv), diabody, minibody, nanobody, single domain antibody (sdAb), or camelid antibody or antigen binding fragment thereof. In some aspects, the PMO molecule is conjugated to the anti-transferrin receptor antibody or antigen binding fragment thereof via a linker. In some aspects, the linker is a cleavable linker. In some aspects, the linker is a non-cleavable linker. In some aspects, the linker is selected from the group consisting of a heterobifunctional linker, a homobifunctional linker, a maleimide group, a dipeptide moiety, a benzoic acid group or derivatives thereof, a C1-C6 alkyl group, and a combination thereof. In some aspects, the PMO conjugate has a PMO molecule to antibody ratio (DAR) of about 1:1, 2:1, 3:1, 4:1 5:1, 6:1, 7:1, 8:1 or higher. In some aspects, the PMO conjugate has an average DAR of about 1, 2, 3, 4, 5, 6, 7, 8 or higher. In some aspects, the PMO conjugate has an average DAR in the range of 3.5-4.5. In some aspects, the PMO conjugate has an average DAR in the range of 7.5-8.5. In some aspects, the PMO conjugate has an average DAR of about 4. In some aspects, the PMO conjugate has an average DAR of about 8. In some aspects, the PMO conjugate has a DAR of about 4. In some aspects, the PMO conjugate has a DAR of about 8. In some aspects, the PMO conjugate is formulated for parenteral administration. In some aspects, the truncated dystrophin proteins modulate muscular dystrophy. In some aspects, the muscular dystrophy is Duchenne muscular dystrophy or Becker muscular dystrophy.

Also disclosed herein, in certain aspects, are methods of treating muscular dystrophy in a subject in need thereof comprising administering to said subject a phosphorodiamidate morpholino oligonucleotide (PMO) conjugate comprising an anti-transferrin receptor antibody or antigen binding fragment thereof conjugated to a PMO molecule comprising a sequence selected from a group consisting of SEQ ID NOs:100-133; wherein the PMO molecule hybridizes to an acceptor splice site, a donor splice site, or an exonic splice enhancer element of a pre-mRNA transcript of the DMD gene and induces exon 44 skipping in said pre-mRNA transcript to generate a mRNA transcript encoding a truncated dystrophin protein. In some aspects, the PMO molecule is delivered into a muscle cell. In some aspects, the anti-transferrin receptor antibody or antigen binding fragment thereof comprises a humanized antibody or antigen binding fragment thereof, chimeric antibody or antigen binding fragment thereof, monoclonal antibody or antigen binding fragment thereof, monovalent Fab', divalent Fab2, single chain variable fragment (scFv), diabody, minibody, nanobody, single domain antibody (sdAb), or camelid antibody or antigen binding fragment thereof. In some aspects, the PMO molecule comprises at least from about 10 to about 30 nucleotides in length. In some aspects, the PMO molecule is conjugated to the anti-transferrin receptor antibody or antigen binding fragment thereof via a linker. In some aspects, the linker is a cleavable linker. In some instances, the linker is a non-cleavable linker. In some aspects, the linker is selected from the group consisting of a heterobifunctional linker, a homobifunctional linker, a maleimide group, a dipeptide moiety, a benzoic acid group or derivatives thereof, a C1-C6 alkyl group, and a combination thereof. In some aspects, the PMO conjugate has an average of PMO molecule to antibody ratio (DAR) of about 1:1, 2:1, 3:1, 4:1, 5:1, 6:1, 7:1, or 8:1. In some aspects, the PMO conjugate has an average DAR in the range of 3.5-4.5. In some aspects, the PMO conjugate has an average DAR in the range of 7.5-8.5. In some aspects, the PMO conjugate has an average DAR of about 4. In some aspects, the PMO conjugate has an average DAR of about 8. In some aspects, the PMO conjugate is administered parenterally. In some aspects, the truncated dystrophin proteins modulate muscular dystrophy. In some aspects, the muscular dystrophy is Duchenne muscular dystrophy or Becker muscular dystrophy.

Also disclosed herein, in certain aspects, are methods of inducing exon 44 skipping in a targeted pre-mRNA transcript of DMD gene, comprising: (a) contacting a muscle cell with a phosphorodiamidate morpholino oligonucleotide (PMO)-antibody conjugate, wherein the PMO-antibody conjugate comprises an anti-transferrin receptor antibody or antigen binding fragment thereof, and a PMO molecule targeting an acceptor splice site, a donor splice site, or an exonic splice enhancer element of the targeted pre-mRNA transcript of the DMD gene; wherein the PMO molecule induces exon 44 skipping in the targeted pre-mRNA transcript, and wherein the PMO-antibody conjugate is preferentially delivered into the muscle cell; (b) hybridizing the PMO molecule to the targeted pre-mRNA transcript to induce exon 44 skipping in the targeted pre-mRNA transcript; and (c) translating a mRNA transcript produced from the targeted pre-mRNA transcript processed in step b) in the muscle cell to generate a truncated dystrophin protein. In some aspects, the anti-transferrin receptor antibody or antigen binding fragment thereof comprises a humanized antibody or antigen binding fragment thereof, chimeric antibody or antigen binding fragment thereof, monoclonal antibody or antigen binding fragment thereof, monovalent Fab', divalent Fab2, single chain variable fragment (scFv), diabody, minibody, nanobody, single-domain antibody (sdAb), or camelid antibody or antigen binding fragment thereof. In some aspects, the PMO molecule comprises at least from about 10 to about 30 nucleotides in length. In some aspects, the PMO molecule comprises at least 90%, 95%, 99%, or 100% sequence identity to a sequence selected from a group consisting of SEQ ID NOs: 100-133. In some aspects, the PMO molecule targets the acceptor site of exon 44. In some aspects, the PMO molecule is conjugated to the anti-transferrin receptor antibody or antigen binding fragment thereof via a linker. In some aspects, the linker is a cleavable linker. In some aspects, the linker is a non-cleavable linker. In some aspects, the linker is selected from the group consisting of a heterobifunctional linker, a homobifunctional linker, a maleimide group, a dipeptide moiety, a benzoic acid group or derivatives thereof, a C1-C6 alkyl group, and a combination thereof. In some aspects, the PMO conjugate has an average of PMO to antibody ratio (DAR) of about 1:1, 2:1, 3:1, 4:1, 5:1, 6:1, 7:1, 8:1 or higher. In some aspects, the PMO conjugate has a DAR of about 1, 2, 3, 4, 5, 6, 7, 8 or higher. In some aspects, the PMO conjugate has an average DAR in the range of 3.5-4.5. In some aspects, the PMO conjugate has an average DAR in the range of 7.5-8.5. In some aspects, the PMO conjugate has an average DAR of about 4. In some aspects, the PMO conjugate has an average DAR of about 8. In some aspects, the method is an in vivo method.

Also disclosed herein, in certain aspects, are methods of inducing exon 44 skipping in a DMD subject in need thereof comprising administering to said subject a phosphorodiamidate morpholino oligonucleotide (PMO) conjugate comprising an anti-transferrin receptor antibody or antigen binding fragment thereof conjugated to a PMO molecule comprising a sequence selected from a group consisting of SEQ ID NOs:100-133; wherein the PMO molecule hybridizes to the exon 44 acceptor splice site of a pre-mRNA transcript of the DMD gene and induces exon 44 skipping in said pre-mRNA transcript to generate a mRNA transcript encoding a truncated dystrophin protein.

Also disclosed herein, in certain aspects, are methods of restoring dystrophin in a DMD subject in need thereof comprising administering to said subject a phosphorodiamidate morpholino oligonucleotide (PMO) conjugate comprising an anti-transferrin receptor antibody or antigen binding fragment thereof conjugated to a PMO molecule comprising a sequence selected from a group consisting of SEQ ID NOs:100-133; wherein the PMO molecule hybridizes to the exon 44 acceptor splice site of a pre-mRNA transcript of the DMD gene and induces exon 44 skipping in said pre-mRNA transcript to generate a mRNA transcript encoding a truncated dystrophin protein.

Also disclosed herein, in certain aspects, are methods of generating a truncated dystrophin protein in a DMD subject in need thereof comprising administering to said subject a phosphorodiamidate morpholino oligonucleotide (PMO) conjugate comprising an anti-transferrin receptor antibody or antigen binding fragment thereof conjugated to a PMO molecule comprising a sequence selected from a group consisting of SEQ ID NOs:100-133; wherein the PMO molecule hybridizes to the exon 44 acceptor splice site of a pre-mRNA transcript of the DMD gene and induces exon 44 skipping in said pre-mRNA transcript to generate a mRNA transcript encoding a truncated dystrophin protein.

BRIEF DESCRIPTION OF THE DRAWINGS

FIG. 4A is a plot of the dose response curve of the relative levels of exon 44 skipping in response to increasing concentrations of hEx44_Ac7_26 in healthy primary and immortalized cells. FIG. 4B is a plot of the dose response curve of the relative levels of exon 44 skipping in response to increasing concentrations of hEx44_Ac7_26 in DMD primary cells derived from DMD patients. FIG. 4C is a plot of the dose response curve of the relative levels of exon 44 skipping in response to increasing concentrations of hEx44_Ac7_26 in DMD immortalized cells.

FIG. 5A illustrates pictures of immunofluorescence staining of dystrophin positive fibers in healthy human cells and in DMD patient-derived cultured myotubes transfected with hEx44_Ac7_26. FIG. 5B is a plot for the dose response curve of the relative levels of dystrophin quantified by immunofluorescence staining in response to increasing concentrations of hEx44_Ac7_26 in DMD patient-derived cultured myotubes. FIG. 5C is a bar graph quantifying levels of dystrophin protein by Jess capillary assay in response to increasing concentrations of hEx44_Ac7_26 in healthy and DMD patient-derived cultured myotubes.

FIG. 6A is a plot of the dose response curve of the relative levels of exon 44 skipping in response to increasing concentrations of hEx44_Ac7_26 in in non-human primate myotubes. FIG. 6B is a bar graph quantifying the number of exon 44 skipped copies in response to increasing concentrations of hEx44_Ac7_26 in non-human primate myotubes. FIG. 6C is a bar graph quantifying the total number of dystrophin copies in the presence of increasing concentrations of hEx44_Ac7_26 in non-human primate myotubes.

DETAILED DESCRIPTION OF THE DISCLOSURE

Figure 1:
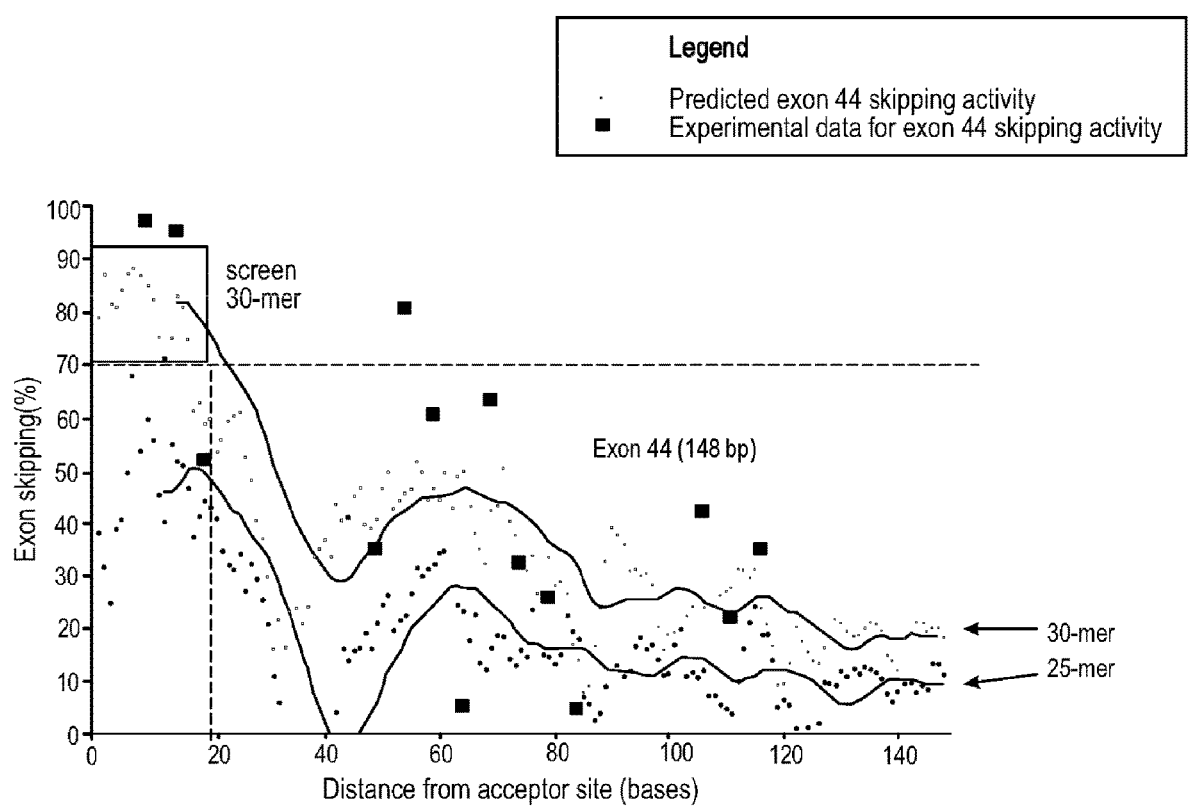
FIG. 1 is a plot comparing predicted values of exon 44 skipping activity with experimental values of exon 44 skipping in response to 25-mer and 30-mer phosphorodiamidate morpholino oligomers (PMOs).

Disclosed herein, in some aspects, are antibody-polynucleic acid conjugate compositions for the treatment of muscle dystrophy. Also disclosed herein, in some aspects, are methods of treating muscle dystrophy caused by an incorrectly spliced DMD mRNA transcript in a subject in need thereof, the method comprising: administering to the subject an antibody-polynucleic acid conjugate; wherein the antibody-polynucleic acid conjugate induces alteration in the incorrectly spliced pre-mRNA dystrophy transcript to induce exon 44 skipping of the DMD mRNA transcript to generate a fully processed DMD mRNA transcript; and wherein the fully processed DMD mRNA transcript encodes a functional and truncated dystrophin protein, thereby treating the disease or disorder in the subject. As used herein, the term "polynucleic acid" is interchangeably used with the term "oligonucleotide".

Disclosed herein, in some aspects, are antibody-antisense oligonucleotide (ASO) conjugate or antibody-Phosphorodiamidate morpholino oligomer (PMO) conjugate compositions for the treatment of muscle dystrophy. Also disclosed herein are methods of treating muscle dystrophy caused by an incorrectly spliced DMD mRNA transcript in a subject in need thereof, the method comprising: administering to the subject an antibody-ASO conjugate or an antibody-PMO conjugate; wherein the ASO or PMO induces alteration in the incorrectly spliced pre-mRNA dystrophy transcript to induce exon 44 skipping of the DMD mRNA transcript to generate a fully processed DMD mRNA transcript; and wherein the fully processed DMD mRNA transcript encodes a functional and truncated dystrophin protein, thereby treating the disease or disorder in the subject.

In some instances, one such area where antibody-polynucleic acid conjugate is used is for treating muscular dystrophy. Muscular dystrophy encompasses several diseases that affect the muscle. Duchenne muscular dystrophy is a severe form of muscular dystrophy and caused by mutations in the DMD gene. In some instances, mutations in the DMD gene disrupt the translational reading frame and results in non-functional dystrophin protein.

Described herein, in certain aspects, are methods and compositions relating to nucleic acid therapy to induce an insertion, deletion, duplication, or alteration in an incorrectly spliced mRNA transcript to induce exon skipping or exon inclusion, which is used to restore the translational reading frame. In some aspects, also described herein include methods and compositions for treating a disease or disorder characterized by an incorrectly processed mRNA transcript, in which after removal of an exon, the mRNA is capable of encoding a functional protein, thereby treating the disease or disorder. In additional aspects, described herein include pharmaceutical compositions and kits for treating the same.

RNA Processing

RNA has a central role in regulation of gene expression and cell physiology. Proper processing of RNA is important for the translation of functional proteins. Alterations in RNA processing such as a result of incorrect splicing of RNA can result in disease. For example, mutations in a splice site causes exposure of a premature stop codon, a loss of an exon, or inclusion of an intron. In some instances, alterations in RNA processing results in an insertion, deletion, or duplication. In some instances, alterations in RNA processing results in an insertion, deletion, or duplication of an exon. Alterations in RNA processing, in some cases, results in an insertion, deletion, or duplication of an intron.

Exon Skipping

As used herein, the term "pre-mRNA" refers to the product of transcription which is comprised of both exons (coding sequences) and introns (non-coding sequences). Exon skipping is a form of RNA splicing. In some cases, exon skipping occurs when an exon is skipped over the pre-mRNA transcript or is spliced out of the processed mRNA. As a result of exon skipping, the processed mRNA does not contain the skipped exon. In some instances, exon skipping results in expression of an altered transcript and/or mRNA product. For instance, exon 44 skipping occurs when exon 44 is skipped over in the pre-mRNA transcript or is spliced out of the processed DMD mRNA. As a result of the exon 44 skipping, the processed DMD mRNA does not contain the skipped exon 44. In some instances, exon 44 skipping results in the expression of a truncated dystrophin protein. In some instances, exon 44 skipping results in the expression of a functional dystrophin protein. In some instances, exon 44 skipping results in the expression of a truncated and functional dystrophin protein.

In some instances, morpholino or phosphorodiamidate morpholino oligonucleotide (PMO)-antibody conjugates (PMO-AOC) are used to induce exon skipping. In some instances, morpholino or phosphorodiamidate morpholino oligonucleotide (PMO)-antibody conjugates are used to deliver PMOs for inducing exon skipping (e.g., in a cell, preferably in a muscle cell, etc.). In some instances, the delivered PMOs are used to induce exon skipping. For example, the PMOs bind splice sites or exonic enhancers. In some instances, binding of PMOs to specific mRNA or pre-mRNA sequences generates double-stranded regions. In some instances, PMOs bind to acceptor or donor splice site at the beginning and/or at the end of an exon. In some instances, morpholino or phosphorodiamidate morpholino oligonucleotide (PMO)-antibody conjugates are used to induce exon 44 skipping. In some instances, morpholino or phosphorodiamidate morpholino oligonucleotide (PMO)-antibody conjugates are used to deliver PMOs for inducing exon 44 skipping. The delivered PMOs are used to induce exon 44 skipping. For example, the delivered PMOs bind to at least one of splice sites or exonic enhancers of exon 44. In some instances, binding of PMOs to specific mRNA or pre-mRNA sequences generates double-stranded regions. In some instances, PMOs bind to acceptor or donor splice site at the beginning and/or at the end of exon 44. In some instances, PMOs bind to acceptor splice site at the beginning of exon 44. In some instances, PMOs bind to donor splice site at the beginning of exon 44. In some instances, antisense oligonucleotides (AONs, ASOs) are used to induce exon skipping. As used herein, the term "AONs" is interchangeably used with the term "ASOs" and both refer to antisense oligonucleotides. In some instances, AONs are short nucleic acid sequences that bind to specific mRNA or pre-mRNA sequences. For example, AONs bind to splice sites or exonic enhancers. In some instances, binding of AONs to specific mRNA or pre-mRNA sequences generates double-stranded regions. In some instances, formation of double-stranded regions occurs at sites where the spliceosome or proteins associated with the spliceosome would normally bind to and causes exons to be skipped. In some instances, skipping of exons results in restoration of the transcript reading frame and allows for production of an at least partially functional dystrophin protein.

Indications

In some aspects, a polynucleic acid molecule (oligonucleotide, e.g., PMO, ASO, etc.) or a pharmaceutical composition comprising the polynucleic acid molecule described herein is used for the treatment of a disease or disorder characterized with a defective mRNA. In some aspects, a polynucleic acid molecule (oligonucleotide, e.g., PMO, ASO, etc.) or a pharmaceutical composition comprising the polynucleic acid molecule described herein is used for the treatment of disease or disorder by inducing an insertion, deletion, duplication, or alteration in an incorrectly spliced mRNA transcript to induce exon skipping or exon inclusion.

A large percentage of human protein-coding genes are alternatively spliced. In some instances, a mutation results in improperly spliced or partially spliced mRNA. For example, a mutation can be in at least one of a splice site in a protein coding gene, a silencer or enhancer sequence, exonic sequences, or intronic sequences. In some instances, a mutation results in gene dysfunction. In some instances, a mutation results in a disease or disorder.

Improperly spliced or partially spliced mRNA in some instances causes a neuromuscular disease or disorder. Exemplary neuromuscular diseases include muscular dystrophy such as Duchenne muscular dystrophy, Becker muscular dystrophy, facioscapulohumeral muscular dystrophy, congenital muscular dystrophy, or myotonic dystrophy. In some instances, muscular dystrophy is genetic. In some instances, muscular dystrophy is caused by a spontaneous mutation. Becker muscular dystrophy and Duchenne muscular dystrophy have been shown to involve mutations in the DMD gene, which encodes the protein dystrophin.

In some instances, improperly spliced or partially spliced mRNA causes Duchenne muscular dystrophy. Duchenne muscular dystrophy results in severe muscle weakness and is caused by mutations in the DMD gene that abolishes the production of functional dystrophin. In some instances, Duchenne muscular dystrophy is a result of a mutation in exon 44 in the DMD gene. In some instances, multiple exons are mutated/deleted. For example, mutations of exons 44 and 45 are common in Duchenne muscular dystrophy patients. In some instances, Duchenne muscular dystrophy is a result of mutation of exon 44. In some instances, Duchenne muscular dystrophy is a result of mutation of exon 44 and deletion of exon 45.

In some instances, a polynucleic acid-antibody conjugate or a pharmaceutical composition comprising the polynucleic acid-antibody conjugate as described herein is used for the treatment of muscular dystrophy. In some instances, a polynucleic acid-antibody conjugate or a pharmaceutical composition comprising the polynucleic acid-antibody conjugate as described herein is used for the treatment of Duchenne muscular dystrophy, Becker muscular dystrophy, facioscapulohumeral muscular dystrophy, congenital muscular dystrophy, or myotonic dystrophy. In some instances, a polynucleic acid-antibody conjugate or a pharmaceutical composition comprising the polynucleic acid-antibody conjugate as described herein is used for the treatment of Duchenne muscular dystrophy. In some instances, a PMO-antibody conjugate or a pharmaceutical composition comprising the PMO-antibody conjugate as described herein is used to induce exon 44 skipping for the treatment of muscular dystrophy. In some instances, a PMO-antibody conjugate or a pharmaceutical composition comprising the PMO-antibody conjugate as described herein is used to induce exon 44 skipping for the treatment of Duchenne muscular dystrophy or Becker muscular dystrophy. In some instances, a PMO-antibody conjugate or a pharmaceutical composition comprising the PMO-antibody conjugate as described herein is used to induce exon 44 skipping for the treatment of Duchenne muscular dystrophy.

Antibody-Polynucleic Acid Conjugate

In some aspects, the antibody is conjugated to a polynucleic acid molecule. The polynucleic acid molecule can be ASO or PMO. In some instances, the one or more polynucleic acid molecule is PMO. The antibody can be an anti-transferrin receptor (anti-CD71) antibody or antigen binding fragment thereof. In some aspects, the antibody is conjugated to a polynucleic acid molecule non-specifically. In some instances, the antibody is conjugated to a polynucleic acid molecule via a lysine residue. In some instances, the antibody is conjugated to a polynucleic acid molecule via a cysteine residue. In some instances, the antibody is conjugated to a polynucleic acid molecule via a lysine residue or a cysteine residue, in a non-site specific manner. In some instances, the antibody is conjugated to a polynucleic acid molecule via a lysine residue (e.g., lysine residue present in the antibody in a non-site specific manner. In some cases, the antibody is conjugated to a polynucleic acid molecule via a cysteine residue (e.g., cysteine residue present in the antibody in a non-site specific manner.

In some aspects, the antibody is conjugated to a polynucleic acid molecule in a site-specific manner. In some instances, the antibody is conjugated to a polynucleic acid molecule through a lysine residue, a cysteine residue, at the 5'-terminus, at the 3'-terminus, an unnatural amino acid, or an enzyme-modified or enzyme-catalyzed residue, via a site-specific manner. In some instances, the antibody is conjugated to a polynucleic acid molecule through a lysine residue (e.g., lysine residue present in the antibody via a site-specific manner). In some instances, the antibody is conjugated to a polynucleic acid molecule through a cysteine residue (e.g., cysteine residue present in the antibody via a site-specific manner). In some instances, the antibody is conjugated to a polynucleic acid molecule at the 5'-terminus via a site-specific manner. In some instances, the antibody is conjugated to a polynucleic acid molecule at the 3'-terminus via a site-specific manner. In some instances, the antibody is conjugated to a polynucleic acid molecule through an unnatural amino acid via a site-specific manner. In some instances, the antibody is conjugated to a polynucleic acid molecule through an enzyme-modified or enzyme-catalyzed residue via a site-specific manner. In some instances, the antibody is conjugated to a polynucleic acid molecule via a linker or one or more linkers.

In some aspects, one or more polynucleic acid molecules are conjugated to an antibody. The one or more polynucleic acid molecules can be ASOs or PMOs. In some instances, the one or more polynucleic acid molecules are PMOs. The antibody can be an anti-transferrin receptor (anti-CD71) antibody or antigen binding fragment thereof. In some instances, about 1, 2, 3, 4, 5, 6, 7, 8, 9, 10, 11, 12, 13, 14, 15, 16, or more polynucleic acid molecules are conjugated to one antibody. In some instances, about 1 polynucleic acid molecule is conjugated to one antibody. In some instances, about 2 polynucleic acid molecules are conjugated to one antibody. In some instances, about 3 polynucleic acid molecules are conjugated to one antibody. In some instances, about 4 polynucleic acid molecules are conjugated to one antibody. In some instances, about 5 polynucleic acid molecules are conjugated to one antibody. In some instances, about 6 polynucleic acid molecules are conjugated to one antibody. In some instances, about 7 polynucleic acid molecules are conjugated to one antibody. In some instances, about 8 polynucleic acid molecules are conjugated to one antibody. In some instances, about 9 polynucleic acid molecules are conjugated to one antibody. In some instances, about 10 polynucleic acid molecules are conjugated to one antibody. In some instances, about 11 polynucleic acid molecules are conjugated to one antibody. In some instances, about 12 polynucleic acid molecules are conjugated to one antibody. In some instances, about 13 polynucleic acid molecules are conjugated to one antibody. In some instances, about 14 polynucleic acid molecules are conjugated to one antibody. In some instances, about 15 polynucleic acid molecules are conjugated to one antibody. In some instances, about 16 polynucleic acid molecules are conjugated to one antibody. In some cases, the one or more polynucleic acid molecules are the same. In other cases, the one or more polynucleic acid molecules are different.

In some aspects, the number of polynucleic acid molecule conjugated to an antibody forms a ratio. In some instances, the ratio is referred to as a DAR (drug-to-antibody) ratio, in which the drug as referred to herein is the polynucleic acid molecule. In some instances, the DAR ratio of the polynucleic acid molecule to antibody is about 1, 2, 3, 4, 5, 6, 7, 8, 9, 10, 11, 12, 13, 14, 15, 16, or greater. In some instances, the DAR ratio of the polynucleic acid molecule to antibody A is approximately 1, 2, 3, 4, 5, 6, 7, 8, 9, 10, 11, 12, 13, 14, 15, 16, or greater. In some instances, the DAR ratio includes whole number as well as fractions or decimal of a DAR ratio. For instance, the fractions or decimal of a DAR ratio includes X.1, X.2, X.3, X.4, X.5, X.6, X.7, X.8, X.9 (e.g., 2.1, 2.2, 2.3, 2.4, 2.5, 2.6, 2.7, 2.8, 2.9, etc.). In some instances, the DAR ratio of the polynucleic acid molecule to antibody is about 1 or greater. In some instances, the DAR ratio of the polynucleic acid molecule to antibody is about 2 or greater. In some instances, the DAR ratio of the polynucleic acid molecule to antibody is about 3 or greater. In some instances, the DAR ratio of the polynucleic acid molecule to antibody is about 4 or greater. In some instances, the DAR ratio of the polynucleic acid molecule to antibody is about 5 or greater. In some instances, the DAR ratio of the polynucleic acid molecule to antibody is about 6 or greater. In some instances, the DAR ratio of the polynucleic acid molecule to antibody is about 7 or greater. In some instances, the DAR ratio of the polynucleic acid molecule to antibody is about 8 or greater. In some instances, the DAR ratio of the polynucleic acid molecule to antibody is about 9 or greater. In some instances, the DAR ratio of the polynucleic acid molecule to antibody is about 10 or greater. In some instances, the DAR ratio of the polynucleic acid molecule to antibody is about 11 or greater. In some instances, the DAR ratio of the polynucleic acid molecule to antibody is about 12 or greater.

In some instances, the DAR ratio of the polynucleic acid molecule to antibody is about 1, 2, 3, 4, 5, 6, 7, 8, 9, 10, 11, 12, 13, 14, 15, or 16. In some instances, the DAR ratio of the polynucleic acid molecule to antibody is about 1. In some instances, the DAR ratio of the polynucleic acid molecule to antibody is about 2. In some instances, the DAR ratio of the polynucleic acid molecule to antibody is about 3. In some instances, the DAR ratio of the polynucleic acid molecule to antibody is about 4. In some instances, the DAR ratio of the polynucleic acid molecule to antibody is about 5. In some instances, the DAR ratio of the polynucleic acid molecule to antibody is about 6. In some instances, the DAR ratio of the polynucleic acid molecule to antibody is about 7. In some instances, the DAR ratio of the polynucleic acid molecule to antibody is about 8. In some instances, the DAR ratio of the polynucleic acid molecule to antibody is about 9. In some instances, the DAR ratio of the polynucleic acid molecule to antibody is about 10. In some instances, the DAR ratio of the polynucleic acid molecule to antibody is about 11. In some instances, the DAR ratio of the polynucleic acid molecule to antibody is about 12. In some instances, the DAR ratio of the polynucleic acid molecule to antibody is about 13. In some instances, the DAR ratio of the polynucleic acid molecule to antibody is about 14. In some instances, the DAR ratio of the polynucleic acid molecule to antibody is about 15. In some instances, the DAR ratio of the polynucleic acid molecule to antibody is about 16.

In some instances, the DAR ratio of the polynucleic acid molecule to antibody is 1, 2, 3, 4, 5, 6, 7, 8, 9, 10, 11, 12, 13, 14, 15, or 16. In some instances, the DAR ratio of the polynucleic acid molecule to antibody is 1. In some instances, the DAR ratio of the polynucleic acid molecule to antibody is 2. In some instances, the DAR ratio of the polynucleic acid molecule to antibody is 4. In some instances, the DAR ratio of the polynucleic acid molecule to antibody is 6. In some instances, the DAR ratio of the polynucleic acid molecule to antibody is 8. In some instances, the DAR ratio of the polynucleic acid molecule to antibody is 12. In some instances, the DAR ratio of the polynucleic acid molecule to antibody is 16.

In some aspects, a composition comprises a plurality of antibody-polynucleic acid conjugates. In some instances, the number of polynucleic acid molecule conjugated to an antibody forms a ratio. In some instances, the ratio is referred to as a DAR (drug-to-antibody) ratio, in which the drug as referred to herein is the polynucleic acid molecule. In some instances, the plurality of antibody-polynucleic acid conjugates in the composition has the same DAR ratio. In some instances, the plurality of antibody-polynucleic acid conjugates in the composition has different DAR ratios. In some instances, at least two of the antibody-polynucleic acid congujages in the composition have different DAR ratios to each other. In some instances, the DAR ratio is an average DAR (drug-to-antibody) ratio, which is an average number of the DAR ratios of the plurality of antibody-polynucleic acid conjugates in the composition. In some instances, the average DAR ratio of the polynucleic acid molecule to antibody is about 1, 2, 3, 4, 5, 6, 7, 8, 9, 10, 11, 12, 13, 14, 15, 16, or greater. In some instances, the average DAR ratio of the polynucleic acid molecule to antibody is approximately 1, 2, 3, 4, 5, 6, 7, 8, 9, 10, 11, 12, 13, 14, 15, 16, or greater. In some instances, the average DAR ratio includes whole number as well as fractions or decimal of a DAR ratio. In some instances, the average DAR ratio of the polynucleic acid molecule to antibody is about 1 or greater. In some instances, the average DAR ratio of the polynucleic acid molecule to antibody is about 2 or greater. In some instances, the average DAR ratio of the polynucleic acid molecule to antibody is about 3 or greater. In some instances, the average DAR ratio of the polynucleic acid molecule to antibody is about 4 or greater. In some instances, the average DAR ratio of the polynucleic acid molecule to antibody is about 5 or greater. In some instances, the average DAR ratio of the polynucleic acid molecule to antibody is about 6 or greater. In some instances, the average DAR ratio of the polynucleic acid molecule to antibody is about 7 or greater. In some instances, the average DAR ratio of the polynucleic acid molecule to antibody is about 8 or greater. In some instances, the average DAR ratio of the polynucleic acid molecule to antibody is about 9 or greater. In some instances, the average DAR ratio of the polynucleic acid molecule to antibody is about 10 or greater. In some instances, the average DAR ratio of the polynucleic acid molecule to antibody is about 11 or greater. In some instances, the average DAR ratio of the polynucleic acid molecule to antibody is about 12 or greater.

In some instances, the average DAR ratio of the polynucleic acid molecule to antibody A is about 1, 2, 3, 4, 5, 6, 7, 8, 9, 10, 11, 12, 13, 14, 15, or 16. In some instances, the average DAR ratio of the polynucleic acid molecule to antibody is about 1. In some instances, the average DAR ratio of the polynucleic acid molecule to antibody is about 2. In some instances, the average DAR ratio of the polynucleic acid molecule to antibody is about 3. In some instances, the average DAR ratio of the polynucleic acid molecule to antibody is about 4. In some instances, the average DAR ratio of the polynucleic acid molecule to antibody is about 5. In some instances, the average DAR ratio of the polynucleic acid molecule to antibody is about 6. In some instances, the average DAR ratio of the polynucleic acid molecule to antibody is about 7. In some instances, the average DAR ratio of the polynucleic acid molecule to antibody is about 8. In some instances, the average DAR ratio of the polynucleic acid molecule to antibody is about 9. In some instances, the average DAR ratio of the polynucleic acid molecule to antibody is about 10. In some instances, the average DAR ratio of the polynucleic acid molecule to antibody is about 11. In some instances, the average DAR ratio of the polynucleic acid molecule to antibody is about 12. In some instances, the average DAR ratio of the polynucleic acid molecule to antibody is about 13. In some instances, the average DAR ratio of the polynucleic acid molecule to antibody is about 14. In some instances, the DAR ratio of the polynucleic acid molecule to antibody is about 15. In some instances, the average DAR ratio of the polynucleic acid molecule to antibody is about 16.

In some instances, the average DAR ratio of the polynucleic acid molecule to antibody is 1, 2, 3, 4, 5, 6, 7, 8, 9, 10, 11, 12, 13, 14, 15, or 16. In some instances, the average DAR ratio of the polynucleic acid molecule to antibody is 1. In some instances, the average DAR ratio of the polynucleic acid molecule to antibody is 2. In some instances, the average DAR ratio of the polynucleic acid molecule to antibody is 4. In some instances, the average DAR ratio of the polynucleic acid molecule to antibody is 6. In some instances, the average DAR ratio of the polynucleic acid molecule to antibody is 8. In some instances, the average DAR ratio of the polynucleic acid molecule to antibody is 12. In some instances, the average DAR ratio of the polynucleic acid molecule to antibody is 16.

In some instances, the average DAR ratio of the polynucleic acid molecule to antibody is in the range of 1.5-2.5, 2.5-3.5, 3.5-4.5, 4.5-5.5, 5.5-6.5, 6.5-7.5, 7.5-8.5, 8.5-9.5, 9.5-10.5, 10.5-11.5, 11.5-12.5, 12.5-13.5, 13.5-14.5, 14.5-15.5, 15.5-16.5, or 16.5-17.5. In some instances, the average DAR ratio of the polynucleic acid molecule to antibody A is in the range of 1.5-2.5. In some instances, the average DAR ratio of the polynucleic acid molecule to antibody is in the range of 2.5-3.5. In some instances, the average DAR ratio of the polynucleic acid molecule to antibody is in the range of 3.5-4.5. In some instances, the average DAR ratio of the polynucleic acid molecule to antibody is in the range of 4.5-5.5. In some instances, the average DAR ratio of the polynucleic acid molecule to antibody is in the range of 5.5-6.5. In some instances, the average DAR ratio of the polynucleic acid molecule to antibody is in the range of 6.5-7.5. In some instances, the average DAR ratio of the polynucleic acid molecule to antibody is in the range of 7.5-8.5. In some instances, the average DAR ratio of the polynucleic acid molecule to antibody is in the range of 8.5-9.5. In some instances, the average DAR ratio of the polynucleic acid molecule to antibody is in the range of 9.5-10.5. In some instances, the average DAR ratio of the polynucleic acid molecule to antibody is in the range of 10.5-11.5. In some instances, the average DAR ratio of the polynucleic acid molecule to antibody A is in the range of 11.5-12.5. In some instances, the average DAR ratio of the polynucleic acid molecule to antibody is in the range of 12.5-13.5. In some instances, the average DAR ratio of the polynucleic acid molecule to antibody is in the range of 13.5-14.5. In some instances, the average DAR ratio of the polynucleic acid molecule to antibody is in the range of 14.5-15.5. In some instances, the DAR ratio of the polynucleic acid molecule to antibody is in the range of 15.5-16.5. In some instances, the average DAR ratio of the polynucleic acid molecule to antibody is in the range of 16.5-17.5.

In some instances, a conjugate comprising a polynucleic acid molecule and an antibody has improved activity as compared to a conjugate comprising a polynucleic acid molecule without an antibody. In some instances, improved activity results in enhanced biologically relevant functions, e.g., improved stability, affinity, binding, functional activity, and efficacy in treatment or prevention of a disease state. In some instances, the disease state is a result of one or more mutated exons of a gene. In some instances, the conjugate comprising a polynucleic acid molecule and an antibody results in increased exon skipping of the one or more mutated exons as compared to the conjugate comprising a polynucleic acid molecule without an antibody. In some instances, exon skipping is increased by at least or about 5%, 10%, 20%, 25%, 30%, 40%, 50%, 60%, 70%, 80%, 90%, 95%, or more than 95% in the conjugate comprising polynucleic acid molecule and antibody A as compared to the conjugate comprising polynucleic acid molecule without an antibody.

PMO Molecule of the PMO-Antibody Conjugate

In some aspects, the polynucleic acid is an antisense oligonucleotide (ASO) or a PMO molecule. In some aspects, the antibody-polynucleic acid conjugate is an ASO-antibody conjugate. In some aspects, the—antibody-polynucleic acid conjugate is a PMO-antibody conjugate. In some aspects, a PMO molecule of the PMO-antibody conjugate described herein induces exon 44 skipping to induce an alteration in an incorrectly spliced mRNA transcript. In some instances, the PMO molecule restores the translational reading frame of the dystrophin protein by altering the incorrectly spliced mRNA transcript. In some instances, the PMO molecule results in a functional and truncated dystrophin protein by restoring the translational reading frame of the dystrophin protein.

In some aspects, a polynucleic acid molecule is conjugated to an antibody for delivery to a site of interest. In some cases, a PMO molecule is conjugated to an antibody. In some cases, a PMO molecule is conjugated to an antibody for delivery to a site of interest.

In some aspects, a PMO molecule is conjugated to an antibody for delivery to a muscle cell. In some cases, a PMO molecule for skipping exon 44 is conjugated to an antibody. In some cases, a PMO molecule for skipping exon 44 is conjugated to an antibody for delivery to a muscle cell.

In some instances, an antibody is conjugated to at least one PMO molecule. In some instances, the antibody is conjugated to the at least one PMO molecule to form an PMO-antibody conjugate. In some aspects, the antibody is conjugated to the 5' terminus of the PMO molecule, the 3' terminus of the PMO molecule, an internal site on the PMO molecule, or in any combinations thereof. In some instances, the antibody is conjugated to at least two PMO molecules. In some instances, the antibody is conjugated to at least 2, 3, 4, 5, 6, 7, 8, or more PMO molecules.

In some instances, a PMO molecule of the PMO-antibody conjugate targets and hybridizes to a pre-mRNA sequence of the DMD gene. In some instances, the PMO molecule targets and hybridizes a splice site of exon 44 of the pre-mRNA sequence of the DMD gene. In some instances, the PMO molecule targets and hybridizes a cis-regulatory element of exon 44 of the pre-mRNA sequence of the DMD gene. In some instances, the PMO molecule targets and hybridizes a trans-regulatory element of exon of the pre-mRNA sequence of the DMD gene. In some instances, the PMO molecule targets exonic splice enhancers or intronic splice enhancers of exon 44 of the pre-mRNA sequence of the DMD gene. In some instances, the PMO molecule targets and hybridizes exonic splice silencers or intronic splice silencers of exon 44 of the pre-mRNA sequence of the DMD gene. In some instances, the PMO molecule targets and hybridizes to the acceptor site of exon 44 of the pre-mRNA sequence of the DMD gene.

In some instances, a PMO molecule of the PMO-antibody conjugate targets and hybridizes a sequence found in introns or exons of the pre-mRNA sequence of the DMD gene. For example, the PMO molecule targets and hybridizes to a sequence found in exon 44 of the pre-mRNA sequence of the DMD gene that mediates splicing of said exon. In some instances, the PMO molecule targets an exon recognition sequence of the pre-mRNA sequence of the DMD gene. In some instances, the PMO molecule targets a sequence upstream of an exon of the pre-mRNA sequence of the DMD gene. In some instances, the PMO molecule targets a sequence downstream of an exon of the pre-mRNA sequence of the DMD gene.

As described above, a PMO molecule targets an incorrectly processed mRNA transcript which results in a neuromuscular disease or disorder. In some cases, a neuromuscular disease or disorder is Duchenne muscular dystrophy or Becker muscular dystrophy.

In some instances, the polynucleic acid molecule (e.g., a PMO molecule, an antisense oligonucleotide, etc.) targets a region (a sequence) adjacent to a mutated exon. In another instance, if there is a mutation in exon 44, the polynucleic acid molecule targets a sequence in exon 44 (e.g., a region within exon 44) of the pre-mRNA sequence of the DMD gene so that exon 44 is skipped.

In some cases, a polynucleic acid molecule described herein targets a region that is at the exon-intron junction of exon 44 of the pre-mRNA sequence of the DMD gene. In some cases, a polynucleic acid molecule described herein targets a region that is at the exon-intron junction of exon 44 of the pre-mRNA sequence of the DMD gene.

In some instances, the PMO molecule of the PMO-antibody conjugate hybridizes to a target region that is at either the 5' intron-exon junction or the 3' exon-intron junction of exon 44 of the pre-mRNA of the DMD gene.

In some cases, the polynucleic acid molecule hybridizes to a target region that is at the 5' intron-exon junction of exon 44 of the pre-mRNA of the DMD gene.

In some cases, the PMO molecule hybridizes to a target region that is at the 3' exon-intron junction of exon 44 of the pre-mRNA of the DMD gene.

In some instances, a PMO molecule of the PMO-antibody conjugate described herein targets a splice site of exon 44 of the pre-mRNA of the DMD gene. In some cases, a PMO molecule of the PMO-antibody conjugate described herein targets a splice site of exon 44 of the pre-mRNA of the DMD gene. As used herein, a splice site includes a canonical splice site, a cryptic splice site or an alternative splice site that is capable of inducing an insertion, deletion, duplication, or alteration in an incorrectly spliced mRNA transcript to induce exon 44 skipping.

In some instances, the PMO molecule of the PMO-antibody conjugate hybridizes to a target region that is proximal to the exon-intron junction. In some instances, a PMO molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt upstream (or the 5') of exon 44 of the pre-mRNA of the DMD gene. In some instances, a PMO molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or the 5') of exon 44 of the pre-mRNA of the DMD gene.

In some instances, the PMO molecule of the PMO-antibody conjugate hybridizes to a target region that is downstream (or 3') to exon 44 of the pre-mRNA of the DMD gene. In some instances, the polynucleic acid molecule hybridizes to a target region that is about 5, 10, 15, 20, 50, 100, 200, 300, 400 or 500 nt downstream (or 3') to exon 44 of the pre-mRNA of the DMD gene.

In some instances, a PMO molecule of the PMO-antibody conjugate described herein targets an internal region within exon 44 of the pre-mRNA of the DMD gene.

In some aspects, the PMO molecule of the PMO-antibody conjugate described herein targets a partially spliced mRNA sequence comprising exon 44 of the pre-mRNA of the DMD gene. In some instances, the PMO molecule hybridizes to a target region that is upstream (or 5') to exon 44 of the pre-mRNA of the DMD gene. In some instances, the PMO molecule hybridizes to a target region that is about 5, 10, 15, 20, 50, 100, 200, 300, 400 or 500 bp upstream (or 5') to exon 44 of the pre-mRNA of the DMD gene. In some instances, the PMO molecule hybridizes to a target region that is downstream (or 3') to exon 44 of the pre-mRNA of the DMD gene. In some instances, the PMO molecule hybridizes to a target region that is about 5, 10, 15, 20, 50, 100, 200, 300, 400 or 500 bp downstream (or 3') to exon 44 of the pre-mRNA of the DMD gene.

In some instances, the PMO molecule hybridizes to a target region that is within exon 44 of the pre-mRNA of the DMD gene. In some instances, the PMO molecule hybridizes to a target region that is at either the 5' intron-exon 44 junction or the 3' exon 44-intron junction of the pre-mRNA of the DMD gene.

In some aspects, the PMO molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 100-133.

In some aspects, the PMO molecule comprises a core sequence having at least 50%, 55%, 60%, 65%, 70%, 75%, 80%, 85%, 90%, 95%, 96%, 97%, 98%, 99%, or 10000 sequence identity to a sequence selected from SEQ ID NOs: 100-133.

In some aspects, the PMO molecule of the PMO-antibody conjugate comprises at least 10, 15, 16, 17, 18, 19, 20, 21, 22, 23, 24, 25, 26, 27, 28, 29, 30 or more contiguous bases of a sequence selected from SEQ ID NOs: 100-133. In some cases, the PMO molecule further comprises 1, 2, 3, or 4 mismatches or no more than 1, 2, 3, or 4 mismatches from a sequence selected from SEQ ID NOs: 100-133.

Tables 1 and 2 list the PMO molecules of SEQ ID NOs:100-133.

TABLE 1

| PMO (30-mer) | Sequence (5'-3') | SEQ ID NO: |
|---|---|---|
| hEx44_Ac0 | CGCCATTTCTCAACAGATCTGTCAAATCGC | 100 |
| hEx44_Ac1 | CCGCCATTTCTCAACAGATCTGTCAAATCG | 101 |
| hEx44_Ac2 | GCCGCCATTTCTCAACAGATCTGTCAAATC | 102 |
| hEx44_Ac3 | AGCCGCCATTTCTCAACAGATCTGTCAAAT | 103 |
| hEx44_Ac4 | AAGCCGCCATTTCTCAACAGATCTGTCAAA | 104 |
| hEx44_Ac5 | AAAGCCGCCATTTCTCAACAGATCTGTCAA | 105 |
| hEx44_Ac6 | AAAAGCCGCCATTTCTCAACAGATCTGTCA | 106 |
| hEx44_Ac7 | AAAACGCCGCCATTTCTCAACAGATCTGTC | 107 |
| hEx44_Ac8 | GAAAACGCCGCCATTTCTCAACAGATCTGT | 108 |
| hEx44_Ac9 | TGAAAACGCCGCCATTTCTCAACAGATCTG | 109 |
| hEx44_Ac10 | ATGAAAACGCCGCCATTTCTCAACAGATCT | 110 |
| hEx44_Ac14 | CATAATGAAAACGCCGCCATTTCTCAACAG | 111 |

TABLE 2

| PMO Name | Target Site | PMO length | PMO molecule (5'-3') | SEQ ID NO: |
|---|---|---|---|---|
| hEx_44_Ac2_25 | Ac2 | 25 | CATTTCTCAACAGATCTGTCAAATC | 112 |
| hEx_44_Ac4_25 | Ac4 | 25 | GCCATTTCTCAACAGATCTGTCAAA | 113 |
| hEx_44_Ac5_25 | Ac5 | 25 | CGCCATTTCTCAACAGATCTGTCAA | 114 |
| hEx_44_Ac7_25 | Ac7 | 25 | GCCGCCATTTCTCAACAGATCTGTC | 115 |
| hEx_44_Ac4_26 | Ac4 | 26 | CGCCATTTCTCAACAGATCTGTCAAA | 116 |
| hEx_44_Ac5_26 | Ac5 | 26 | CCGCCATTTCTCAACAGATCTGTCAA | 117 |
| hEx_44_Ac7_26 | Ac7 | 26 | CGCCGCCATTTCTCAACAGATCTGTC | 118 |
| hEx_44_Ac8_26 | Ac8 | 26 | ACGCCGCCATTTCTCAACAGATCTGT | 119 |
| hEx_44_Ac4_27 | Ac4 | 27 | CCGCCATTTCTCAACAGATCTGTCAAA | 120 |

TABLE 2-continued

| PMO Name | Target Site | PMO length | PMO molecule (5'-3') | SEQ ID NO: |
|---|---|---|---|---|
| hEx_44_Ac5_27 | Ac5 | 27 | GCCGCCATTTCTCAACAGATCTGTCAA | 121 |
| hEx_44_Ac6_27 | Ac6 | 27 | CGCCGCCATTTCTCAACAGATCTGTCA | 122 |
| hEx_44_Ac7_27 | Ac7 | 27 | ACGCCGCCATTTCTCAACAGATCTGTC | 123 |
| hEx_44_Ac2_28 | Ac2 | 28 | CGCCATTTCTCAACAGATCTGTCAAATC | 124 |
| hEx_44_Ac3_28 | Ac3 | 28 | CCGCCATTTCTCAACAGATCTGTCAAAT | 125 |
| hEx_44_Ac4_28 | Ac4 | 28 | GCCGCCATTTCTCAACAGATCTGTCAAA | 126 |
| hEx_44_Ac5_28 | Ac5 | 28 | CGCCGCCATTTCTCAACAGATCTGTCAA | 127 |
| hEx_44_Ac6_28 | Ac6 | 28 | ACGCCGCCATTTCTCAACAGATCTGTCA | 128 |
| hEx_44_Ac7_28 | Ac7 | 28 | AACGCCGCCATTTCTCAACAGATCTGTC | 129 |
| hEx_44_Ac24_28 | Ac24 | 28 | CTTTATATCATAATGAAAACGCCGCCAT | 130 |
| hEx_44_Ac25_28 | Ac25 | 28 | TCTTTATATCATAATGAAAACGCCGCCA | 131 |
| hEx_44_Ac26_28 | Ac26 | 28 | ATCTTTATATCATAATGAAAACGCCGCC | 132 |
| hEx_44_Ac-Core_25 | Ac4/Ac5/Ac7 | 25 | GCCGCCATTTCTCAACAGATCTGTC | 133 |

In some aspects, the polynucleic acid molecule is an antisense oligonucleotide (ASO) or phosphorodiamidate morpholino oligonucleotide (PMO) molecule.

In some aspects, the PMO molecule is from about 10 to about 50 nucleotides in length. In some instances, the PMO molecule is from about 10 to about 30, from about 15 to about 30, from about 18 to about 30, from about 18 to about 25, from about 18 to about 24, from about 19 to about 23, from about 19 to about 30, from about 19 to about 25, from about 19 to about 24, from about 19 to about 23, from about 20 to about 30, from about 20 to about 25, from about 20 to about 24, from about 20 to about 23, or from about 20 to about 22 nucleotides in length.

In some aspects, the polynucleic acid molecule comprises natural, synthetic, or artificial nucleotide analogues or bases. In some cases, the ASO molecule or the PMO molecule of the polynucleic acid molecule-antibody conjugate (e.g., PMO-antibody conjugate or ASO-antibody conjugate) comprises combinations of DNA, RNA and/or nucleotide analogues. In some instances, the synthetic or artificial nucleotide analogues or bases comprise modifications at one or more of ribose moiety, phosphate moiety, nucleoside moiety, or a combination thereof.

In some aspects, the nucleotide analogues or artificial nucleotide bases comprise a nucleic acid with a modification at a 2' hydroxyl group of the ribose moiety. In some instances, the modification includes an H, OR, R, halo, SH, SR, NH2, NHR, NR2, or CN, wherein R is an alkyl moiety. Exemplary alkyl moieties include, but are not limited to, halogens, sulfurs, thiols, thioethers, thioesters, amines (primary, secondary, or tertiary), amides, ethers, esters, alcohols, and oxygen. In some instances, the alkyl moiety further comprises a modification. In some instances, the modification comprises an azo group, a keto group, an aldehyde group, a carboxyl group, a nitro group, a nitroso group, a nitrile group, a heterocycle (e.g., imidazole, hydrazino or hydroxylamino) group, an isocyanate or cyanate group, or a sulfur containing group (e.g., sulfoxide, sulfone, sulfide, or disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

In some instances, the modification at the 2' hydroxyl group is a 2'-O-methyl modification or a 2'-O-methoxyethyl (2'-O-MOE) modification. In some cases, the 2'-O-methyl modification adds a methyl group to the 2' hydroxyl group of the ribose moiety whereas the 2'O-methoxyethyl modification adds a methoxyethyl group to the 2' hydroxyl group of the ribose moiety. Exemplary chemical structures of a 2'-O-methyl modification of an adenosine molecule and 2'O-methoxyethyl modification of a uridine are illustrated below.

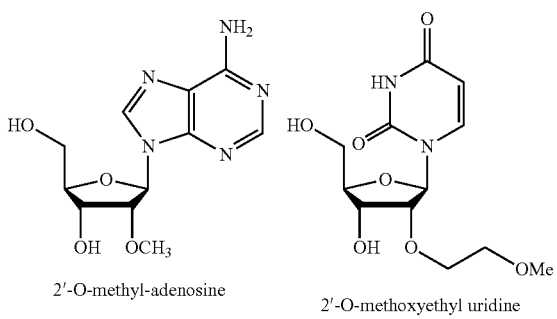

2'-O-methyl-adenosine

2'-O-methoxyethyl uridine

In some instances, the modification at the 2' hydroxyl group is a 2'-O-aminopropyl modification in which an extended amine group comprising a propyl linker binds the amine group to the 2' oxygen. In some instances, this modification neutralizes the phosphate derived overall negative charge of the oligonucleotide molecule by introducing one positive charge from the amine group per sugar and thereby improves cellular uptake properties due to its zwitterionic properties. An exemplary chemical structure of a 2'-O-aminopropyl nucleoside phosphoramidite is illustrated below.

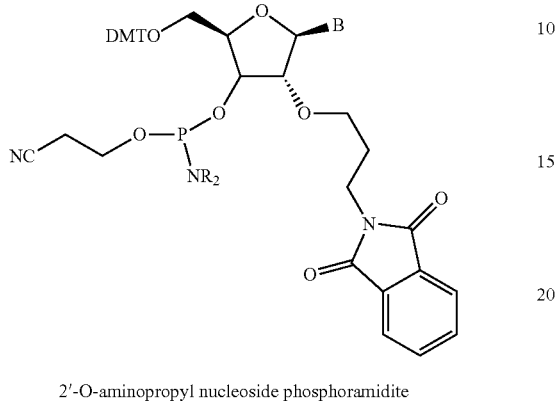

2'-O-aminopropyl nucleoside phosphoramidite

In some instances, the modification at the 2' hydroxyl group is a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivities of an LNA monomer. The representation shown to the right highlights the locked 3'-endo (3E) conformation of the furanose ring of an LNA monomer.

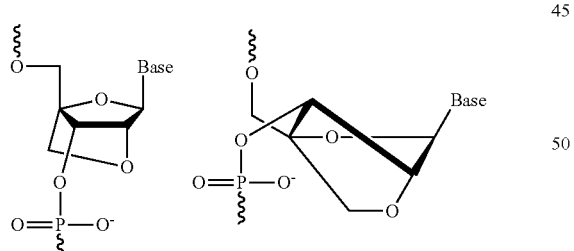

LNA (Locked Nucleic Acids)

In some instances, the modification at the 2' hydroxyl group comprises ethylene nucleic acids (ENA) such as for example 2'-4'-ethylene-bridged nucleic acid, which locks the sugar conformation into a C3'-endo sugar puckering conformation. ENAs are part of the bridged nucleic acids class of modified nucleic acids that also comprises LNA. Exemplary chemical structures of the ENA and bridged nucleic acids are illustrated below.

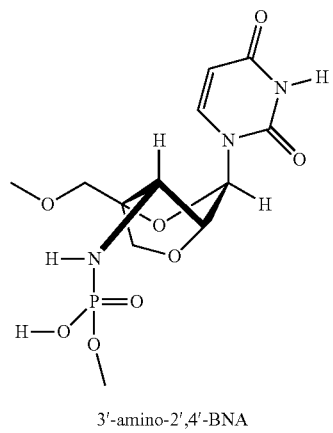

3'-amino-2',4'-BNA

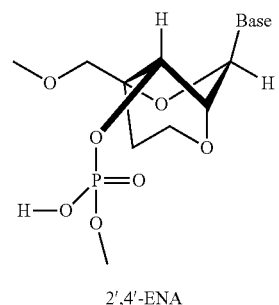

2',4'-ENA

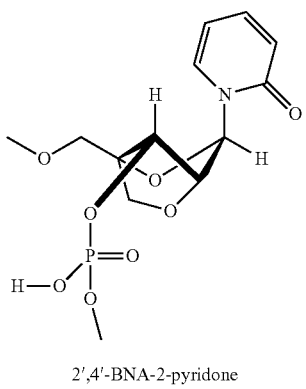

2',4'-BNA-2-pyridone

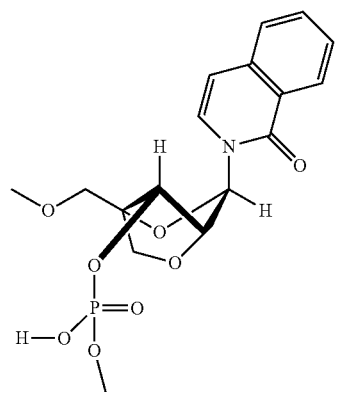

2',4'-BNA-1-isoquinolone

In some aspects, additional modifications at the 2' hydroxyl group include 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA).

In some aspects, nucleotide analogues comprise modified bases such as, but not limited to, 5-propynyluridine, 5-propynylcytidine, 6-methyladenine, 6-methylguanine, N, N, -dimethyladenine, 2-propyladenine, 2propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyi nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties, in some cases are or are based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some aspects, nucleotide analogues further comprise morpholinos, peptide nucleic acids (PNAs), methylphosphonate nucleotides, thiolphosphonate nucleotides, 2'-fluoro N3-P5'-phosphoramidites, 1', 5'-anhydrohexitol nucleic acids (HNAs), or a combination thereof.

Morpholinos or phosphorodiamidate morpholino oligomers (PMOs) comprise synthetic molecules whose structures mimic natural nucleic acid structures by deviating from the normal sugar and phosphate structures. In some instances, the five member ribose ring is substituted with a six member morpholino ring containing four carbons, one nitrogen and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides.

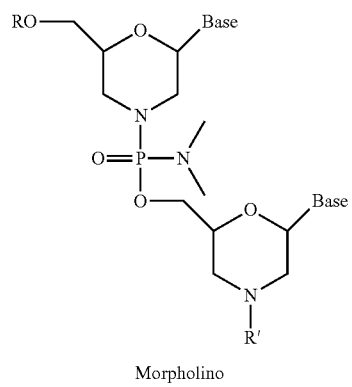

Morpholino

In some aspects, the peptide nucleic acid (PNA) does not contain a sugar ring or phosphate linkage and the bases are attached and appropriately spaced by oligoglycine-like molecules, therefore, eliminating a backbone charge.

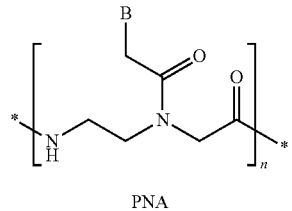

PNA

In some aspects, one or more modifications optionally occur at the intemucleotide linkage. In some instances, modified intemucleotide linkages include, but are not limited to, phosphorothioates, phosphorodithioates, methylphosphonates, 5'-alkylenephosphonates, 5'-methylphosphonates, 3'-alkylene phosphonates, borontrifluoridates, borano phosphate esters and selenophosphates with 3'-5' linkages or 2'-5' linkages, phosphotriesters, thionoalkylphosphotriesters, hydrogen phosphonate linkages, alkyl phosphonates, alkylphosphonothioates, arylphosphonothioates, phosphoroselenoates, phosphorodiselenoates, phosphinates, phosphoramidates, 3'-alkylphosphoramidates, aminoalkylphosphoramidates, thionophosphoramidates, phosphoropiperazidates, phosphoroanilothioates, phosphoroanilidates, ketones, sulfones, sulfonamides, carbonates, carbamates, methylenehydrazos, methylenedimethylhydrazos, formacetals, thioformacetals, oximes, methyleneiminos, methylenemethyliminos, thioamidates, linkages with riboacetyl groups, aminoethyl glycine, silyl or siloxane linkages, alkyl or cycloalkyl linkages with or without heteroatoms of, for example, 1 to 10 carbons that are saturated or unsaturated and/or substituted and/or contain heteroatoms, linkages with morpholino structures, amides, polyamides wherein the bases are attached to the aza nitrogens of the backbone directly or indirectly, and combinations thereof. Phosphorothioate antisense oligonucleotides (PS ASO) are antisense oligonucleotides comprising a phosphorothioate linkage. An exemplary PS ASO is illustrated below.

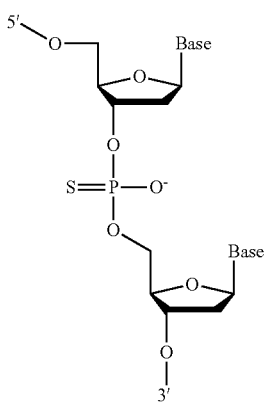

In some instances, the modification is a methyl or thiol modification such as methylphosphonate or thiolphosphonate modification. An exemplary thiolphosphonate nucleotide (left) and an methylphosphonate nucleotide (right) are illustrated below.

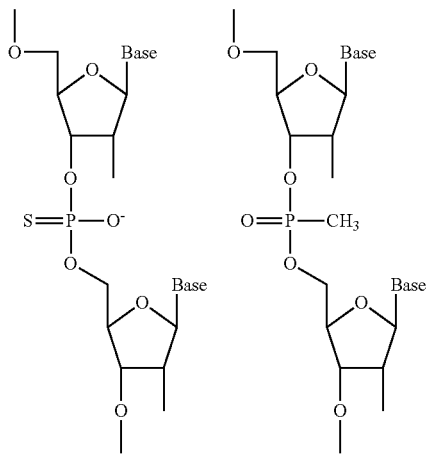

In some instances, a modified nucleotide includes, but is not limited to, 2'-fluoro N3-P5'-phosphoramidites illustrated as:

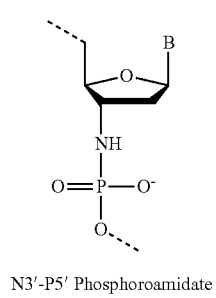

N3'-P5' Phosphoroamidate

In some instances, a modified nucleotide includes, but is not limited to, hexitol nucleic acid (or 1', 5'-anhydrohexitol nucleic acids (HNA)) illustrated as:

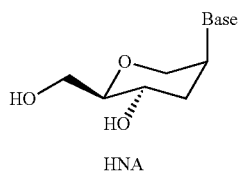

HNA

In some aspects, a nucleotide analogue or artificial nucleotide base described above comprises a 5'-vinylphosphonate modified nucleotide with a modification at a 5' hydroxyl group of the ribose moiety. In some aspects, the 5'-vinylphosphonate modified nucleotide is selected from the nucleotides provided below, wherein X is O or S; and B is a heterocyclic base moiety.

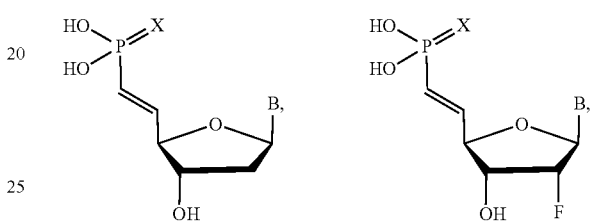

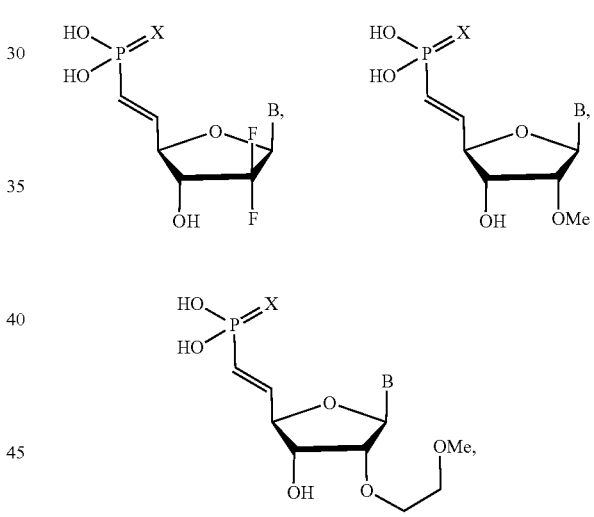

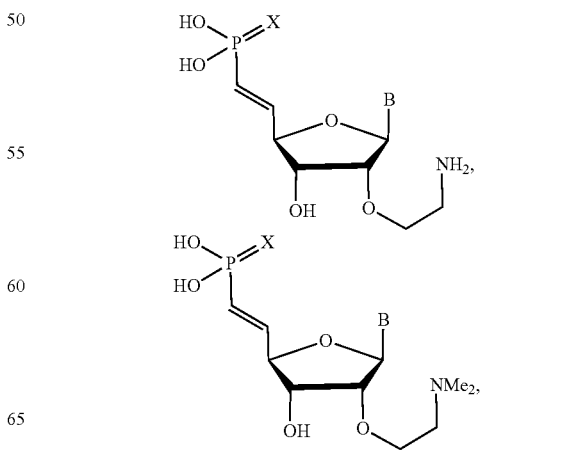

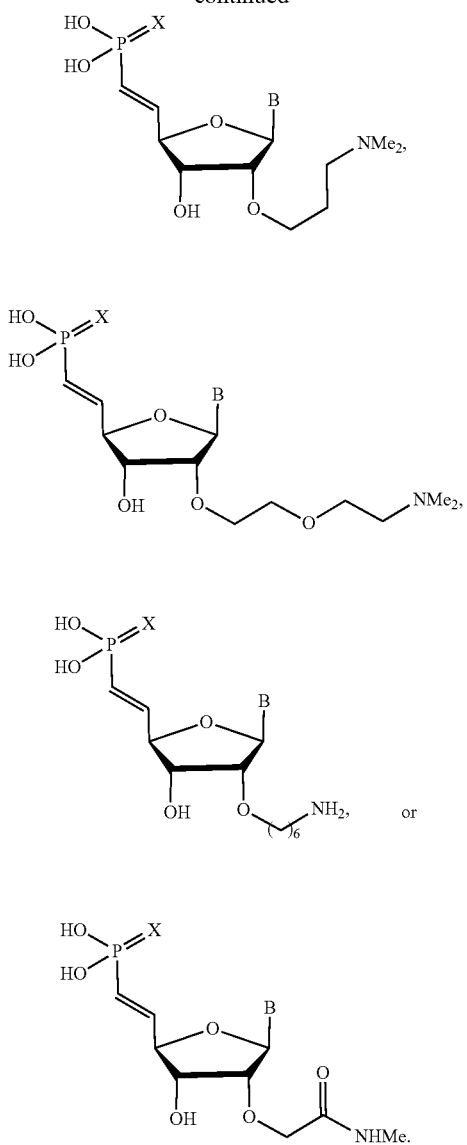

In some instances, the modification at the 2' hydroxyl group is a 2'-O-aminopropyl modification in which an extended amine group comprising a propyl linker binds the amine group to the 2' oxygen. In some instances, this modification neutralizes the phosphate-derived overall negative charge of the oligonucleotide molecule by introducing one positive charge from the amine group per sugar and thereby improves cellular uptake properties due to its zwitterionic properties.

In some instances, the 5'-vinylphosphonate modified nucleotide is further modified at the 2' hydroxyl group in a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of 5'-vinylphosphonate modified LNA are illustrated below, wherein X is O or S; B is a heterocyclic base moiety; and J is an internucleotide linking group linking to the adjacent nucleotide of the polynucleotide.

LNA (Locked Nucleic Acids)

In some aspects, additional modifications at the 2' hydroxyl group include 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA).

In some aspects, a nucleotide analogue comprises a modified base such as, but not limited to, 5-propynyluridine, 5-propynylcytidine, 6-methyladenine, 6-methylguanine, N, N, -dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides (such as 7-deaza-adenosine, 6-azouridine, 6-azocytidine, or 6-azothymidine), 5-methyl-2-thiouridine, other thio bases (such as 2-thiouridine, 4-thiouridine, and 2-thiocytidine), dihydrouridine, pseudouridine, queuosine, archaeosine, naphthyl and substituted naphthyl groups, any O- and N-alkylated purines and pyrimidines (such as N6-methyladenosine, 5-methylcarbonylmethyluridine, uridine 5-oxyacetic acid, pyridine-4-one, or pyridine-2-one), phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. 5'-Vinylphosphonate modified nucleotides may also include those nucleotides that are modified with respect to the sugar moiety, as well as 5'-vinylphosphonate modified nucleotides having sugars or analogs thereof that are not ribosyl. For example, the sugar moieties, in some cases are or are based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some aspects, a 5'-vinylphosphonate modified nucleotide analogue further comprises a morpholino, a peptide nucleic acid (PNA), a methylphosphonate nucleotide, a thiolphosphonate nucleotide, a 2'-fluoro N3-P5'-phosphoramidite, or a 1', 5'-anhydrohexitol nucleic acid (HNA). Morpholinos or phosphorodiamidate morpholino oligomers (PMOs) comprise synthetic molecules whose structures mimic natural nucleic acid structure but deviate from the normal sugar and phosphate structures. In some instances, the five member ribose ring is substituted with a six member morpholino ring containing four carbons, one nitrogen, and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides. A non-limiting example of a 5'-vinylphosphonate modified morpholino oligonucleotide is illustrated below, wherein B is a heterocyclic base moiety.

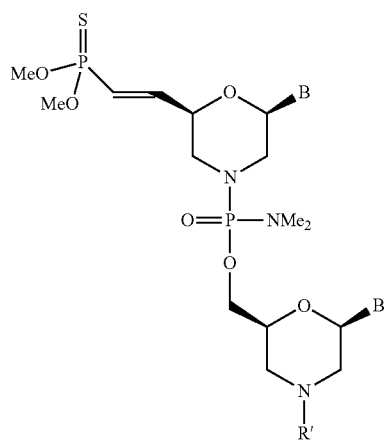

In some aspects, a 5'-vinylphosphonate modified morpholino or PMO described above is a PMO comprising a positive or cationic charge. In some instances, the PMO is PMOplus (Sarepta). PMOplus refers to phosphorodiamidate morpholino oligomers comprising any number of (1-piperazino)phosphinylideneoxy, (1-(4-(omega-guanidino-alkanoyl))-piperazino)phosphinylideneoxy linkages (e.g., as such those described in PCT Publication No. WO2008/036127. In some cases, the PMO is a PMO described in U.S. Pat. No. 7,943,762.

In some aspects, a morpholino or PMO described above is a PMO-X (Sarepta). In some cases, PMO-X refers to phosphorodiamidate morpholino oligomers comprising at least one linkage or at least one of the disclosed terminal modifications, such as those disclosed in PCT Publication No. WO2011/150408 and U.S. Publication No. 2012/0065169.

In some aspects, a morpholino or PMO described above is a PMO as described in Table 5 of U.S. Publication No. 2014/0296321.

Exemplary representations of the chemical structure of 5'-vinylphosphonate modified nucleic acids are illustrated below, wherein X is O or S; B is a heterocyclic base moiety; and J is an internucleotide linkage.

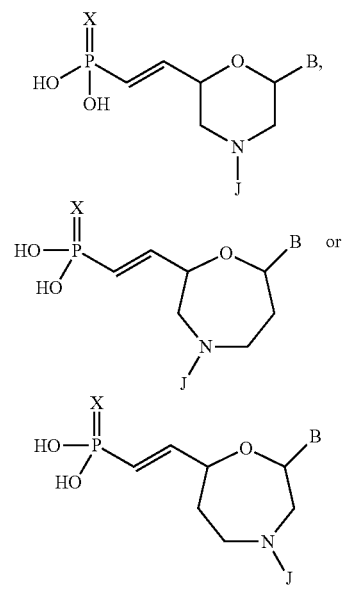

In some aspects, one or more modifications of the 5'-vinylphosphonate modified oligonucleotide optionally occur at the internucleotide linkage. In some instances, modified internucleotide linkages include, but is not limited to, phosphorothioates; phosphorodithioates; methylphosphonates; 5'-alkylenephosphonates; 5'-methylphosphonate; 3'-alkylene phosphonates; borontrifluoridates; borano phosphate esters and selenophosphates with 3'-5'linkages or 2'-5'linkages; phosphotriesters; thionoalkylphosphotriesters; hydrogen phosphonate linkages; alkyl phosphonates; alkylphosphonothioates; arylphosphonothioates; phosphoroselenoates; phosphorodiselenoates; phosphinates; phosphoramidates; 3'-alkylphosphoramidates; aminoalkylphosphoramidates; thionophosphoramidates; phosphoropiperazidates; phosphoroanilothioates; phosphoroanilidates; ketones; sulfones; sulfonamides; carbonates; carbamates; methylenehydrazos; methylenedimethylhydrazos; formacetals; thioformacetals; oximes; methyleneiminos; methylenemethyliminos; thioamidates; linkages with riboacetyl groups; aminoethyl glycine; silyl or siloxane linkages; alkyl or cycloalkyl linkages with or without heteroatoms of, for example, 1 to 10 carbons that are saturated or unsaturated and/or substituted and/or contain heteroatoms; linkages with morpholino structures, amides, or polyamides wherein the bases are attached to the aza nitrogens of the backbone directly or indirectly; and combinations thereof.

In some instances, the modification is a methyl or thiol modification such as methylphosphonate or thiolphosphonate modifications. An exemplary thiolphosphonate nucleotide (left), phosphorodithioates (center) and methylphosphonate nucleotide (right) are illustrated below.

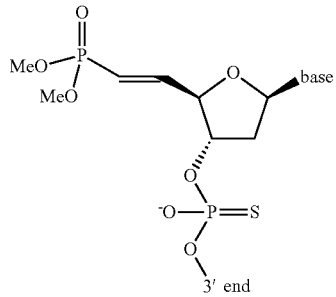

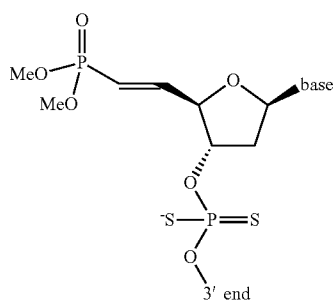

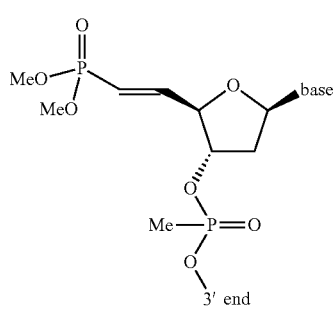

In some instances, a 5'-vinylphosphonate modified nucleotide includes, but is not limited to, phosphoramidites illustrated as:

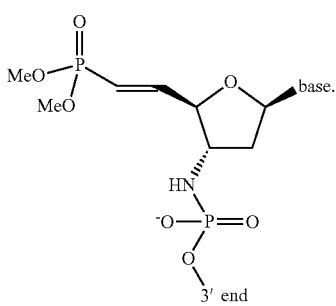

In some instances, the modified internucleotide linkage is a phosphorodiamidate linkage. A non-limiting example of a phosphorodiamidate linkage with a morpholino system is shown below.

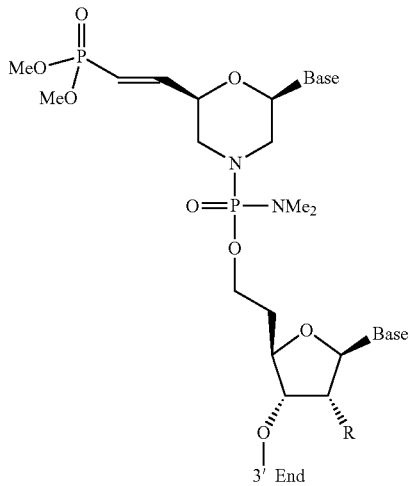

In some instances, the modified internucleotide linkage is a methylphosphonate linkage. A non-limiting example of a methylphosphonate linkage is shown below.

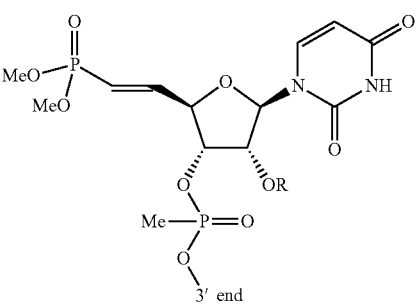

In some instances, the modified internucleotide linkage is an amide linkage. A non-limiting example of an amide linkage is shown below.

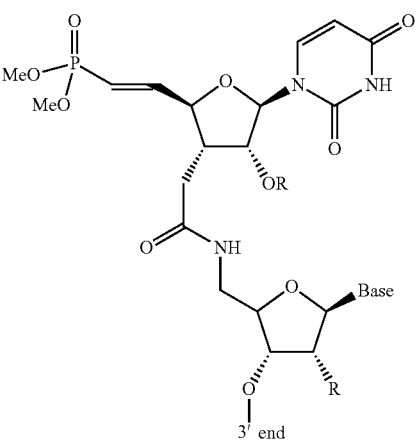

In some instances, a 5'-vinylphosphonate modified nucleotide includes, but is not limited to, the modified nucleic acid illustrated below.

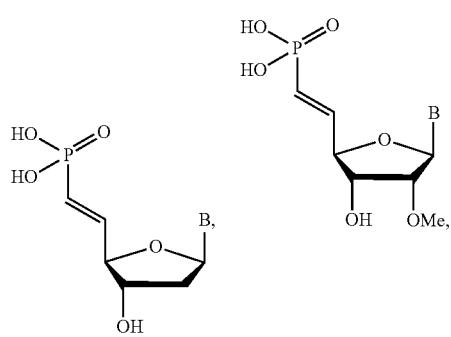
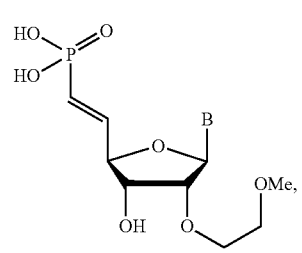
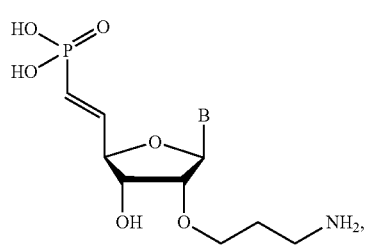
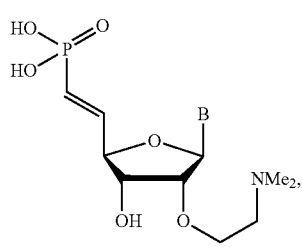
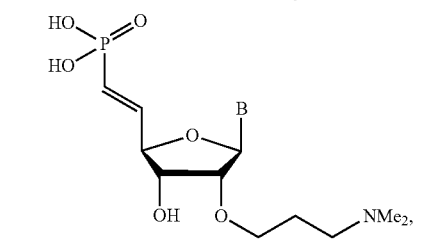
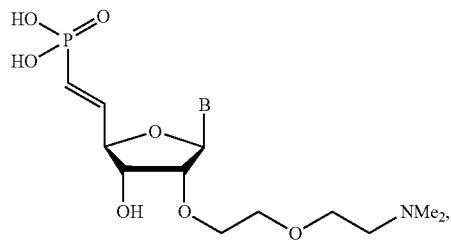
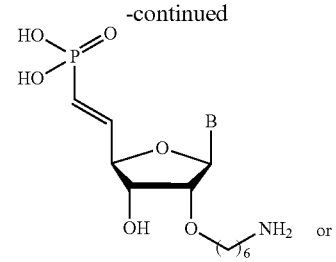
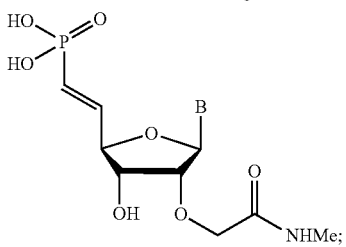
wherein B is a heterocyclic base moiety.
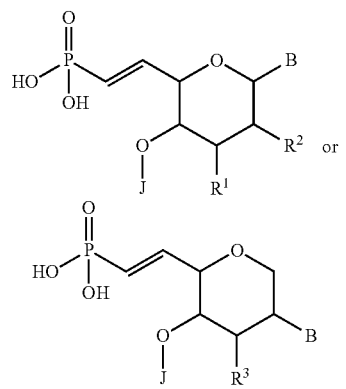
wherein B is a heterocyclic base moiety;
R4, and R5 are independently selected from hydrogen, halogen, alkyl or alkoxy; and
J is an internucleotide linking group linking to the adjacent nucleotide of the polynucleotide.
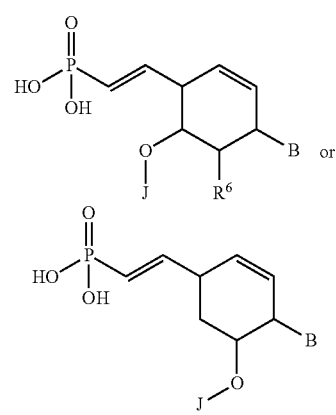
wherein B is a heterocyclic base moiety;
R6 is selected from hydrogen, halogen, alkyl or alkoxy; and J is an internucleotide linking group linking to the adjacent nucleotide of the polynucleotide.

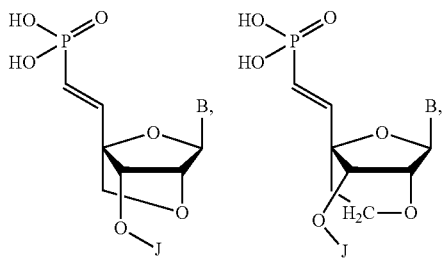

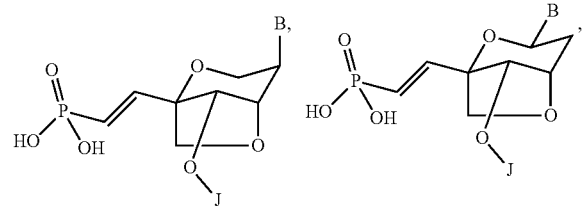

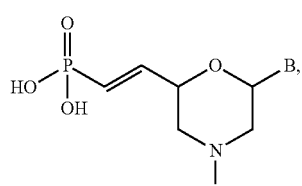

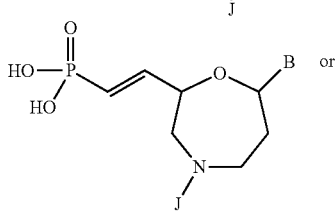

wherein B is a heterocyclic base moiety; and
J is an internucleotide linking group linking to the adjacent nucleotide of the polynucleotide.

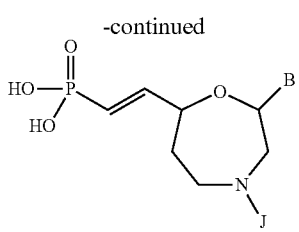

wherein B is a heterocyclic base moiety; and
J is an internucleotide linking group linking to the adjacent nucleotide of the polynucleotide.

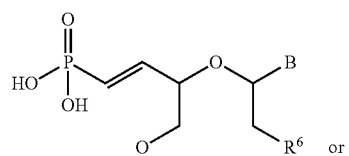

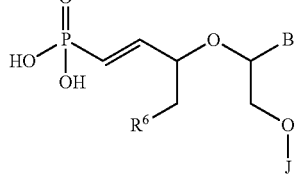

wherein B is a heterocyclic base moiety;
R6 is selected from hydrogen, halogen, alkyl or alkoxy; and
J is an internucleotide linking group linking to the adjacent nucleotide of the polynucleotide.

In some aspects, the PMO molecule of the PMO-antibody conjugate comprises a plurality of phosphorodiamidate morpholino oligomers or a plurality of peptide nucleic acid-modified non-natural nucleotides, and optionally comprises at least one inverted abasic moiety. In some instances, the PMO molecule comprises at least 6, 7, 8, 9, 10, 11, 12, 13, 14, 15, 16, 17, 18, 19, 20, or more phosphorodiamidate morpholino oligomer-modified non-natural nucleotides. In some instances, the PMO molecule comprises 100% phosphorodiamidate morpholino oligomer-modified non-natural nucleotides.

In some instances, the PMO molecule of the PMO-antibody conjugate comprises at least one of: from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification.

In some cases, one or more of the artificial nucleotide analogues described herein are resistant toward nucleases such as for example ribonuclease such as RNase H, deoxyribonuclease such as DNase, or exonuclease such as 5'-3' exonuclease and 3'-5' exonuclease when compared to natural polynucleic acid molecules. In some instances, artificial nucleotide analogues comprising 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribonuclease such as DNase, or exonuclease such as 5'-3' exonuclease and 3'-5' exonuclease. In some instances, 2'-O-methyl modified polynucleic acid molecule is nuclease resistant (e.g., RNase H, DNase, 5'-3' exonuclease or 3'-5' exonuclease resistance). In some instances, 2'-methoxyethyl (2'-O-MOE) modified polynucleic acid molecules are nuclease resistant (e.g., RNase H, DNase, 5'-3' exonuclease or 3'-5' exonuclease resistance). In some instances, 2'-O-aminopropyl modified polynucleic acid molecules are nuclease resistant (e.g., RNase H, DNase, 5'-3' exonuclease or 3'-5' exonuclease resistance). In some instances, 2'-deoxy modified polynucleic acid molecules are nuclease resistant (e.g., RNase H, DNase, 5'-3' exonuclease or 3'-5' exonuclease resistance). In some instances, 2'-deoxy-2'-fluoro modified polynucleic acid molecules are nuclease resistant (e.g., RNase H, DNase, 5'-3' exonuclease or 3'-5' exonuclease resistance). In some instances, 2'-O-aminopropyl (2'-O-AP) modified polynucleic acid molecules are nuclease resistant (e.g., RNase H, DNase, 5'-3' exonuclease or 3'-5' exonuclease resistance). In some instances, 2'-O-dimethylaminoethyl (2'-O-DMAOE) modified polynucleic acid molecules are nuclease resistant (e.g., RNase H, DNase, 5'-3' exonuclease or 3'-5' exonuclease resistance). In some instances, 2'-O-dimethylaminopropyl (2'-O-DMAP) modified polynucleic acid molecules are nuclease resistant (e.g., RNase H, DNase, 5'-3' exonuclease or 3'-5' exonuclease resistance). In some instances, 2'-O-dimethylaminoethyloxyethyl (2'-O-DMAEOE) modified polynucleic acid molecules are nuclease resistant (e.g., RNase H, DNase, 5'-3' exonuclease or 3'-5' exonuclease resistance). In some instances, 2'-O—N-methylacetamido (2'-O-NMA) modified polynucleic acid molecules are nuclease resistant (e.g., RNase H, DNase, 5'-3' exonuclease or 3'-5' exonuclease resistance). In some instances, LNA modified polynucleic acid molecules are nuclease resistant (e.g., RNase H, DNase, 5'-3' exonuclease or 3'-5' exonuclease resistance). In some instances, ENA modified polynucleic acid molecules are nuclease resistant (e.g., RNase H, DNase, 5'-3' exonuclease or 3'-5' exonuclease resistance). In some instances, HNA modified polynucleic acid molecules are nuclease resistant (e.g., RNase H, DNase, 5'-3' exonuclease or 3'-5' exonuclease resistance). In some instances, morpholinos are nuclease resistant (e.g., RNase H, DNase, 5'-3' exonuclease or 3'-5' exonuclease resistance). In some instances, PNA modified polynucleic acid molecules are resistant to nucleases (e.g., RNase H, DNase, 5'-3' exonuclease or 3'-5' exonuclease resistance). In some instances, methylphosphonate nucleotides modified polynucleic acid molecule are nuclease resistant (e.g., RNase H, DNase, 5'-3' exonuclease or 3'-5' exonuclease resistance). In some instances, thiolphosphonate nucleotide modified polynucleic acid molecules are nuclease resistant (e.g., RNase H, DNase, 5'-3' exonuclease or 3'-5' exonuclease resistance). In some instances, polynucleic acid molecules comprising 2'-fluoro N3-P5'-phosphoramidites are nuclease resistant (e.g., RNase H, DNase, 5'-3' exonuclease or 3'-5' exonuclease resistance). In some instances, the 5' conjugates described herein inhibit 5'-3' exonucleolytic cleavage. In some instances, the 3' conjugates described herein inhibit 3'-5' exonucleolytic cleavage.

Polynucleic Acid Molecule Synthesis

In some aspects, a polynucleic acid molecule described herein is constructed using chemical synthesis and/or enzymatic ligation reactions using procedures known in the art. For example, a polynucleic acid molecule is chemically synthesized using naturally occurring nucleotides or variously modified nucleotides designed to increase the biological stability of the molecules or to increase the physical stability of the duplex formed between the polynucleic acid molecule and target nucleic acids. Exemplary methods include those described in: U.S. Pat. Nos. 5,142,047; 5,185,444; 5,889,136; 6,008,400; and 6,111,086; PCT Publication No. WO2009099942; or European Publication No. 1579015. Additional exemplary methods include those described in: Griffey et al., "2'-O-aminopropyl ribonucleotides: a zwitterionic modification that enhances the exonuclease resistance and biological activity of antisense oligonucleotides," J. Med. Chem. 39(26):5100-5109 (1997)); Obika, et al. "Synthesis of 2'-0,4'-C-methyleneuridine and -cytidine. Novel bicyclic nucleosides having a fixed C3, -endo sugar puckering". Tetrahedron Letters 38 (50): 8735 (1997); Koizumi, M. "ENA oligonucleotides as therapeutics". Current opinion in molecular therapeutics 8 (2): 144-149 (2006); and Abramova et al., "Novel oligonucleotide analogues based on morpholino nucleoside subunits-antisense technologies: new chemical possibilities," Indian Journal of Chemistry 48B:1721-1726 (2009). Alternatively, the polynucleic acid molecule is produced biologically using an expression vector into which a polynucleic acid molecule has been subcloned in an antisense orientation (i.e., RNA transcribed from the inserted polynucleic acid molecule will be of an antisense orientation to a target polynucleic acid molecule of interest).

In some aspects, a polynucleic acid molecule is synthesized via a tandem synthesis methodology, wherein both strands are synthesized as a single contiguous oligonucleotide fragment or strand separated by a cleavable linker which is subsequently cleaved to provide separate fragments or strands that hybridize and permit purification of the duplex.

Additional modification methods for incorporating, for example, sugar, base and phosphate modifications include: Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Earnshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010. Such publications describe general methods and strategies to determine the location of incorporation of sugar, base and/or phosphate modifications and the like into nucleic acid molecules without modulating catalysis.

In some instances, while chemical modification of the polynucleic acid molecule internucleotide linkages with phosphorothioate, phosphorodithioate, and/or 5'-methylphosphonate linkages improves stability, excessive modifications sometimes cause toxicity or decreased activity. Therefore, when designing nucleic acid molecules, the amount of these internucleotide linkages in some cases is minimized. In such cases, the reduction in the concentration of these linkages lowers toxicity, increases efficacy and higher specificity of these molecules.

Antibody

In some aspects, the antibody or antigen binding fragment thereof comprises a humanized antibody or antigen binding fragment thereof, murine antibody or antigen binding fragment thereof, chimeric antibody or antigen binding fragment thereof, monoclonal antibody or antigen binding fragment thereof, monovalent Fab', divalent Fab2, F(ab)'3 fragments, single-chain variable fragment (scFv), bis-scFv, (scFv)2, diabody, minibody, nanobody, triabody, tetrabody, disulfide stabilized Fv protein (dsFv), single-domain antibody (sdAb), Ig NAR, camelid antibody or antigen binding fragment thereof, bispecific antibody or antigen binding fragment thereof, or a chemically modified derivative thereof.

In some instances, the antibody is an anti-transferrin receptor (anti-CD71) antibody or antigen binding fragment thereof. In some cases, the anti-transferrin receptor antibody is a humanized antibody or antigen binding fragment thereof. In other cases, the anti-transferrin receptor antibody is a chimeric antibody or antigen binding fragment thereof. In additional cases, the anti-transferrin receptor antibody is a monovalent, a divalent, or a multi-valent antibody or antigen binding fragment thereof. In some aspects, exemplary anti-transferrin receptor antibodies or antigen binding fragments thereof include MAB5746 from R&D Systems, AHP858 from Bio-Rad Laboratories, A80-128A from Bethyl Laboratories, Inc., and T2027 from MilliporeSigma. In some aspects, the anti-transferrin receptor antibody or antigen binding fragment thereof includes the antibodies disclosed in U.S. Pat. No. 10,913,800 or U.S. Pat. No. 11,028,179.

In some instances, the anti-transferrin receptor antibody comprises a variable heavy chain (VH) region and a variable light chain (VL) region, wherein the VH region comprises an HCDR1 sequence comprising or consisting of a sequence of SEQ ID NO: 17; an HCDR2 sequence comprising or consisting of a sequence of EINPIX1GRSNYAX2KFQG (SEQ ID NO: 12), wherein X1 is selected from N or Q and X2 is selected from Q or E; and an HCDR3 sequence comprising or consisting of a sequence of SEQ ID NO: 19.

In some aspects, the VH region of the anti-transferring antibody comprises HCDR1, HCDR2, and HCDR3 sequences selected from Table 3.

TABLE 3

| Name | HCDR1 | SEQ ID NO: | HCDR2 | SEQ ID NO: | HCDR3 | SEQ ID NO: |
|---|---|---|---|---|---|---|
| 13E4_VH1 | YTFTNYWMH | 17 | EINPIN-GRSNYAQKFQG | 18 | GTRAMHY | 19 |
| 13E4_VH2* | YTFTNYWMH | 17 | EINPINGRSNY-AEKFQG | 20 | GTRAMHY | 19 |
| 13E4_VH3 | YTFTNYWMH | 17 | EINPIQGRSNY-AEKFQG | 21 | GTRAMHY | 19 |

*13E4_VH2 shares the same HCDR1, HCDR2, and HCDR3 sequences with anti-transferrin receptor antibody 13E4_VH4

In some aspects, the VH region comprises an HCDR1 sequence comprising or consisting of a sequence of SEQ ID NO: 17; an HCDR2 sequence comprising or consisting of a sequence of SEQ ID NO: 18, 20, or 21; and an HCDR3 sequence comprising or consisting of a sequence of SEQ ID NO: 19. In some instances, the VH region comprises an HCDR1 sequence comprising or consisting of a sequence of SEQ ID NO: 17, an HCDR2 sequence comprising or consisting of a sequence of SEQ ID NO: 18, and an HCDR3 sequence comprising or consisting of a sequence of SEQ ID NO: 19. In some instances, the VH region comprises an HCDR1 sequence comprising or consisting of a sequence of SEQ ID NO: 17, an HCDR2 sequence comprising or consisting of a sequence of SEQ ID NO: 20, and an HCDR3 sequence comprising or consisting of a sequence of SEQ ID NO: 19. In some instances, the VH region comprises an HCDR1 sequence comprising or consisting of a sequence of SEQ ID NO: 17, an HCDR2 sequence comprising or consisting of a sequence of SEQ ID NO: 21, and an HCDR3 sequence comprising or consisting of a sequence of SEQ ID NO: 19.

In some aspects, the VL region of the anti-transferrin receptor antibody comprises an LCDR1 sequence comprising or consisting of a sequence of RTSENIYX3NLA (SEQ ID NO: 13), an LCDR2 sequence comprising or consisting of a sequence of AX4TNLAX5 (SEQ ID NO: 14), and an LCDR3 sequence comprising or consisting of a sequence of QHFWGTPLTX6 (SEQ ID NO: 15), wherein X3 is selected from N or S, X4 is selected from A or G, X5 is selected from D or E, and X6 is present or absent, and if present, is F.

In some aspects, the VL region of the anti-transferrin receptor antibody comprises LCDR1, LCDR2, and LCDR3 sequences selected from Table 4.

TABLE 4

| Name | LCDR1 | SEQ ID NO: | LCDR2 | SEQ ID NO: | LCDR3 | SEQ ID NO: |
|---|---|---|---|---|---|---|
| 13E4_VL1* | RTSENIYNNLA | 22 | AATNLAD | 23 | QHFWGTPLT | 24 |
| 13E4_VL3 | RTSENIYNNLA | 22 | AATNLAE | 25 | QHFWGTPLTF | 26 |
| 13E4_VL4 | RTSENIYSNLA | 27 | AGTNLAD | 28 | QHFWGTPLTF | 26 |

*13E4_VL1 shares the same LCDR1, LCDR2, and LCDR3 sequences with anti-transferrin receptor antibody 13E4_VL2

In some instances, the VL region comprises an LCDR1 sequence comprising or consisting of a sequence of SEQ ID NO: 13, an LCDR2 sequence comprising or consisting of a sequence of SEQ ID NO: 23, 25, or 28, and an LCDR3 sequence comprising or consisting of a sequence of SEQ ID NO: 24 or 26, wherein X3 is selected from N or S.

In some instances, the VL region comprises an LCDR1 sequence comprising or consisting of a sequence of SEQ ID NO: 22 or 27, an LCDR2 sequence comprising or consisting of a sequence of SEQ ID NO: 14, and an LCDR3 sequence comprising or consisting of a sequence of SEQ ID NO: 24 or 26, wherein X4 is selected from A or G, and X5 is selected from D or E.

In some instances, the VL region comprises an LCDR1 sequence comprising or consisting of a sequence of SEQ ID NO: 22 or 27, an LCDR2 sequence comprising or consisting of a sequence of SEQ ID NO: 23, 25, or 28, and an LCDR3 sequence comprising or consisting of a sequence of SEQ ID NO: 15, wherein X6 is present or absent, and if present, is F.

In some instances, the VL region comprises an LCDR1 sequence comprising or consisting of a sequence of SEQ ID NO: 22, an LCDR2 sequence comprising or consisting of a sequence of AATNLAX5 (SEQ ID NO: 16), and an LCDR3 sequence comprising or consisting of a sequence of SEQ ID NO: 15, wherein X5 is selected from D or E and X6 is present or absent, and if present, is F.

In some instances, the VL region comprises an LCDR1 sequence comprising or consisting of a sequence of SEQ ID NO: 22, an LCDR2 sequence comprising or consisting of a sequence of SEQ ID NO: 23, and an LCDR3 sequence comprising or consisting of a sequence of SEQ ID NO: 24.

In some instances, the VL region comprises an LCDR1 sequence comprising or consisting of a sequence of SEQ ID NO: 22, an LCDR2 sequence comprising or consisting of a sequence of SEQ ID NO: 25, and an LCDR3 sequence comprising or consisting of a sequence of SEQ ID NO: 26.

In some instances, the VL region comprises an LCDR1 sequence comprising or consisting of a sequence of SEQ ID NO: 27, an LCDR2 sequence comprising or consisting of a sequence of SEQ ID NO: 28, and an LCDR3 sequence comprising or consisting of a sequence of SEQ ID NO: 26.

In some aspects, the anti-transferrin receptor antibody comprises a VH region and a VL region, wherein the VH region comprises an HCDR1 sequence comprising or consisting of a sequence of SEQ ID NO: 17; an HCDR2 sequence comprising or consisting of a sequence of SEQ ID NO: 12, wherein X1 is selected from N or Q and X2 is selected from Q or E; and an HCDR3 sequence comprising or consisting of a sequence of SEQ ID NO: 19; and the VL region comprises an LCDR1 sequence comprising or consisting of a sequence of SEQ ID NO: 13, an LCDR2 sequence comprising or consisting of a sequence of SEQ ID NO: 14, and an LCDR3 sequence comprising or consisting of a sequence of SEQ ID NO: 15, wherein X3 is selected from N or S, X4 is selected from A or G, X5 is selected from D or E, and X6 is present or absent, and if present, is F.

In some instances, the anti-transferrin receptor antibody comprises a VH region and a VL region, wherein the VH region comprises an HCDR1 sequence comprising or consisting of a sequence of SEQ ID NO: 17; an HCDR2 sequence comprising or consisting of a sequence of SEQ ID NO: 12, wherein X1 is selected from N or Q and X2 is selected from Q or E; and an HCDR3 sequence comprising or consisting of a sequence of SEQ ID NO: 19; and the VL region comprises an LCDR1 sequence comprising or consisting of a sequence of SEQ ID NO: 13, an LCDR2 sequence comprising or consisting of a sequence of SEQ ID NO: 23, 25, or 28, and an LCDR3 sequence comprising or consisting of a sequence of SEQ ID NO: 24 or 26, wherein X3 is selected from N or S.

In some instances, the anti-transferrin receptor antibody comprises a VH region and a VL region, wherein the VH region comprises an HCDR1 sequence comprising or consisting of a sequence of SEQ ID NO: 17; an HCDR2 sequence comprising or consisting of a sequence of SEQ ID NO: 12, wherein X1 is selected from N or Q and X2 is selected from Q or E; and an HCDR3 sequence comprising or consisting of a sequence of SEQ ID NO: 19; and the VL region comprises an LCDR1 sequence comprising or consisting of a sequence of SEQ ID NO: 22 or 27, an LCDR2 sequence comprising or consisting of a sequence of SEQ ID NO: 14, and an LCDR3 sequence comprising or consisting of a sequence of SEQ ID NO: 24 or 26, wherein X4 is selected from A or G, and X5 is selected from D or E.

In some instances, the anti-transferrin receptor antibody comprises a VH region and a VL region, wherein the VH region comprises an HCDR1 sequence comprising or consisting of a sequence of SEQ ID NO: 17; an HCDR2 sequence comprising or consisting of a sequence of SEQ ID NO: 12, wherein X1 is selected from N or Q and X2 is selected from Q or E; and an HCDR3 sequence comprising or consisting of a sequence of SEQ ID NO: 19; and the VL region comprises an LCDR1 sequence comprising or consisting of a sequence of SEQ ID NO: 22 or 27, an LCDR2 sequence comprising or consisting of a sequence of SEQ ID NO: 23, 25, or 28, and an LCDR3 sequence comprising or consisting of a sequence of SEQ ID NO: 15, wherein X6 is present or absent, and if present, is F.

In some instances, the anti-transferrin receptor antibody comprises a VH region and a VL region, wherein the VH region comprises an HCDR1 sequence comprising or consisting of a sequence of SEQ ID NO: 17; an HCDR2 sequence comprising or consisting of a sequence of SEQ ID NO: 12, wherein X1 is selected from N or Q and X2 is selected from Q or E; and an HCDR3 sequence comprising or consisting of a sequence of SEQ ID NO: 19; and the VL region comprises an LCDR1 sequence comprising or consisting of a sequence of SEQ ID NO: 22, an LCDR2 sequence comprising or consisting of a sequence of SEQ ID NO: 16, and an LCDR3 sequence comprising or consisting of a sequence of SEQ ID NO: 15, wherein X5 is selected from D or E and X6 is present or absent, and if present, is F.

In some instances, the anti-transferrin receptor antibody comprises a VH region and a VL region, wherein the VH region comprises an HCDR1 sequence comprising or consisting of a sequence of SEQ ID NO: 17; an HCDR2 sequence comprising or consisting of a sequence of SEQ ID NO: 12, wherein X1 is selected from N or Q and X2 is selected from Q or E; and an HCDR3 sequence comprising or consisting of a sequence of SEQ ID NO: 19; and the VL region comprises an LCDR1 sequence comprising or consisting of a sequence of SEQ ID NO: 22, an LCDR2 sequence comprising or consisting of a sequence of SEQ ID NO: 23, and an LCDR3 sequence comprising or consisting of a sequence of SEQ ID NO: 24.

In some instances, the anti-transferrin receptor antibody comprises a VH region and a VL region, wherein the VH region comprises an HCDR1 sequence comprising or consisting of a sequence of SEQ ID NO: 17; an HCDR2 sequence comprising or consisting of a sequence of SEQ ID NO: 12, wherein X1 is selected from N or Q and X2 is selected from Q or E; and an HCDR3 sequence comprising or consisting of a sequence of SEQ ID NO: 19; and the VL region comprises an LCDR1 sequence comprising or consisting of a sequence of SEQ ID NO: 22, an LCDR2 sequence comprising or consisting of a sequence of SEQ ID NO: 25, and an LCDR3 sequence comprising or consisting of a sequence of SEQ ID NO: 26.

In some instances, the anti-transferrin receptor antibody comprises a VH region and a VL region, wherein the VH region comprises an HCDR1 sequence comprising or consisting of a sequence of SEQ ID NO: 17; an HCDR2 sequence comprising or consisting of a sequence of SEQ ID NO: 12, wherein X1 is selected from N or Q and X2 is selected from Q or E; and an HCDR3 sequence comprising or consisting of a sequence of SEQ ID NO: 19; and the VL region comprises an LCDR1 sequence comprising or consisting of a sequence of SEQ ID NO: 27, an LCDR2 sequence comprising or consisting of a sequence of SEQ ID NO: 28, and an LCDR3 sequence comprising or consisting of a sequence of SEQ ID NO: 26.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 18, and an HCDR3 sequence comprising or consisting of a sequence of SEQ ID NO: 19; and the VL region comprises an LCDR1 sequence comprising or consisting of a sequence of SEQ ID NO: 13, an LCDR2 sequence comprising or consisting of a sequence of SEQ ID NO: 23, 25, or 28, and an LCDR3 sequence comprising or consisting of a sequence of SEQ ID NO: 24 or 26, wherein X3 is selected from N or S.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 18, and an HCDR3 sequence comprising or consisting of a sequence of SEQ ID NO: 19; and the VL region comprises an LCDR1 sequence comprising or consisting of a sequence of SEQ ID NO: 22 or 27, an LCDR2 sequence comprising or consisting of a sequence of SEQ ID NO: 14, and an LCDR3 sequence comprising or consisting of a sequence of SEQ ID NO: 24 or 26, wherein X4 is selected from A or G, and X5 is selected from D or E.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 18, and an HCDR3 sequence comprising or consisting of a sequence of SEQ ID NO: 19; and the VL region comprises an LCDR1 sequence comprising or consisting of a sequence of SEQ ID NO: 22 or 27, an LCDR2 sequence comprising or consisting of a sequence of SEQ ID NO: 23, 25, or 28, and LCDR3 sequence comprising or consisting of a sequence of SEQ ID NO: 15, wherein X6 is present or absent, and if present, is F.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 18, and an HCDR3 sequence comprising or consisting of a sequence of SEQ ID NO: 19; and the VL region comprises an LCDR1 sequence comprising or consisting of a sequence of SEQ ID NO: 22, an LCDR2 sequence comprising or consisting of a sequence of SEQ ID NO: 16, and an LCDR3 sequence comprising or consisting of a sequence of SEQ ID NO: 15, wherein X5 is selected from D or E and X6 is present or absent, and if present, is F.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 18, and an HCDR3 sequence comprising or consisting of a sequence of SEQ ID NO: 19; and the VL region comprises an LCDR1 sequence comprising or consisting of a sequence of SEQ ID NO: 22, an LCDR2 sequence comprising or consisting of a sequence of SEQ ID NO: 23, and an LCDR3 sequence comprising or consisting of a sequence of SEQ ID NO: 24.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 18, and an HCDR3 sequence comprising or consisting of a sequence of SEQ ID NO: 19; and the VL region comprises an LCDR1 sequence comprising or consisting of a sequence of SEQ ID NO: 22, an LCDR2 sequence comprising or consisting of a sequence of SEQ ID NO: 21, and an LCDR3 sequence comprising or consisting of a sequence of SEQ ID NO: 26.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 18, and an HCDR3 sequence comprising or consisting of a sequence of SEQ ID NO: 19; and the VL region comprises an LCDR1 sequence comprising or consisting of a sequence of SEQ ID NO: 27, an LCDR2 sequence comprising or consisting of a sequence of SEQ ID NO: 28, and an LCDR3 sequence comprising or consisting of a sequence of SEQ ID NO: 26.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 20, and an HCDR3 sequence comprising or consisting of a sequence of SEQ ID NO: 19; and the VL region comprises an LCDR1 sequence comprising or consisting of a sequence of SEQ ID NO: 13, an LCDR2 sequence comprising or consisting of a sequence of SEQ ID NO: 23, 25, or 28, and an LCDR3 sequence comprising or consisting of a sequence of SEQ ID NO: 24 or 26, wherein X3 is selected from N or S.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 20, and an HCDR3 sequence comprising or consisting of a sequence of SEQ ID NO: 19; and the VL region comprises an LCDR1 sequence comprising or consisting of a sequence of SEQ ID NO: 22 or 27, an LCDR2 sequence comprising or consisting of a sequence of SEQ ID NO: 14, and an LCDR3 sequence comprising or consisting of a sequence of SEQ ID NO: 24 or 26, wherein X4 is selected from A or G, and X5 is selected from D or E.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 20, and an HCDR3 sequence comprising or consisting of a sequence of SEQ ID NO: 19; and the VL region comprises an LCDR1 sequence comprising or consisting of a sequence of SEQ ID NO: 22 or 27, an LCDR2 sequence comprising or consisting of a sequence of SEQ ID NO: 23, 25 or 28, and an LCDR3 sequence comprising or consisting of a sequence of SEQ ID NO: 15, wherein X6 is present or absent, and if present, is F.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 20, and an HCDR3 sequence comprising or consisting of a sequence of SEQ ID NO: 19; and the VL region comprises an LCDR1 sequence comprising or consisting of a sequence of SEQ ID NO: 22, an LCDR2 sequence comprising or consisting of a sequence of SEQ ID NO: 16, and an LCDR3 sequence comprising or consisting of a sequence of SEQ ID NO: 15, wherein X5 is selected from D or E and X6 is present or absent, and if present, is F.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 20, and an HCDR3 sequence comprising or consisting of a sequence of SEQ ID NO: 19; and the VL region comprises an LCDR1 sequence comprising or consisting of a sequence of SEQ ID NO: 22, an LCDR2 sequence comprising or consisting of a sequence of SEQ ID NO: 23, and an LCDR3 sequence comprising or consisting of a sequence of SEQ ID NO: 24.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 20, and an HCDR3 sequence comprising or consisting of a sequence of SEQ ID NO: 19; and the VL region comprises an LCDR1 sequence comprising or consisting of a sequence of SEQ ID NO: 22, an LCDR2 sequence comprising or consisting of a sequence of SEQ ID NO: 25, and an LCDR3 sequence comprising or consisting of a sequence of SEQ ID NO:26.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 20, and an HCDR3 sequence comprising or consisting of a sequence of SEQ ID NO: 19; and the VL region comprises an LCDR1 sequence comprising or consisting of a sequence of SEQ ID NO: 27, an LCDR2 sequence comprising or consisting of a sequence of SEQ ID NO: 28, and an LCDR3 sequence comprising or consisting of a sequence of SEQ ID NO: 26.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 21, and an HCDR3 sequence comprising or consisting of a sequence of SEQ ID NO: 19; and the VL region comprises an LCDR1 sequence comprising or consisting of a sequence of SEQ ID NO: 13, an LCDR2 sequence comprising or consisting of a sequence of SEQ ID NO: 23, 25, or 28, and an LCDR3 sequence comprising or consisting of a sequence of SEQ ID NO: 24 or 26, wherein X3 is selected from N or S.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 21, and an HCDR3 sequence comprising or consisting of a sequence of SEQ ID NO: 19; and the VL region comprises an LCDR1 sequence comprising or consisting of a sequence of SEQ ID NO: 22 or 27, an LCDR2 sequence comprising or consisting of a sequence of SEQ ID NO: 14, and an LCDR3 sequence comprising or consisting of a sequence of SEQ ID NO: 24 or 26, wherein X4 is selected from A or G, and X5 is selected from D or E.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 21, and an HCDR3 sequence comprising or consisting of a sequence of SEQ ID NO: 19; and the VL region comprises an LCDR1 sequence comprising or consisting of a sequence of SEQ ID NO: 22 or 27, an LCDR2 sequence comprising or consisting of a sequence of SEQ ID NO: 23, 25, or 28, and LCDR3 sequence comprising or consisting of a sequence of SEQ ID NO: 15, wherein X6 is present or absent, and if present, is F.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 21, and an HCDR3 sequence comprising or consisting of a sequence of SEQ ID NO: 19, and the VL region comprises an LCDR1 sequence comprising or consisting of a sequence of SEQ ID NO: 22, an LCDR2 sequence comprising or consisting of a sequence of SEQ ID NO: 16, and an LCDR3 sequence comprising or consisting of a sequence of SEQ ID NO: 15, wherein X5 is selected from D or E and X6 is present or absent, and if present, is F.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 21, and an HCDR3 sequence comprising or consisting of a sequence of SEQ ID NO: 19; and the VL region comprises an LCDR1 sequence comprising or consisting of a sequence of SEQ ID NO: 22, an LCDR2 sequence comprising or consisting of a sequence of SEQ ID NO: 23, and an LCDR3 sequence comprising or consisting of a sequence of SEQ ID NO: 24.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 21, and an HCDR3 sequence comprising or consisting of a sequence of SEQ ID NO: 19; and the VL region comprises an LCDR1 sequence comprising or consisting of a sequence of SEQ ID NO: 22, an LCDR2 sequence comprising or consisting of a sequence of SEQ ID NO: 25, and an LCDR3 sequence comprising or consisting of a sequence of SEQ ID NO: 26.

In some instances, the anti-transferrin receptor antibody comprises a VH region and a VL region, in which the VH region comprises an HCDR1 sequence comprising or consisting of a sequence of SEQ ID NO: 17, an HCDR2 sequence comprising or consisting of a sequence of SEQ ID NO: 21, and an HCDR3 sequence comprising or consisting of a sequence of SEQ ID NO: 19; and the VL region comprises an LCDR1 sequence comprising or consisting of a sequence of SEQ ID NO: 27, an LCDR2 sequence comprising or consisting of a sequence of SEQ ID NO: 28, and an LCDR3 sequence comprising or consisting of a sequence of SEQ ID NO: 26.

In some aspects, the anti-transferrin receptor antibody comprises a VH region and a VL region in which the sequence of the VH region comprises or consists of a sequence with about 80%, about 85%, about 90%, about 95%, about 96%, about 97%, about 98%, about 99%, or about 100% sequence identity to a sequence selected from SEQ ID NOs: 29-33 and the sequence of the VL region comprises or consisting of a sequence with about 80%, about 85%, about 90%, about 95%, about 96%, about 97%, about 98%, about 99%, or about 100% sequence identity to a sequence selected from SEQ ID NOs: 34-38. In some aspects, the anti-transferrin receptor antibody comprises a VH region and a VL region in which the sequence of the VH region comprises or consists of a sequence with at least 80%, at least 85%, at least 90%, at least 95%, at least 96%, at least 97%, at least 98%, at least 99%, or 100% sequence identity to a sequence selected from a sequence of SEQ ID NOs: 29-33 and the sequence of the VL region comprises or consists of a sequence with at least 80%, at least 85%, at least 90%, at least 95%, at least 96%, at least 97%, at least 98%, at least 99%, or 100% sequence identity to a sequence selected from a sequence of SEQ ID NOs: 34-38. In some aspects, the anti-transferrin receptor antibody comprises a VH region and a VL region in which the sequence of the VH region comprises or consists of a sequence selected from a sequence of SEQ ID NOs: 29-33 and the sequence of the VL region comprises or consists of a sequence selected from a sequence of SEQ ID NOs: 34-38.

In some aspects, the VH region comprises or consists of a sequence selected from SEQ ID NOs: 29-33 (Table 5) and the VL region comprises or consists of a sequence selected from SEQ ID NOs: 34-38 (Table 6). The underlined regions in Table 5 and Table 6 denote the respective CDR1, CDR2, or CDR3 sequence.

TABLE 5

| NAME | VH SEQUENCE | SEQ ID NO: |
|---|---|---|
| 13E4_VH1 | QVQLVQSGAEVKKPGASVKVSCKASGYTFTNYWMHWVRQAPGQGLEWMGEINPINGRSNYAQKFQGRVTLTVDTSISTAYMELSRLRSDDTAVYYCARGTRAMHYWGQGTLVTVSS | 29 |
| 13E4_VH2 | QVQLVQSGAEVKKPGASVKVSCKASGYTFTNYWMHWVRQAPGQGLEWIGEINPINGRSNYAEKFQGRVTLTVDTSSSTAYMELSRLRSDDTAVYYCARGTRAMHYWGQGTLVTVSS | 30 |
| 13E4_VH3 | QVQLVQSGAEVKKPGASVKVSCKASGYTFTNYWMHWVRQAPGQGLEWMGEINPIQGRSNYAEKFQGRVTLTVDTSSSTAYMELSSLRSEDTATYYCARGTRAMHYWGQGTLVTVSS | 31 |
| 13E4_VH4 | QVQLVQSGAEVKKPGASVKVSCKASGYTFTNYWMHWVRQAPGQGLEWMGEINPINGRSNYAEKFQGRVTLTVDTSSSTAYMELSSLRSEDTATYYCARGTRAMHYWGQGTLVTVSS | 32 |
| 13E4_VH | QVQLQQPGAELVKPGASVKLSCKASGYTFTNYWMHWVKQRPGQGLEWIGEINPINGRSNYGERFKTKATLTVDKSSSTAYMQLSSLTSEDSAVYYCARGTRAMHYWGQGTSVTVSS | 33 |

TABLE 6

| NAME | VL SEQUENCE | SEQ ID NO: |
|---|---|---|
| 13E4_VL1 | DIQMTQSPSSLSASVGDRVTITCRTSENIYNNLAWYQQKPGKSPKLLIYAATNLADGVPSRFSGSGSGTDYTLTISSLQPEDFATYYCQHFWGTPLTFGGGTKVEIK | 34 |
| 13E4_VL2 | DIQMTQSPSSLSASVGDRVTITCRTSENIYNNLAWYQQKPGKAPKLLIYAATNLADGVPSRFSGSGSGTDYTLTISSLQPEDFATYYCQHFWGTPLTFGGGTKVEIK | 35 |
| 13E4_VL3 | DIQMTQSPSSLSASVGDRVTITCRTSENIYNNLAWYQQKPGKAPKLLIYAATNLAEGVPSRFSGSGSGTDYTLTISSLQPEDFATYYCQHFWGTPLTFGGGTKVEIK | 36 |
| 13E4_VL4 | DIQMTQSPSSLSASVGDRVTITCRTSENIYSNLAWYQQKPGKAPKLLIYAGTNLADGVPSRFSGSGSGTDYTLTISSLQPEDFANYYCQHFWGTPLTFGGGTKVEIK | 37 |
| 13E4_VL | DIQMTQSPASLSVSVGETVTITCRTSENIYNNLAWYQQKQGKSPQLLVYAATNLADGVPSRFSGSGSGTQYSLKINSLQSEDFGNYYCQHFWGTPLTFGAGTKLELK | 38 |

In some aspects, the anti-transferrin receptor antibody comprises a VH region and a VL region as illustrated in Table 7.

TABLE 7

|  | 13E4_VH1 (SEQ ID NO: 29) | 13E4_VH2 (SEQ ID NO: 30) | 13E4_VH3 (SEQ ID NO: 31) | 13E4_VH4 (SEQ ID NO: 32) |
|---|---|---|---|---|
| 13E4_VL1 (SEQ ID NO: 34) | SEQ ID NO: 29 + SEQ ID NO: 34 | SEQ ID NO: 30 + SEQ ID NO: 34 | SEQ ID NO: 31 + SEQ ID NO: 34 | SEQ ID NO: 32 + SEQ ID NO: 34 |
| 13E4_VL2 (SEQ ID NO: 35) | SEQ ID NO: 29 + SEQ ID NO: 35 | SEQ ID NO: 30 + SEQ ID NO: 35 | SEQ ID NO: 31 + SEQ ID NO: 35 | SEQ ID NO: 32 + SEQ ID NO: 35 |
| 13E4_VL3 (SEQ ID NO: 36) | SEQ ID NO: 29 + SEQ ID NO: 36 | SEQ ID NO: 30 + SEQ ID NO: 36 | SEQ ID NO: 31 + SEQ ID NO: 36 | SEQ ID NO: 32 + SEQ ID NO: 36 |
| 13E4_VL4 (SEQ ID NO: 37) | SEQ ID NO: 29 + SEQ ID NO: 37 | SEQ ID NO: 30 + SEQ ID NO: 37 | SEQ ID NO: 31 + SEQ ID NO: 37 | SEQ ID NO: 32 + SEQ ID NO: 37 |

In some aspects, an anti-transferrin receptor antibody described herein comprises an IgG framework, an IgA framework, an IgE framework, or an IgM framework. In some instances, the anti-transferrin receptor antibody comprises an IgG framework (e.g., IgG1, IgG2, IgG3, or IgG4). In some cases, the anti-transferrin receptor antibody comprises an IgG1 framework. In some cases, the anti-transferrin receptor antibody comprises an IgG2 (e.g., an IgG2a or IgG2b) framework. In some cases, the anti-transferrin receptor antibody comprises an IgG2a framework. In some cases, the anti-transferrin receptor antibody comprises an IgG2b framework. In some cases, the anti-transferrin receptor antibody comprises an IgG3 framework. In some cases, the anti-transferrin receptor antibody comprises an IgG4 framework.

In some cases, an anti-transferrin receptor antibody comprises one or more mutations in a framework region, e.g., in the CH1 domain, CH2 domain, CH3 domain, hinge region, or a combination thereof. In some instances, the one or more mutations are to stabilize the antibody and/or to increase half-life. In some instances, the one or more mutations are to modulate Fc receptor interactions, to reduce or eliminate Fc effector functions such as FcyR, antibody-dependent cell-mediated cytotoxicity (ADCC), or complement-dependent cytotoxicity (CDC). In additional instances, the one or more mutations are to modulate glycosylation.

In some aspects, the one or more mutations are located in the Fc region. In some instances, the Fc region comprises a mutation at residue position L234, L235, or a combination thereof. In some instances, the mutations comprise L234 and L235. In some instances, the mutations comprise L234A and L235A. In some cases, the residue positions are in reference to IgG1.

In some instances, the Fc region comprises a mutation at residue position L234, L235, D265, N21, K46, L52, or P53, or a combination thereof. In some instances, the mutations comprise L234 and L235 in combination with a mutation at residue position K46, L52, or P53. In some cases, the Fc region comprises mutations at L234, L235, and K46. In some cases, the Fc region comprises mutations at L234, L235, and L52. In some cases, the Fc region comprises mutations at L234, L235, and P53. In some cases, the Fc region comprises mutations at D265 and N21. In some cases, the residue position is in reference to IgG1.

In some instances, the Fc region comprises L234A, L235A, D265A, N21G, K46G, L52R, or P53G, or a combination thereof. In some instances, the Fc region comprises L234A and L235A in combination with K46G, L52R, or P53G. In some cases, the Fc region comprises L234A, L235A, and K46G. In some cases, the Fc region comprises L234A, L235A, and L52R. In some cases, the Fc region comprises L234A, L235A, and P53G. In some cases, the Fc region comprises D265A and N21G. In some cases, the residue position is in reference to IgG1.

In some instances, the Fc region comprises a mutation at residue position L235, L236, D265, N21, K46, L52, or P53, or a combination of the mutations. In some instances, the Fc region comprises mutations at L235 and L236. In some instances, the Fc region comprises mutations at L235 and L236 in combination with a mutation at residue position K46, L52, or P53. In some cases, the Fc region comprises mutations at L235, L236, and K46. In some cases, the Fc region comprises mutations at L235, L236, and L52. In some cases, the Fc region comprises mutations at L235, L236, and P53. In some cases, the Fc region comprises mutations at D265 and N21. In some cases, the residue position is in reference to IgG2b.

In some aspects, the Fc region comprises L235A, L236A, D265A, N21G, K46G, L52R, or P53G, or a combination thereof. In some instances, the Fc region comprises L235A and L236A. In some instances, the Fc region comprises L235A and L236A in combination with K46G, L52R, or P53G. In some cases, the Fc region comprises L235A, L236A, and K46G. In some cases, the Fc region comprises L235A, L236A, and L52R. In some cases, the Fc region comprises L235A, L236A, and P53G. In some cases, the Fc region comprises D265A and N21G. In some cases, the residue position is in reference to IgG2b.

In some aspects, the Fc region comprises a mutation at residue position L233, L234, D264, N20, K45, L51, or P52, wherein the residues correspond to positions 233, 234, 264, 20, 45, 51, and 52 of SEQ ID NO: 39. In some instances, the Fc region comprises mutations at L233 and L234. In some instances, the Fc region comprises mutations at L233 and L234 in combination with a mutation at residue position K45, L51, or P52. In some cases, the Fc region comprises mutations at L233, L234, and K45. In some cases, the Fc region comprises mutations at L233, L234, and L51. In some cases, the Fc region comprises mutations at L233, L234, and K45. In some cases, the Fc region comprises mutations at L233, L234, and P52. In some instances, the Fc region comprises mutations at D264 and N20. In some cases, equivalent positions to residue L233, L234, D264, N20, K45, L51, or P52 in an IgG1, IgG2, IgG3, or IgG4 framework are contemplated. In some cases, mutations to a residue that corresponds to residue L233, L234, D264, N20, K45, L51, or P52 of SEQ ID NO: 39 in an IgG1, IgG2, or IgG4 framework are also contemplated.

In some instances, the Fc region comprises L233A, L234A, D264A, N20G, K45G, L51R, or P52G, wherein the residues correspond to positions 233, 234, 264, 20, 45, 51, and 52 of SEQ ID NO: 39. In some instances, the Fc region comprises L233A and L234A. In some instances, the Fc region comprises L233A and L234A in combination with K45G, L51R, or P52G. In some cases, the Fc region comprises L233A, L234A, and K45G. In some cases, the Fc region comprises L233A, L234A, and L51R. In some cases, the Fc region comprises L233A, L234A, and K45G. In some cases, the Fc region comprises L233A, L234A, and P52G. In some instances, the Fc region comprises D264A and N20G.

In some aspects, the human IgG constant region is modified to alter antibody-dependent cellular cytotoxicity (ADCC) and/or complement-dependent cytotoxicity (CDC), e.g., with an amino acid modification described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1): 1-11.

In some aspects, an anti-transferrin receptor antibody described herein is a full-length antibody, comprising a heavy chain (HC) and a light chain (LC). In some cases, the heavy chain (HC) comprises a sequence selected from Table 8. In some cases, the light chain (LC) comprises a sequence selected from Table 9. The underlined region denotes the respective CDRs.

TABLE 8

| NAME | HC SEQUENCE | SEQ ID NO: |
|---|---|---|
| 13E4_VH1 | QVQLVQSGAEVKKPGASVKVSCKASGYTFTNYWMHWVRQAPG QGLEWMGEINPINGRSNYAQKFQGRVTLTVDTSISTAYMELSRL RSDDTAVYYCARGTRAMHYWGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKRVEPKS CDKTHTCPPCPAPELLGGPSVFLFPPKPKDTLMISRTPEVTCVVV DVSHEDPEVKFNWYVDGVEVHNAKTKPREEQYNSTYRVVSVLT VLHQDWLNGKEYKCKVSNKALPAPIEKTISKAKGQPREPQVYTL PPSREEMTKNQVSLTCLVKGFYPSDIAVEWESNGQPENNYKTTP PVLDSDGSFFLYSKLTVDKSRWQQGNVFSCSVMHEALHNHYTQ KSLSLSPG | 39 |
| 13E4_VH1_a | QVQLVQSGAEVKKPGASVKVSCKASGYTFTNYWMHWVRQAPG QGLEWMGEINPINGRSNYAQKFQGRVTLTVDTSISTAYMELSRL RSDDTAVYYCARGTRAMHYWGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKRVEPKS CDKTHTCPPCPAPEAAGGPSVFLFPPKPKDTLMISRTPEVTCVVV DVSHEDPEVKFNWYVDGVEVHNAKTKPREEQYNSTYRVVSVLT VLHQDWLNGKEYKCKVSNKALPAPIEKTISKAKGQPREPQVYTL PPSREEMTKNQVSLTCLVKGFYPSDIAVEWESNGQPENNYKTTP PVLDSDGSFFLYSKLTVDKSRWQQGNVFSCSVMHEALHNHYTQ KSLSLSPG | 40 |
| 13E4_VH1_b | QVQLVQSGAEVKKPGASVKVSCKASGYTFTNYWMHWVRQAPG QGLEWMGEINPINGRSNYAQKFQGRVTLTVDTSISTAYMELSRL RSDDTAVYYCARGTRAMHYWGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKRVEPKS CDKTHTCPPCPAPEAAGGPSVFLFPPKPKDTLMISRTPEVTCVVV DVSHEDPEVKFNWYVDGVEVHNAKTKPREEQYNSTYRVVSVLT VLHQDWLNGKEYKCGVSNKALPAPIEKTISKAKGQPREPQVYTL PPSREEMTKNQVSLTCLVKGFYPSDIAVEWESNGQPENNYKTTP PVLDSDGSFFLYSKLTVDKSRWQQGNVFSCSVMHEALHNHYTQ KSLSLSPG | 41 |
| 13E4_VH1_c | QVQLVQSGAEVKKPGASVKVSCKASGYTFTNYWMHWVRQAPG QGLEWMGEINPINGRSNYAQKFQGRVTLTVDTSISTAYMELSRL RSDDTAVYYCARGTRAMHYWGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKRVEPKS CDKTHTCPPCPAPEAAGGPSVFLFPPKPKDTLMISRTPEVTCVVV DVSHEDPEVKFNWYVDGVEVHNAKTKPREEQYNSTYRVVSVLT VLHQDWLNGKEYKCKVSNKARPAPIEKTISKAKGQPREPQVYTL PPSREEMTKNQVSLTCLVKGFYPSDIAVEWESNGQPENNYKTTP PVLDSDGSFFLYSKLTVDKSRWQQGNVFSCSVMHEALHNHYTQ KSLSLSPG | 42 |
| 13E4_VH1_d | QVQLVQSGAEVKKPGASVKVSCKASGYTFTNYWMHWVRQAPG QGLEWMGEINPINGRSNYAQKFQGRVTLTVDTSISTAYMELSRL RSDDTAVYYCARGTRAMHYWGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKRVEPKS CDKTHTCPPCPAPEAAGGPSVFLFPPKPKDTLMISRTPEVTCVVV DVSHEDPEVKFNWYVDGVEVHNAKTKPREEQYNSTYRVVSVLT VLHQDWLNGKEYKCKVSNKALGAPIEKTISKAKGQPREPQVYT LPPSREEMTKNQVSLTCLVKGFYPSDIAVEWESNGQPENNYKTT PPVLDSDGSFFLYSKLTVDKSRWQQGNVFSCSVMHEALHNHYT QKSLSLSPG | 43 |

TABLE 8-continued

| NAME | HC SEQUENCE | SEQ ID NO: |
|---|---|---|
| 13E4_VH1_e | QVQLVQSGAEVKKPGASVKVSCKASGYTFTNYWMHWVRQAPG QGLEWMGEINPINGRSNYAQKFQGRVTLTVDTSISTAYMELSRL RSDDTAVYYCARGTRAMHYWGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKRVEPKS CDKTHTCPPCPAPELLGGPSVFLFPPKPKDTLMISRTPEVTCVVV AVSHEDPEVKFNWYVDGVEVHNAKTKPREEQYGSTYRVVSVLT VLHQDWLNGKEYKCKVSNKALPAPIEKTISKAKGQPREPQVYTL PPSREEMTKNQVSLTCLVKGFYPSDIAVEWESNGQPENNYKTTP PVLDSDGSFFLYSKLTVDKSRWQQGNVFSCSVMHEALHNHYTQ KSLSLSPG | 44 |
| 13E4_VH2 | QVQLVQSGAEVKKPGASVKVSCKASGYTFTNYWMHWVRQAPG QGLEWIGEINPINGRSNYAEKFQGRVTLTVDTSSSTAYMELSRLR SDDTAVYYCARGTRAMHYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKRVEPKSC DKTHTCPPCPAPELLGGPSVFLFPPKPKDTLMISRTPEVTCVVVD VSHEDPEVKFNWYVDGVEVHNAKTKPREEQYNSTYRVVSVLTV LHQDWLNGKEYKCKVSNKALPAPIEKTISKAKGQPREPQVYTLP PSREEMTKNQVSLTCLVKGFYPSDIAVEWESNGQPENNYKTTPP VLDSDGSFFLYSKLTVDKSRWQQGNVFSCSVMHEALHNHYTQK SLSLSPG | 45 |
| 13E4_VH2_a | QVQLVQSGAEVKKPGASVKVSCKASGYTFTNYWMHWVRQAPG QGLEWIGEINPINGRSNYAEKFQGRVTLTVDTSSSTAYMELSRLR SDDTAVYYCARGTRAMHYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKRVEPKSC DKTHTCPPCPAPEAAGGPSVFLFPPKPKDTLMISRTPEVTCVVVD VSHEDPEVKFNWYVDGVEVHNAKTKPREEQYNSTYRVVSVLTV LHQDWLNGKEYKCKVSNKALPAPIEKTISKAKGQPREPQVYTLP PSREEMTKNQVSLTCLVKGFYPSDIAVEWESNGQPENNYKTTPP VLDSDGSFFLYSKLTVDKSRWQQGNVFSCSVMHEALHNHYTQK SLSLSPG | 46 |
| 13E4_VH2_b | QVQLVQSGAEVKKPGASVKVSCKASGYTFTNYWMHWVRQAPG QGLEWIGEINPINGRSNYAEKFQGRVTLTVDTSSSTAYMELSRLR SDDTAVYYCARGTRAMHYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKRVEPKSC DKTHTCPPCPAPEAAGGPSVFLFPPKPKDTLMISRTPEVTCVVVD VSHEDPEVKFNWYVDGVEVHNAKTKPREEQYNSTYRVVSVLTV LHQDWLNGKEYKCGVSNKALPAPIEKTISKAKGQPREPQVYTLP PSREEMTKNQVSLTCLVKGFYPSDIAVEWESNGQPENNYKTTPP VLDSDGSFFLYSKLTVDKSRWQQGNVFSCSVMHEALHNHYTQK SLSLSPG | 47 |
| 13E4_VH2_c | QVQLVQSGAEVKKPGASVKVSCKASGYTFTNYWMHWVRQAPG QGLEWIGEINPINGRSNYAEKFQGRVTLTVDTSSSTAYMELSRLR SDDTAVYYCARGTRAMHYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKRVEPKSC DKTHTCPPCPAPEAAGGPSVFLFPPKPKDTLMISRTPEVTCVVVD VSHEDPEVKFNWYVDGVEVHNAKTKPREEQYNSTYRVVSVLTV LHQDWLNGKEYKCKVSNKARPAPIEKTISKAKGQPREPQVYTLP PSREEMTKNQVSLTCLVKGFYPSDIAVEWESNGQPENNYKTTPP VLDSDGSFFLYSKLTVDKSRWQQGNVFSCSVMHEALHNHYTQK SLSLSPG | 48 |
| 13E4_VH2_d | QVQLVQSGAEVKKPGASVKVSCKASGYTFTNYWMHWVRQAPG QGLEWIGEINPINGRSNYAEKFQGRVTLTVDTSSSTAYMELSRLR SDDTAVYYCARGTRAMHYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKRVEPKSC DKTHTCPPCPAPEAAGGPSVFLFPPKPKDTLMISRTPEVTCVVVD VSHEDPEVKFNWYVDGVEVHNAKTKPREEQYNSTYRVVSVLTV LHQDWLNGKEYKCKVSNKALGAPIEKTISKAKGQPREPQVYTLP PSREEMTKNQVSLTCLVKGFYPSDIAVEWESNGQPENNYKTTPP VLDSDGSFFLYSKLTVDKSRWQQGNVFSCSVMHEALHNHYTQK SLSLSPG | 49 |
| 13E4_VH2_e | QVQLVQSGAEVKKPGASVKVSCKASGYTFTNYWMHWVRQAPG QGLEWIGEINPINGRSNYAEKFQGRVTLTVDTSSSTAYMELSRLR SDDTAVYYCARGTRAMHYWGQGTLVTVSSASTKGPSVFPLAPS SKSTSGGTAALGCLVKDYFPEPVTVSWNSGALTSGVHTFPAVLQ | 50 |

TABLE 8-continued

| NAME | HC SEQUENCE | SEQ ID NO: |
|---|---|---|
| | SSGLYSLSSVVTVPSSSLGTQTYICNVNHKPSNTKVDKRVEPKSC DKTHTCPPCPAPELLGGPSVFLFPPKPKDTLMISRTPEVTCVVVA VSHEDPEVKFNWYVDGVEVHNAKTKPREEQYGSTYRVVSVLTV LHQDWLNGKEYKCKVSNKALPAPIEKTISKAKGQPREPQVYTLP PSREEMTKNQVSLTCLVKGFYPSDIAVEWESNGQPENNYKTTPP VLDSDGSFFLYSKLTVDKSRWQQGNVFSCSVMHEALHNHYTQK SLSLSPG | |
| 13E4_VH3 | QVQLVQSGAEVKKPGASVKVSCKASGYTFTNYWMHWVRQAPG QGLEWMGEINPIQGRSNYAEKFQGRVTLTVDTSSSTAYMELSSL RSEDTATYYCARGTRAMHYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKRVEPKSC DKTHTCPPCPAPELLGGPSVFLFPPKPKDTLMISRTPEVTCVVVD VSHEDPEVKFNWYVDGVEVHNAKTKPREEQYNSTYRVVSVLTV LHQDWLNGKEYKCKVSNKALPAPIEKTISKAKGQPREPQVYTLP PSREEMTKNQVSLTCLVKGFYPSDIAVEWESNGQPENNYKTTPP VLDSDGSFFLYSKLTVDKSRWQQGNVFSCSVMHEALHNHYTQK SLSLSPG | 51 |
| 13E4_VH3_a | QVQLVQSGAEVKKPGASVKVSCKASGYTFTNYWMHWVRQAPG QGLEWMGEINPIQGRSNYAEKFQGRVTLTVDTSSSTAYMELSSL RSEDTATYYCARGTRAMHYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKRVEPKSC DKTHTCPPCPAPEAAGGPSVFLFPPKPKDTLMISRTPEVTCVVVD VSHEDPEVKFNWYVDGVEVHNAKTKPREEQYNSTYRVVSVLTV LHQDWLNGKEYKCKVSNKALPAPIEKTISKAKGQPREPQVYTLP PSREEMTKNQVSLTCLVKGFYPSDIAVEWESNGQPENNYKTTPP VLDSDGSFFLYSKLTVDKSRWQQGNVFSCSVMHEALHNHYTQK SLSLSPG | 52 |
| 13E4_VH3_b | QVQLVQSGAEVKKPGASVKVSCKASGYTFTNYWMHWVRQAPG QGLEWMGEINPIQGRSNYAEKFQGRVTLTVDTSSSTAYMELSSL RSEDTATYYCARGTRAMHYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKRVEPKSC DKTHTCPPCPAPEAAGGPSVFLFPPKPKDTLMISRTPEVTCVVVD VSHEDPEVKFNWYVDGVEVHNAKTKPREEQYNSTYRVVSVLTV LHQDWLNGKEYKCGVSNKALPAPIEKTISKAKGQPREPQVYTLP PSREEMTKNQVSLTCLVKGFYPSDIAVEWESNGQPENNYKTTPP VLDSDGSFFLYSKLTVDKSRWQQGNVFSCSVMHEALHNHYTQK SLSLSPG | 53 |
| 13E4_VH3_c | QVQLVQSGAEVKKPGASVKVSCKASGYTFTNYWMHWVRQAPG QGLEWMGEINPIQGRSNYAEKFQGRVTLTVDTSSSTAYMELSSL RSEDTATYYCARGTRAMHYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKRVEPKSC DKTHTCPPCPAPEAAGGPSVFLFPPKPKDTLMISRTPEVTCVVVD VSHEDPEVKFNWYVDGVEVHNAKTKPREEQYNSTYRVVSVLTV LHQDWLNGKEYKCKVSNKARPAPIEKTISKAKGQPREPQVYTLP PSREEMTKNQVSLTCLVKGFYPSDIAVEWESNGQPENNYKTTPP VLDSDGSFFLYSKLTVDKSRWQQGNVFSCSVMHEALHNHYTQK SLSLSPG | 54 |
| 13E4_VH3_d | QVQLVQSGAEVKKPGASVKVSCKASGYTFTNYWMHWVRQAPG QGLEWMGEINPIQGRSNYAEKFQGRVTLTVDTSSSTAYMELSSL RSEDTATYYCARGTRAMHYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKRVEPKSC DKTHTCPPCPAPEAAGGPSVFLFPPKPKDTLMISRTPEVTCVVVD VSHEDPEVKFNWYVDGVEVHNAKTKPREEQYNSTYRVVSVLTV LHQDWLNGKEYKCKVSNKALGAPIEKTISKAKGQPREPQVYTLP PSREEMTKNQVSLTCLVKGFYPSDIAVEWESNGQPENNYKTTPP VLDSDGSFFLYSKLTVDKSRWQQGNVFSCSVMHEALHNHYTQK SLSLSPG | 55 |
| 13E4_VH3_e | QVQLVQSGAEVKKPGASVKVSCKASGYTFTNYWMHWVRQAPG QGLEWMGEINPIQGRSNYAEKFQGRVTLTVDTSSSTAYMELSSL RSEDTATYYCARGTRAMHYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKRVEPKSC DKTHTCPPCPAPELLGGPSVFLFPPKPKDTLMISRTPEVTCVVVA VSHEDPEVKFNWYVDGVEVHNAKTKPREEQYGSTYRVVSVLTV LHQDWLNGKEYKCKVSNKALPAPIEKTISKAKGQPREPQVYTLP | 56 |

TABLE 8-continued

| NAME | HC SEQUENCE | SEQ ID NO: |
|---|---|---|
| | PSREEMTKNQVSLTCLVKGFYPSDIAVEWESNGQPENNYKTTPP<br>VLDSDGSFFLYSKLTVDKSRWQQGNVFSCSVMHEALHNHYTQK<br>SLSLSPG | |
| 13E4_VH4 | QVQLVQSGAEVKKPGASVKVSCKASGYTFTNYWMHWVRQAPG<br>QGLEWMGEINPINGRSNYAEKFQGRVTLTVDTSSSTAYMELSSL<br>RSEDTATYYCARGTRAMHYWGQGTLVTVSSASTKGPSVFPLAPS<br>SKSTSGGTAALGCLVKDYFPEPVTVSWNSGALTSGVHTFPAVLQ<br>SSGLYSLSSVVTVPSSSLGTQTYICNVNHKPSNTKVDKRVEPKSC<br>DKTHTCPPCPAPELLGGPSVFLFPPKPKDTLMISRTPEVTCVVVD<br>VSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSREEMTKNQVSLTCLVKGFYPSDIAVEWESNGQPENNYKTTPP<br>VLDSDGSFFLYSKLTVDKSRWQQGNVFSCSVMHEALHNHYTQK<br>SLSLSPG | 57 |
| 13E4_VH4_a | QVQLVQSGAEVKKPGASVKVSCKASGYTFTNYWMHWVRQAPG<br>QGLEWMGEINPINGRSNYAEKFQGRVTLTVDTSSSTAYMELSSL<br>RSEDTATYYCARGTRAMHYWGQGTLVTVSSASTKGPSVFPLAPS<br>SKSTSGGTAALGCLVKDYFPEPVTVSWNSGALTSGVHTFPAVLQ<br>SSGLYSLSSVVTVPSSSLGTQTYICNVNHKPSNTKVDKRVEPKSC<br>DKTHTCPPCPAPEAAGGPSVFLFPPKPKDTLMISRTPEVTCVVVD<br>VSHEDPEVKFNWYVDGVEVHNAKTKPREEQYNSTYRVVSVLTV<br>LHQDWLNGKEYKCKVSNKALPAPIEKTISKAKGQPREPQVYTLP<br>PSREEMTKNQVSLTCLVKGFYPSDIAVEWESNGQPENNYKTTPP<br>VLDSDGSFFLYSKLTVDKSRWQQGNVFSCSVMHEALHNHYTQK<br>SLSLSPG | 58 |
| 13E4_VH4_b | QVQLVQSGAEVKKPGASVKVSCKASGYTFTNYWMHWVRQAPG<br>QGLEWMGEINPINGRSNYAEKFQGRVTLTVDTSSSTAYMELSSL<br>RSEDTATYYCARGTRAMHYWGQGTLVTVSSASTKGPSVFPLAPS<br>SKSTSGGTAALGCLVKDYFPEPVTVSWNSGALTSGVHTFPAVLQ<br>SSGLYSLSSVVTVPSSSLGTQTYICNVNHKPSNTKVDKRVEPKSC<br>DKTHTCPPCPAPEAAGGPSVFLFPPKPKDTLMISRTPEVTCVVVD<br>VSHEDPEVKFNWYVDGVEVHNAKTKPREEQYNSTYRVVSVLTV<br>LHQDWLNGKEYKCGVSNKALPAPIEKTISKAKGQPREPQVYTLP<br>PSREEMTKNQVSLTCLVKGFYPSDIAVEWESNGQPENNYKTTPP<br>VLDSDGSFFLYSKLTVDKSRWQQGNVFSCSVMHEALHNHYTQK<br>SLSLSPG | 59 |
| 13E4_VH4_c | QVQLVQSGAEVKKPGASVKVSCKASGYTFTNYWMHWVRQAPG<br>QGLEWMGEINPINGRSNYAEKFQGRVTLTVDTSSSTAYMELSSL<br>RSEDTATYYCARGTRAMHYWGQGTLVTVSSASTKGPSVFPLAPS<br>SKSTSGGTAALGCLVKDYFPEPVTVSWNSGALTSGVHTFPAVLQ<br>SSGLYSLSSVVTVPSSSLGTQTYICNVNHKPSNTKVDKRVEPKSC<br>DKTHTCPPCPAPEAAGGPSVFLFPPKPKDTLMISRTPEVTCVVVD<br>VSHEDPEVKFNWYVDGVEVHNAKTKPREEQYNSTYRVVSVLTV<br>LHQDWLNGKEYKCKVSNKARPAPIEKTISKAKGQPREPQVYTLP<br>PSREEMTKNQVSLTCLVKGFYPSDIAVEWESNGQPENNYKTTPP<br>VLDSDGSFFLYSKLTVDKSRWQQGNVFSCSVMHEALHNHYTQK<br>SLSLSPG | 60 |
| 13E4_VH4_d | QVQLVQSGAEVKKPGASVKVSCKASGYTFTNYWMHWVRQAPG<br>QGLEWMGEINPINGRSNYAEKFQGRVTLTVDTSSSTAYMELSSL<br>RSEDTATYYCARGTRAMHYWGQGTLVTVSSASTKGPSVFPLAPS<br>SKSTSGGTAALGCLVKDYFPEPVTVSWNSGALTSGVHTFPAVLQ<br>SSGLYSLSSVVTVPSSSLGTQTYICNVNHKPSNTKVDKRVEPKSC<br>DKTHTCPPCPAPEAAGGPSVFLFPPKPKDTLMISRTPEVTCVVVD<br>VSHEDPEVKFNWYVDGVEVHNAKTKPREEQYNSTYRVVSVLTV<br>LHQDWLNGKEYKCKVSNKALGAPIEKTISKAKGQPREPQVYTLP<br>PSREEMTKNQVSLTCLVKGFYPSDIAVEWESNGQPENNYKTTPP<br>VLDSDGSFFLYSKLTVDKSRWQQGNVFSCSVMHEALHNHYTQK<br>SLSLSPG | 61 |
| 13E4_VH4_e | QVQLVQSGAEVKKPGASVKVSCKASGYTFTNYWMHWVRQAPG<br>QGLEWMGEINPINGRSNYAEKFQGRVTLTVDTSSSTAYMELSSL<br>RSEDTATYYCARGTRAMHYWGQGTLVTVSSASTKGPSVFPLAPS<br>SKSTSGGTAALGCLVKDYFPEPVTVSWNSGALTSGVHTFPAVLQ<br>SSGLYSLSSVVTVPSSSLGTQTYICNVNHKPSNTKVDKRVEPKSC<br>DKTHTCPPCPAPELLGGPSVFLFPPKPKDTLMISRTPEVTCVVVA<br>VSHEDPEVKFNWYVDGVEVHNAKTKPREEQYGSTYRVVSVLTV<br>LHQDWLNGKEYKCKVSNKALPAPIEKTISKAKGQPREPQVYTLP<br>PSREEMTKNQVSLTCLVKGFYPSDIAVEWESNGQPENNYKTTPP<br>VLDSDGSFFLYSKLTVDKSRWQQGNVFSCSVMHEALHNHYTQK<br>SLSLSPG | 62 |

TABLE 9

| NAME | LC SEQUENCE | SEQ ID NO: |
|---|---|---|
| 13E4_VL1 | DIQMTQSPSSLSASVGDRVTITCRTSENIYNNLAWYQQKPGKSPK LLIYAATNLADGVPSRFSGSGSGTDYTLTISSLQPEDFATYYCQHF WGTPLTFGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGEC | 63 |
| 13E4_VL2 | DIQMTQSPSSLSASVGDRVTITCRTSENIYNNLAWYQQKPGKAPK LLIYAATNLADGVPSRFSGSGSGTDYTLTISSLQPEDFATYYCQHF WGTPLTFGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGEC | 64 |
| 13E4_VL3 | DIQMTQSPSSLSASVGDRVTITCRTSENIYNNLAWYQQKPGKAPK LLIYAATNLAEGVPSRFSGSGSGTDYTLTISSLQPEDFATYYCQHF WGTPLTFGGGTKVEIKRTVAAPSVFIFPPSDEQLKSGTASVVCLL NNFYPREAKVQWKVDNALQSGNSQESVTEQDSKDSTYSLSSTLT LSKADYEKHKVYACEVTHQGLSSPVTKSFNRGEC | 65 |
| 13E4_VL4 | DIQMTQSPSSLSASVGDRVTITCRTSENIYSNLAWYQQKPGKAPK LLIYAGTNLADGVPSRFSGSGSGTDYTLTISSLQPEDFANYYCQH FWGTPLTFGGGTKVEIKRTVAAPSVFIFPPSDEQLKSGTASVVCL LNNFYPREAKVQWKVDNALQSGNSQESVTEQDSKDSTYSLSSTL TLSKADYEKHKVYACEVTHQGLSSPVTKSFNRGEC | 66 |

In some aspects, an anti-transferrin receptor antibody described herein has an improved serum half-life compared to a reference anti-transferrin receptor antibody. In some instances, the improved serum half-life is at least 30 minutes, 1 hour, 1.5 hours, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 14 days, 30 days, or longer than the reference anti-transferrin receptor antibody.

In some aspects, an antibody or antigen binding fragment thereof is further modified using conventional techniques known in the art, for example, by using amino acid deletion, insertion, substitution, addition, and/or by recombination and/or any other modification (e.g., posttranslational and chemical modifications, such as glycosylation and phosphorylation) known in the art either alone or in combination. In some instances, the modification further comprises a modification for modulating interaction with Fc receptors. In some instances, the one or more modifications include those described in, for example, International Publication No. WO97/34631, which discloses amino acid residues involved in the interaction between the Fc domain and the FcRn receptor. Methods for introducing such modifications in the nucleic acid sequence underlying the amino acid sequence of an antibody or its binding fragment is well known to the person skilled in the art.

In some instances, an antibody or antigen binding fragment thereof further encompasses its derivatives and includes polypeptide sequences containing at least one CDR.

In some instances, the term "single-chain" as used herein means that the first and second domains of a bi-specific single chain construct are covalently linked, preferably in the form of a co-linear amino acid sequence encodable by a single nucleic acid molecule.

In some instances, a bispecific single chain antibody construct relates to a construct comprising two antibody derived binding domains. In such embodiments, the bi-specific single chain antibody construct is tandem to a bi-scFv or diabody. In some instances, a scFv contains a VH and VL domain connected by a linker peptide. In some instances, linkers are of a length and sequence sufficient to ensure that each of the first and second domains can, independently from one another, retain their differential binding specificities.

In some aspects, binding to or interacting with as used herein defines a binding/interaction of at least two antigen-interaction-sites with each other. In some instances, antigen-interaction-site defines a motif of a polypeptide that shows the capacity of specific interaction with a specific antigen or a specific group of antigens. In some cases, the binding/interaction is also understood to define a specific recognition. In such cases, specific recognition refers to whether the antibody or its binding fragment is capable of specifically interacting with and/or binding to at least two amino acids of each of a target molecule. For example, specific recognition relates to the specificity of the antibody molecule, or to its ability to discriminate between the specific regions of a target molecule. In additional instances, the specific interaction of the antigen-interaction-site with its specific antigen results in an initiation of a signal, e.g. due to the induction of a change of the conformation of the antigen, an oligomerization of the antigen, etc. In further aspects, the binding is exemplified by the specificity of a "key-lock-principle". Thus in some instances, specific motifs in the amino acid sequence of the antigen-interaction-site and the antigen bind to each other as a result of their primary, secondary or tertiary structure as well as the result of secondary modifications of said structure. In such cases, the specific interaction of the antigen-interaction-site with its specific antigen results as well as in a simple binding of the site to the antigen.

In some instances, specific interaction further refers to a reduced cross-reactivity of the antibody or its binding fragment or a reduced off-target effect. For example, the antibody or antigen binding fragment thereof that binds to the polypeptide/protein of interest but do not or do not essentially bind to any of the other polypeptides are considered as specific for the polypeptide/protein of interest. Examples for the specific interaction of an antigen-interaction-site with a specific antigen comprise the specificity of a ligand for its receptor, for example, the interaction of an antigenic determinant (epitope) with the antigenic binding site of an antibody.

Thus, in some instances, a polynucleic acid molecule conjugate comprises a polynucleic acid molecule (e.g., PMO molecule) comprising or consisting of a sequence with at least 80%, at least 85%, at least 90%, at least 95%, at least 99%, or 100% sequence identity to a sequence selected from SEQ ID NOs: 100-133, and an anti-transferrin receptor antibody or antigen binding fragment thereof conjugated to the polynucleic acid such that the polynucleic acid molecule conjugate induces exon skipping of the pre-mRNA of the DMD gene.

In certain aspects, a polynucleic acid molecule conjugate comprises an anti-transferrin receptor antibody or antigen binding fragment thereof conjugated to a polynucleic acid molecule (e.g., PMO molecule) that hybridizes to a sequence of a target region of a pre-mRNA transcript of the DMD gene, and the polynucleic acid molecule having a sense strand comprising or consisting of a sequence with at least 80%, at least 85%, at least 90%, at least 95%, at least 99%, or 100% sequence identity to a sequence selected from SEQ ID NOs: 100-133, and anti-transferrin receptor antibody or antigen binding fragment thereof comprises a variable heavy chain (VH) region and a variable light chain (VL) region, wherein the VH region comprises an HCDR1 sequence comprising or consisting of SEQ ID NO: 17, an HCDR2 sequence comprising or consisting of SEQ ID NO: 20, and an HCDR3 sequence comprising or consisting of SEQ ID NO: 19; and the VL region comprises an LCDR1 sequence comprising or consisting of SEQ ID NO: 22, an LCDR2 sequence comprising or consisting of SEQ ID NO: 23, and an LCDR3 sequence comprising or consisting of SEQ ID NO: 24, and the anti-transferrin receptor antibody or antigen binding fragment thereof and the polynucleic acid molecule is conjugated via a linker comprising 4-(N-maleimidomethyl) cyclohexane-1-amidate (SMCC).

In certain aspects, a polynucleic acid molecule conjugate comprises an anti-transferrin receptor antibody or antigen binding fragment thereof conjugated to a polynucleic acid molecule (e.g., PMO molecule) that hybridizes to a sequence of a target region of a pre-mRNA transcript of the DMD gene, and the polynucleic acid molecule comprising or consisting of a sequence with at least 80%, at least 85%, at least 90%, at least 95%, at least 99%, or 100% sequence identity to a sequence selected from SEQ ID NOs: 100-133 and the anti-transferrin receptor antibody or antigen binding fragment thereof comprises a variable heavy chain (VH) region and a variable light chain (VL) region, wherein the VH region comprises or consisting of a sequence with at least 80%, 85%, 90%, 95%, 99%, or 100% sequence identity to SEQ ID NO: 30, and wherein the VL region comprises or consisting of a sequence with at least 80%, 85%, 90%, 95%, 99%, or 100% sequence identity to SEQ ID NO: 34, and the anti-transferrin receptor antibody or antigen binding fragment thereof and the polynucleic acid molecule is conjugated via a maleimide linker.

In certain aspects, a polynucleic acid molecule conjugate comprises an anti-transferrin receptor antibody or antigen binding fragment thereof conjugated to a polynucleic acid molecule (e.g., PMO molecule) that hybridizes to a sequence of a target region of a pre-mRNA transcript of the DMD gene, and the polynucleic acid molecule comprising or consisting of a sequence with at least 80%, at least 85%, at least 90%, at least 95%, at least 99%, or 100% sequence identity to a sequence selected from SEQ ID NOs: 100-133, and comprises at least three, four, five, or six consecutive 2'-O-methyl modified nucleotides at the 5'-end and at least two, at least three 2'-F modified nucleotides, and the anti-transferrin receptor antibody or antigen binding fragment thereof comprises a variable heavy chain (VH) region and a variable light chain (VL) region, wherein the VH region comprises or consisting of a sequence with at least 80%, 85%, 90%, 95%, 99%, or 100% sequence identity to SEQ ID NO: 30, and wherein the VL region comprises or consisting of a sequence with at least 80%, 85%, 90%, 95%, 99%, or 100% sequence identity to SEQ ID NO: 34, and the anti-transferrin receptor antibody or antigen binding fragment thereof and the polynucleic acid molecule is conjugated via a maleimide linker.

In certain aspects, a polynucleic acid molecule conjugate comprises an anti-transferrin receptor antibody or antigen binding fragment thereof conjugated to a polynucleic acid molecule (e.g., PMO molecule) that hybridizes to a sequence of a target region of a pre-mRNA transcript of the DMD gene, and the polynucleic acid molecule comprises or consisting of a sequence with at least 80%, at least 85%, at least 90%, at least 95%, at least 99%, or 100% sequence identity to a sequence selected from SEQ ID NOs: 100-133, and comprises at least two, at least three, at least four, or at least five consecutive 2'-O-methyl modified nucleotide at the 3'-end of the polynucleic acid molecule, and comprises at least one, at least two, at least three, at least four 2'-F modified nucleotides, and the anti-transferrin receptor antibody or antigen binding fragment thereof comprises a variable heavy chain (VH) region and a variable light chain (VL) region, wherein the VH region comprises an HCDR1 sequence comprising or consisting of SEQ ID NO: 17, an HCDR2 sequence comprising or consisting of SEQ ID NO: 20, and an HCDR3 sequence comprising or consisting of SEQ ID NO: 19; and the VL region comprises an LCDR1 sequence comprising or consisting of SEQ ID NO: 22, an LCDR2 sequence comprising or consisting of SEQ ID NO: 23, and an LCDR3 sequence comprising or consisting of SEQ ID NO: 24, and the anti-transferrin receptor antibody or antigen binding fragment thereof and the polynucleic acid molecule is conjugated via a maleimide linker.

In certain aspects, a polynucleic acid molecule conjugate comprises an anti-transferrin receptor antibody or antigen binding fragment thereof conjugated to a polynucleic acid molecule (e.g., PMO molecule) that hybridizes to a sequence of a target region of a pre-mRNA transcript of the DMD gene, and the polynucleic acid molecule comprises or consists of a sequence with at least 80%, at least 85%, at least 90%, at least 95%, at least 99%, or 100% sequence identity to a sequence selected from SEQ ID NOs: 100-133, comprises one or more 2'-O-methyl modified nucleotides at the 5'-end and/or at the 3'-end of the polynucleic acid molecule, and the anti-transferrin receptor antibody or antigen binding fragment thereof comprises a variable heavy chain (VH) region and a variable light chain (VL) region, and the VH region comprises an HCDR1 sequence comprising or consisting of SEQ ID NO: 17, an HCDR2 sequence comprising or consisting of SEQ ID NO: 18, and an HCDR3 sequence comprising or consisting of SEQ ID NO: 19; and the VL region comprises an LCDR1 sequence comprising or consisting of SEQ ID NO: 22, an LCDR2 sequence comprising or consisting of SEQ ID NO: 3, and an LCDR3 sequence comprising or consisting of SEQ ID NO: 24, and the anti-transferrin receptor antibody or antigen binding fragment thereof and the polynucleic acid molecule is conjugated via a maleimide linker.

In certain aspects, a polynucleic acid molecule conjugate comprises an anti-transferrin receptor antibody or antigen binding fragment thereof conjugated to a polynucleic acid molecule (e.g., PMO molecule) that hybridizes to a target sequence of a pre-mRNA transcript of the DMD gene, and the polynucleic acid molecule comprising or consisting of a sequence with at least 80%, at least 85%, at least 90%, at least 95%, at least 99%, or 100% sequence identity to a sequence selected from SEQ ID NOs: 100-133, and the anti-transferrin receptor antibody or antigen binding fragment thereof comprises a variable heavy chain (VH) region and a variable light chain (VL) region, and the VH region comprises or consists of a sequence with at least 80%, at least 85%, at least 90%, at least 95%, at least 99%, or 100% sequence identity to one of SEQ ID NOs: 29-33, and wherein the VL region comprises or consists of a sequence with at least 80%, at least 85%, at least 90%, at least 95%, at least 99%, or 100% sequence identity to one of SEQ ID NOs: 34-38, and the anti-transferrin receptor antibody or antigen binding fragment thereof and the polynucleic acid molecule is conjugated via a 6-Amino-1-hexanol linker. In some instances, the polynucleic acid molecule comprises at least one or more 2'-modified nucleotide. In some instances, the polynucleic acid molecule comprises at least five consecutive 2'-O-methyl modified nucleotide at the 3'-end. In some instances, the polynucleic acid molecule comprises at least three or at least four 2'-F modified nucleotides, wherein any two of the at least three or at least four 2'-F modified nucleotides are not consecutive.

In some aspects, the antibody or antigen binding fragment thereof is conjugated to any of the PMO molecules disclosed herein non-specifically. In some instances, the antibody or antigen binding fragment thereof is conjugated to any of the PMO molecules disclosed herein via a lysine residue or a cysteine residue, in a non-site specific manner. In some instances, the antibody or antigen binding fragment thereof is conjugated to any of the PMO molecules disclosed herein via a lysine residue in a non-site specific manner. In some cases, the antibody or antigen binding fragment thereof is conjugated to any of the PMO molecules disclosed herein via a cysteine residue in a non-site specific manner.

In some aspects, the antibody or antigen binding fragment thereof is conjugated to any of the PMO molecules disclosed herein in a site-specific manner. In some instances, the antibody or antigen binding fragment thereof is conjugated to any of the PMO molecules disclosed herein through a lysine residue, a cysteine residue, at the 5'-terminus, at the 3'-terminus, an unnatural amino acid, or an enzyme-modified or enzyme-catalyzed residue, via a site-specific manner. In some instances, the antibody or antigen binding fragment thereof is conjugated to any of the PMO molecules disclosed herein through a lysine residue via a site-specific manner. In some instances, the antibody or antigen binding fragment thereof is conjugated to any of the PMO molecules disclosed herein through a cysteine residue via a site-specific manner. In some instances, the antibody or antigen binding fragment thereof is conjugated to any of the PMO molecules disclosed herein at the 5'-terminus via a site-specific manner. In some instances, the antibody or antigen binding fragment thereof is conjugated to any of the PMO molecules disclosed herein at the 3'-terminus via a site-specific manner. In some instances, the antibody or antigen binding fragment thereof is conjugated to any of the PMO molecules disclosed herein through an unnatural amino acid via a site-specific manner. In some instances, the antibody or antigen binding fragment thereof is conjugated to any of the PMO molecules disclosed herein through an enzyme-modified or enzyme-catalyzed residue via a site-specific manner.

In some aspects, one or more PMO molecule is conjugated to any of the antibodies or antigen binding fragments thereof disclosed herein. In some instances, about 1, 2, 3, 4, 5, 6, 7, 8, 9, 10, 11, 12, 13, 14, 15, 16, or more PMO molecules are conjugated to an antibody or antigen binding fragment thereof. In some instances, about 1 PMO molecule is conjugated to one antibody or antigen binding fragment thereof. In some instances, about 2 PMO molecules are conjugated to one antibody or antigen binding fragment thereof. In some instances, about 3 PMO molecules are conjugated to one antibody or antigen binding fragment thereof. In some instances, about 4 PMO molecules are conjugated to one. In some instances, about 5 PMO molecules are conjugated to one antibody or antigen binding fragment thereof. In some instances, about 6 PMO molecules are conjugated to one antibody or antigen binding fragment thereof. In some instances, about 7 PMO molecules are conjugated to one antibody or antigen binding fragment thereof. In some instances, about 8 PMO molecules are conjugated to one antibody or antigen binding fragment thereof.

In some aspects, at least 1, 2, 3, 4, 5, 6, 7, 8, 9, 10, 11, 12, 13, 14, 15, 16, 17, 18, 19, or 20 PMO molecules are conjugated to an antibody or antigen binding fragment thereof. In some instances, at least 1 PMO molecule is conjugated to one antibody or antigen binding fragment thereof. In some instances, at least 2 PMO molecules are conjugated to one antibody or antigen binding fragment thereof. In some instances, at least 3 PMO molecules are conjugated to one antibody or antigen binding fragment thereof. In some instances, at least 4 PMO molecules are conjugated to one. In some instances, at least 5 PMO molecules are conjugated to one antibody or antigen binding fragment thereof. In some instances, at least 6 PMO molecules are conjugated to one antibody or antigen binding fragment thereof. In some instances, at least 7 PMO molecules are conjugated to one antibody or antigen binding fragment thereof. In some instances, at least 8 PMO molecules are conjugated to one antibody or antigen binding fragment thereof.

In some instances, from about 1 to about 16 PMO molecules are conjugated to an antibody or antigen binding fragment thereof. In some instances, from about 2 to about 15 PMO molecules are conjugated to an antibody or antigen binding fragment thereof. In some instances, from about 3 to about 14 PMO molecules are conjugated to an antibody or antigen binding fragment thereof. In some instances, from about 4 to about 13 PMO molecules are conjugated to an antibody or antigen binding fragment thereof. In some instances, from about 5 to about 12 PMO molecules are conjugated to an antibody or antigen binding fragment thereof. In some instances, from about 6 to about 11 PMO molecules are conjugated to an antibody or antigen binding fragment thereof. In some instances, from about 7 to about 10 PMO molecules are conjugated to an antibody or antigen binding fragment thereof. In some instances, from about 8 to about 9 PMO molecules are conjugated to an antibody or antigen binding fragment thereof.

In some aspects, an average of one or more PMO molecule is conjugated to an antibody or antigen binding fragment thereof. In some instances, an average of about 1, 2, 3, 4, 5, 6, 7, 8, 9, 10, 11, 12, 13, 14, 15, 16, or more PMO molecules are conjugated to an antibody or antigen binding fragment thereof. In some instances, an average of about 1 PMO molecule is conjugated to one antibody or antigen binding fragment thereof. In some instances, an average of about 2 PMO molecules are conjugated to one antibody or antigen binding fragment thereof. In some instances, an average of about 3 PMO molecules are conjugated to one antibody or antigen binding fragment thereof. In some instances, an average of about 4 PMO molecules are conjugated to one. In some instances, an average of about 5 PMO molecules are conjugated to one antibody or antigen binding fragment thereof. In some instances, an average of about 6 PMO molecules are conjugated to one antibody or antigen binding fragment thereof. In some instances, an average of about 7 PMO molecules are conjugated to one antibody or antigen binding fragment thereof. In some instances, an average of about 8 PMO molecules are conjugated to one antibody or antigen binding fragment thereof.

In some instances, an average of at least 1, 2, 3, 4, 5, 6, 7, 8, 9, 10, 11, 12, 13, 14, 15, 16, or 17 PMO molecules are conjugated to an antibody or antigen binding fragment thereof. In some instances, an average of at least 1 PMO molecule is conjugated to one antibody or antigen binding fragment thereof. In some instances, an average of at least 2 PMO molecules are conjugated to one antibody or antigen binding fragment thereof. In some instances, an average of at least 3 PMO molecules are conjugated to one antibody or antigen binding fragment thereof. In some instances, an average of at least 4 PMO molecules are conjugated to one. In some instances, an average of at least 5 PMO molecules are conjugated to one antibody or antigen binding fragment thereof.

In some instances, the DAR ratio of the PMO molecule to antibody is about 7 or greater. In some instances, the DAR ratio of the PMO molecule to antibody is about 8 or greater.

In some aspects, the average number of PMO molecules conjugated to an antibody forms an average ratio. In some instances, the average ratio is referred to as an average DAR (drug-to-antibody) ratio, in which the drug as referred to herein is the PMO molecule. In some instances, the average DAR ratio of the PMO molecule to antibody is about 1, 2, 3, 4, 5, 6, 7, 8, 9, 10, 11, 12, 13, 14, 15, 16, or greater. In some instances, the average DAR ratio of the PMO molecule to antibody is about 1 or greater. In some instances, the average DAR ratio of the PMO molecule to antibody is about 2 or greater. In some instances, the average DAR ratio of the PMO molecule to antibody is about 3 or greater. In some instances, the average DAR ratio of PMO molecule to antibody is about 4 or greater. In some instances, the average DAR ratio of the PMO molecules to antibody is about 5 or greater. In some instances, the average DAR ratio of the PMO molecule to antibody is about 6 or greater. In some instances, the average DAR ratio of the PMO molecule to antibody is about 7 or greater. In some instances, the average DAR ratio of the PMO molecule to antibody is about 8 or greater.

In some aspects, the average number of PMO molecules conjugated to an antibody forms an average ratio. In some instances, the average ratio is referred to as an average DAR (drug-to-antibody) ratio, in which the drug as referred to herein is the PMO molecule. In some instances, the average DAR ratio of the PMO molecule to antibody is in the range of 1.5-2.5, 2.5-3.5, 3.5-4.5, 4.5-5.5, 5.5-6.5, 6.5-7.5, 7.5-8.5, 8.5-9.5, 9.5-10.5, 10.5-11.5, 11.5-12.5, 12.5-13.5, 13.5-14.5, 14.5-15.5, 15.5-16.5, or 16.5-17.5. In some instances, the average DAR ratio of the PMO molecule to antibody is in the range of 1.5-2.5. In some instances, the average DAR ratio of the PMO molecule to antibody is in the range of 2.5-3.5. In some instances, the average DAR ratio of the PMO molecule to antibody is in the range of 3.5-4.5. In some instances, the average DAR ratio of PMO molecule to antibody is in the range of 4.5-5.5. In some instances, the average DAR ratio of the PMO molecules to antibody is in the range of 5.5-6.5. In some instances, the average DAR ratio of the PMO molecule to antibody is in the range of 6.5-7.5. In some instances, the average DAR ratio of the PMO molecule to antibody is in the range of 7.5-8.5.

Conjugation Chemistry

In some aspects, the polynucleic acid molecule (e.g., PMO) disclosed herein is conjugated to an antibody (e.g., the antibody disclosed herein). In some instances, the antibody comprises amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of antibody also include steroids, such as cholesterol, phospholipids, di- and triacylglycerols, fatty acids, hydrocarbons (e.g., saturated, unsaturated, or contains substitutions), enzyme substrates, biotin, digoxigenin, and polysaccharides. In some instances, the polynucleic acid molecule is further conjugated to a polymer, and optionally an endosomolytic moiety.

In some aspects, the polynucleic acid molecule is conjugated to the antibody by a chemical ligation process. In some instances, the polynucleic acid molecule is conjugated to the antibody by a native ligation. In some instances, the conjugation is as described in: Dawson, et al. "Synthesis of proteins by native chemical ligation," Science 1994, 266, 776-779; Dawson, et al. "Modulation of Reactivity in Native Chemical Ligation through the Use of Thiol Additives," J. Am. Chem. Soc. 1997, 119, 4325-4329; Hackeng, et al. "Protein synthesis by native chemical ligation: Expanded scope by using straightforward methodology.," Proc. Natl. Acad. Sci. USA 1999, 96, 10068-10073; or Wu, et al. "Building complex glycopeptides: Development of a cysteine-free native chemical ligation protocol," Angew. Chem. Int. Ed. 2006, 45, 4116-4125. In some instances, the conjugation is as described in U.S. Pat. No. 8,936,910. In some aspects, the polynucleic acid molecule is conjugated to the antibody either site-specifically or non-specifically via native ligation chemistry.

In some instances, the polynucleic acid molecule is conjugated to the antibody by a site-directed method utilizing a "traceless" coupling technology (Philochem). In some instances, the "traceless" coupling technology utilizes an N-terminal 1,2-aminothiol group on the antibody which is then conjugated with a polynucleic acid molecule containing an aldehyde group. (see Casi et al., "Site-specific traceless coupling of potent cytotoxic drugs to recombinant antibodies for pharmacodelivery," JACS 134(13): 5887-5892 (2012))

In some instances, the polynucleic acid molecule is conjugated to the antibody by a site-directed method utilizing an unnatural amino acid incorporated into the antibody. In some instances, the unnatural amino acid comprises p-acetylphenylalanine (pAcPhe). In some instances, the keto group of pAcPhe is selectively coupled to an alkoxy-amine derivatived conjugating moiety to form an oxime bond. (see Axup et al., "Synthesis of site-specific antibody-drug conjugates using unnatural amino acids," PNAS 109(40): 16101-16106 (2012)).

In some instances, the polynucleic acid molecule is conjugated to the antibody by a site-directed method utilizing an enzyme-catalyzed process. In some instances, the site-directed method utilizes SMARTag™ technology (Redwood). In some instances, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized polynucleic acid molecule via hydrazino-Pictet- Spengler (HIPS) ligation. (see Wu et al., "Site-specific chemical modification of recombinant proteins produced in mammalian cells by using the genetically encoded aldehyde tag," PNAS 106(9): 3000-3005 (2009); Agarwal, et al., "A Pictet-Spengler ligation for protein chemical modification," PNAS 110(1): 46-51 (2013))

In some instances, the enzyme-catalyzed process comprises microbial transglutaminase (mTG). In some cases, the polynucleic acid molecule is conjugated to the antibody utilizing a microbial transglutaminze catalyzed process. In some instances, mTG catalyzes the formation of a covalent bond between the amide side chain of a glutamine within the recognition sequence and a primary amine of a functionalized polynucleic acid molecule. In some instances, mTG is produced from *Streptomyces mobarensis*. (see Strop et al., "Location matters: site of conjugation modulates stability and pharmacokinetics of antibody drug conjugates," Chemistry and Biology 20(2) 161-167 (2013))

In some instances, the polynucleic acid molecule is conjugated to the antibody by a method as described in PCT Publication No. WO2014/140317, which utilizes a sequence-specific transpeptidase.

In some instances, the polynucleic acid molecule is conjugated to the antibody by a method as described in U.S. Patent Publication Nos. 2015/0105539 and 2015/0105540.

Production of Antibodies or Antigen Binding Fragments Thereof

In some aspects, polypeptides described herein (e.g., antibodies and antigen binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or antigen binding fragment thereof is expressed recombinantly, and the nucleic acid encoding the antibody or antigen binding fragment is assembled from chemically synthesized oligonucleotides (e.g., as described in Kutmeier et al., 1994, BioTechniques 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or antigen binding fragment thereof is optionally generated by immunizing an animal, such as a rabbit, to generate polyclonal antibodies or, more preferably, by generating monoclonal antibodies, e.g., as described by Kohler and Milstein (1975, Nature 256:495-497) or, as described by Kozbor et al. (1983, Immunology Today 4:72) or Cole et al. (1985 in Monoclonal Antibodies and Cancer Therapy, Alan R. Liss, Inc., pp. 77-96). Alternatively, a clone encoding at least the Fab portion of the antibody is optionally obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

In some aspects, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region, e.g., humanized antibodies.

In some aspects, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, Science 242:1038-1041).

In some aspects, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific aspects, the expression of the antibody is regulated by a constitutive, an inducible or a tissue-specific promoter.

In some aspects, a variety of host-expression vector systems is utilized to express an antibody or antigen binding fragment thereof described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces Pichia*) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker.

Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes are employed in tk-, hgprt- or aprt-cells, respectively. Also, antimetabolite resistance are used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-215) and hygro, which confers resistance to hygromycin (Santerre et al., 1984, Gene 30:147). Methods commonly known in the art of recombinant DNA technology which can be used are described in Ausubel et al. (eds., 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1).

In some instances, the expression levels of an antibody are increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, Mol. Cell Biol. 3:257).

In some instances, any method known in the art for purification or analysis of an antibody or antibody conjugates is used, for example, by chromatography (e.g., ion exchange, affinity, particularly by affinity for the specific antigen after Protein A, and sizing column chromatography), centrifugation, differential solubility, or by any other standard technique for the purification of proteins. Exemplary chromatography methods included, but are not limited to, strong anion exchange chromatography, hydrophobic interaction chromatography, size exclusion chromatography, and fast protein liquid chromatography.

Linkers

In some aspects, a linker described herein is a cleavable linker or a non-cleavable linker. In some instances, the linker is a cleavable linker. In other instances, the linker is a non-cleavable linker.

In some cases, the linker is a non-polymeric linker. A non-polymeric linker refers to a linker that does not contain a repeating unit of monomers generated by a polymerization process. Exemplary non-polymeric linkers include, but are not limited to, C1-C6 alkyl group (e.g., a C5, C4, C3, C2, or C1 alkyl group), homobifunctional cross linkers, heterobifunctional cross linkers, peptide linkers, traceless linkers, self-immolative linkers, maleimide-based linkers, or combinations thereof. In some cases, the non-polymeric linker comprises a C1-C6 alkyl group (e.g., a C5, C4, C3, C2, or C1 alkyl group), a homobifunctional cross linker, a heterobifunctional cross linker, a peptide linker, a traceless linker, a self-immolative linker, a maleimide-based linker, or a combination thereof. In additional cases, the non-polymeric linker does not comprise more than two of the same type of linkers, e.g., more than two homobifunctional cross linkers, or more than two peptide linkers. In further cases, the non-polymeric linker optionally comprises one or more reactive functional groups.

In some instances, the non-polymeric linker does not encompass a polymer that is described above. In some instances, the non-polymeric linker does not encompass a polymer encompassed by the polymer moiety C. In some cases, the non-polymeric linker does not encompass a polyalkylene oxide (e.g., PEG). In some cases, the non-polymeric linker does not encompass a PEG.

In some instances, the linker comprises a homobifunctional linker. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis (sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[D-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some aspects, the linker comprises a heterobifunctional linker. Exemplary heterobifunctional linker include, but are not limited to, amine-reactive and sulfhydryl cross-linkers such as N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio) toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl (4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ- maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino)hexanoyl)amino] hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl) amino) hexanoate (sIACX), p-nitrophenyl iodoacetate (NPIA), carbonyl-reactive and sulfhydryl-reactive cross-linkers such as 4-(4-N-maleimidophenyl)butyric acid hydrazide (MPBH), 4-(N-maleimidomethyl)cyclohexane-1-carboxyl-hydrazide-8 (M2C2H), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(ρ-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1, 3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(ρ-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (pNPDP), ρ-nitrophenyl-2-diazo-3,3,3-trifluoropropionate (PNP-DTP), sulfhydryl-reactive and photoreactive cross-linkers such as1-(ρ-Azidosalicylamido)-4-(iodoacetamido)butane (AsIB), N-[4-(ρ-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(ρ-azidosalicylamido)butylamine (AsBA), and arginine-reactive and photoreactive cross-linkers such as ρ-azidophenyl glyoxal (APG).

In some instances, the linker comprises a reactive functional group. In some cases, the reactive functional group comprises a nucleophilic group that is reactive to an electrophilic group present on an antibody. Exemplary electrophilic groups include carbonyl groups-such as aldehyde, ketone, carboxylic acid, ester, amide, enone, acyl halide or acid anhydride. In some aspects, the reactive functional group is aldehyde. Exemplary nucleophilic groups include hydrazide, oxime, amino, hydrazine, thiosemicarbazone, hydrazine carboxylate, and arylhydrazide.

In some aspects, the linker comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some aspects, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," Nat. Biotechnol. 32(10):1059-1062 (2014). In some instances, the linker comprises a self-stabilizing maleimide. In some instances, the linker is a self-stabilizing maleimide.

In some aspects, the linker comprises a peptide moiety. In some instances, the peptide moiety comprises at least 2, 3, 4, 5, or 6 more amino acid residues. In some instances, the peptide moiety comprises at most 2, 3, 4, 5, 6, 7, or 8 amino acid residues. In some instances, the peptide moiety comprises about 2, about 3, about 4, about 5, or about 6 amino acid residues. In some instances, the peptide moiety is a cleavable peptide moiety (e.g., either enzymatically or chemically). In some instances, the peptide moiety is a non-cleavable peptide moiety. In some instances, the peptide moiety comprises Val-Cit (valine-citrulline), Gly-Gly-Phe-Gly (SEQ ID NO: 96), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 97), or Gly-Phe-Leu-Gly (SEQ ID NO: 98). In some instances, the linker comprises a peptide moiety such as: Val-Cit (valine-citrulline), Gly-Gly-Phe-Gly (SEQ ID NO: 96), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 97), or Gly-Phe-Leu-Gly (SEQ ID NO: 98). In some cases, the linker comprises Val-Cit. In some cases, the linker is Val-Cit.

In some aspects, the linker comprises a benzoic acid group, or its derivatives thereof. In some instances, the benzoic acid group or its derivatives thereof comprise paraaminobenzoic acid (PABA). In some instances, the benzoic acid group or its derivatives thereof comprise gamma-aminobutyric acid (GABA).

In some aspects, the linker comprises one or more of a maleimide group, a peptide moiety, and/or a benzoic acid group, in any combination. In some aspects, the linker comprises a combination of a maleimide group, a peptide moiety, and/or a benzoic acid group. In some instances, the maleimide group is maleimidocaproyl (mc). In some instances, the peptide group is val-cit. In some instances, the benzoic acid group is PABA. In some instances, the linker comprises a mc-val-cit group. In some cases, the linker comprises a val-cit-PABA group. In additional cases, the linker comprises a mc-val-cit-PABA group.

In some aspects, the linker is a self-immolative linker or a self-elimination linker. In some cases, the linker is a self-immolative linker. In other cases, the linker is a self-elimination linker (e.g., a cyclization self-elimination linker). In some instances, the linker comprises a linker described in U.S. Pat. No. 9,089,614 or PCT Publication No. WO2015038426.

In some aspects, the linker is a dendritic type linker. In some instances, the dendritic type linker comprises a branching, multifunctional linker moiety. In some instances, the dendritic type linker is used to increase the molar ratio of polynucleotide to the antibody. In some instances, the dendritic type linker comprises PAMAM dendrimers.

In some aspects, the linker is a traceless linker or a linker in which after cleavage does not leave behind a linker moiety (e.g., an atom or a linker group) to a binding moiety (e.g., an antibody), a polynucleotide, a polymer, or an endosomolytic moiety. Exemplary traceless linkers include, but are not limited to, germanium linkers, silicium linkers, sulfur linkers, selenium linkers, nitrogen linkers, phosphorus linkers, boron linkers, chromium linkers, or phenylhydrazide linkers. In some cases, the linker is a traceless aryl-triazene linker as described in Hejesen, et al., "A traceless aryl-triazene linker for DNA-directed chemistry," *Org Biomol Chem* 11(15): 2493-2497 (2013). In some instances, the linker is a traceless linker described in Blaney, et al., "Traceless solid-phase organic synthesis," *Chem. Rev.* 102: 2607-2024 (2002). In some instances, a linker is a traceless linker as described in U.S. Pat. No. 6,821,783.

In some instances, the linker is a linker described in U.S. Pat. Nos. 6,884,869; 7,498,298; 8,288,352; 8,609,105; or 8,697,688; U.S. Patent Publication Nos. 2014/0127239; 2013/028919; 2014/286970; 2013/0309256; 2015/037360; or 2014/0294851; or PCT Publication Nos. WO2015057699; WO2014080251; WO2014197854; WO2014145090; or WO2014177042.

In some instances, the linker is a C1-C6 alkyl group. In some cases, the linker is a C1-C6 alkyl group, such as for example, a C5, C4, C3, C2, or C1 alkyl group. In some cases, the C1-C6 alkyl group is an unsubstituted C1-C6 alkyl group. As used in the context of a linker, and in particular in the context of the linker, alkyl means a saturated straight or branched hydrocarbon radical containing up to six carbon atoms. In some instances, the linker is a non-polymeric linker. In some instances, the linker includes a homobifunctional linker or a heterobifunctional linker described supra. In some cases, the linker includes a heterobifunctional linker. In some cases, the linker includes or comprises sMCC. In other instances, the linker includes a heterobifunctional linker optionally conjugated to a C1-C6 alkyl group. In other instances, the linker includes sMCC optionally conjugated to a C1-C6 alkyl group. In additional instances, the linker does not include a homobifunctional linker or a heterobifunctional linker described supra.

Pharmaceutical Formulation

In some aspects, the pharmaceutical formulations described herein are administered to a subject by multiple administration routes, including but not limited to, parenteral (e.g., intravenous, subcutaneous, intramuscular), oral, intranasal, buccal, rectal, or transdermal administration routes. In some instances, the pharmaceutical composition described herein is formulated for parenteral (e.g., intravenous, subcutaneous, intramuscular, intra-arterial, intraperitoneal, intrathecal, intracerebral, intracerebroventricular, or intracranial) administration. In other instances, the pharmaceutical composition described herein is formulated for oral administration. In still other instances, the pharmaceutical composition described herein is formulated for intranasal administration.

In some aspects, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some instances, the pharmaceutical formulation includes multiparticulate formulations. In some instances, the pharmaceutical formulation includes nanoparticle formulations. In some instances, nanoparticles comprise cMAP, cyclodextrin, or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. In some instances, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements (e.g., with one or more of a polynucleic acid molecule or binding moiety (e.g., antibody described herein)). In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin or dextrin or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, a polynucleic acid molecule or a binding moiety (e.g., antibody) described herein is conjugated either directly or indirectly to the nanoparticle. In some instances, at least 1, 5, 10, 15, 20, 30, 40, 50, 60, 70, 80, 90, 100 or more polynucleic acid molecules or binding moieties described herein are conjugated either directly or indirectly to a nanoparticle.

In some aspects, the pharmaceutical formulation comprise a delivery vector, e.g., a recombinant vector, the delivery of the polynucleic acid molecule into cells. In some instances, the recombinant vector is DNA plasmid. In other instances, the recombinant vector is a viral vector. Exemplary viral vectors include vectors derived from adeno-associated virus, retrovirus, adenovirus, or alphavirus. In some instances, the recombinant vectors capable of expressing the polynucleic acid molecules provide stable expression in target cells. In additional instances, viral vectors are used that provide for transient expression of polynucleic acid molecules.

In some aspects, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Therapeutic Regimens

In some aspects, the pharmaceutical compositions described herein are administered for therapeutic applications. In some aspects, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some aspects, one or more pharmaceutical compositions are administered simultaneously, sequentially, or at an interval period of time. In some aspects, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some aspects, two or more different pharmaceutical compositions are coadministered. In some instances, the two or more different pharmaceutical compositions are coadministered simultaneously. In some cases, the two or more different pharmaceutical compositions are coadministered sequentially without a gap of time between administrations. In other cases, the two or more different pharmaceutical compositions are coadministered sequentially with a gap of about 0.5 hours, 1 hour, 2 hours, 3 hours, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some aspects, the amount of a given agent that corresponds to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some aspects, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in humans. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain aspects, are kits and articles of manufacture for use with one or more of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include target nucleic acid molecule described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain aspects, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some aspects, the mammal is a human. In some aspects, the mammal is a non-human. None of the terms require or are limited to situations characterized by the supervision (e.g., constant or intermittent) of a health care worker (e.g., a doctor, a registered nurse, a nurse practitioner, a physician's assistant, an orderly or a hospice worker).

As used here, the term "DMD subject" mean any mammal that suffers or expected to suffer from DMD, and/or has a genetic predisposition (e.g., mutations in DMD gene) related to the DMD. In some aspects, the mammal is a human. In some aspects, the mammal is a non-human.

EXAMPLES

These examples are provided for illustrative purposes only and not to limit the scope of the claims provided herein.

Example 1: In Silico Identification of Phosphorodiamidate Morpholino Oligomers (PMOs) with Predicted High hDMD Exon 44 Skipping Activity Several algorithms have been reported to identify regions on the hDMD pre-mRNA that would be amendable for exon 44 skipping activity. PMO screening was focused on a specific region most proximal to the exon 44 acceptor site based on reported predictions for exon 44 skipping (Echigoya et al. 2015, PLoS ONE 10(3): e0120058).

PMOs having hDMD exon 44 skipping activity were identified in silico. FIG. 1 shows exon 44 skipping activity of PMO 30-mers and 25-mers. The PMO binding to the positions of the exon 44 acceptor site are labelled based on the distance (bases) of their 3'-end from the acceptor site. Large squares represent the exon 44 skipping activity of PMOs and dots represent PMOs with predicted exon 44 skipping activity. The acceptor site for exon 44 has a length of 148 base pairs (Source: NCBI A *Homo sapiens* dystrophin (DMD), transcript variant Dp427m, mRNA. ACCESSION NM_004006)

(SEQ ID NO: 134)
5'-GCGATTTGACAGATCTGTTGAGAAATGGCGGCGTTTTCATTATGAT

ATAAAGATATTTAATCAGTGGCTAACAGAAGCTGAACAGTTTCTCAGAA

AGACACAAATTCCTGAGAATTGGGAACATGCTAAATACAAATGGTATCT

TAAG-3', and most active exon 44 skipping PMOs were observed to interact between the acceptor site at position 0 (Ac0) and the acceptor site at position 20 (Ac20). 12 PMOs (30-mers) with predicted hDMD exon 44 skipping activity greater than 70% (see box in FIG. 1) were further identified. The sequences of these 12 PMOs targeting the hDMD exon 44 acceptor sites are shown in Table 1.

Results

Overall, 12 phosphorodiamidate morpholino oligomers (PMOs) with highest predicted exon 44 skipping activity were selected based on the algorithm that assist with the identification of regions on the hDMD pre-mRNA that can be amenable for exon 44 skipping activity.

Example 2: Identification and Selection of PMO with High Exon 44 Skipping Activity in Healthy Primary Human Skeletal Muscle Cells (hSkMCs)

Selected 12 PMOs having high predicted exon 44 skipping activity from Example 1 were synthesized for additional in vitro assays in healthy primary human skeletal muscle cells. Primary human Skeletal Muscle Cells (SkMCs) were obtained commercially (Gibco, #A11440). These cells were pre-differentiated and induced to form myotubes by plating on collagen Type 1 coated 24-well plates (Gibco, #1970788) (50000 cells/well) in DMEM supplemented with 2% horse serum and 1×ITS (Gibco, #1933286) for 2 days according to the manufacturer's instructions. Cells were incubated without antibiotics for 24 hours prior to transfection. PMOs were synthesized by GeneTools. PMOs were formulated in water, heated at 65-70° C. for 5 minutes, and diluted into warm medium together with 2 μM Endo-Porter (Gene Tools, #EP6P1-1) to facilitate PMO uptake into cells. Cells were harvested 48 hours post transfection. Cells were collected in Trizol and stored at −80° C. until processing for RNA isolation using Direct-zol-96 RNA isolation kit (Zymo) according to the manufacturer's instructions. Total RNA concentration was quantified spectroscopically. 100-200 ng of purified RNA was converted to cDNA using High-Capacity cDNA Reverse Transcription Kit (Applied Biosystems) and a SimpliAmp Thermal Cycler (Applied Biosystems). DNA fragments representing total DMD mRNA or exon 44-skipped mRNAs were amplified by PCR using TaqMan Fast Advanced Master mix (Applied Biosystems) and either a hDMD TaqMan assay Hs01049401_m1 (VIC-MGB, Thermo Fisher Scientific) or a custom-made TaqMan assay specific for the hDMD exon 43/45 junction (FAM-MGB, Forward: 5'-CTGTGGAAAGGGTGAAGCTA-3' (SEQ ID NO:90), Reverse: 5'-GACAAGGGAACTCCAGGATG-3' (SEQ ID NO:91), Probe: 5'-AGCTCTCTCCCAGCTTGAT-TTCCA-3' (SEQ ID NO:92)). For quantification of exon 44-skipped levels by gel electrophoresis, PCR reactions were incubated at 95° C. for 20 seconds, followed by 32 cycles of 95° C. for 1 sec and 60° C. for 20 sec using a QuantStudio 7 Flex (Applied Biosystems). PCR products were diluted 4:1 with TAE loading buffer, loaded onto 24-well 4% TAE gels (Embi Tec, #GG3807) containing GelGreen. PCR products were separated by electrophoresis (50 V for 2 hours). The intensity of bands corresponding to total DMD and skipped DMD products were quantified by densitometry using ChemiDoc™ XRS+(Bio-Rad).

Results

The selected 12 PMOs were transfected in primary healthy HSkMCs that were pre-differentiated into myotubes using Endoporter as described above and harvested 48 hours post transfection. Total DMD mRNAs and exon 44 skipped DMD mRNAs were amplified by RT-qPCR. PCR products were separated by gel electrophoresis and quantified by densitometry. The presented data were fitted with a specific binding algorithm (single site). Best-fit values of the binding affinity (Kd=EC50) and (Bmax=max % skipping) are reported in Table 10. These results are from 2 independent experiments conducted with either 1, 3 and 10 μM or 0.1, 1 and 10 μM of the PMOs in duplicates.

TABLE 10

| PMO | Max % skipping | EC 50 (μM) | $K_d$ (mM) | $B_{max}$ |
|---|---|---|---|---|
| No PMO (BG) | 6.1 | N/A | N/A | N/A |
| hEx44_Ac0 | 88.9 | 1.4 | 0.3 | 95.5 |
| hEx44_Ac1 | 92.7 | 0.7 | 0.5 | 120.1 |
| hEx44_Ac2 | 98.8 | 2.7 | 0.5 | 110.8 |
| hEx44_Ac3 | 83.3 | 1.7 | 0.5 | 94.9 |
| hEx44_Ac4 | 90.5 | 0.6 | 0.3 | 95.1 |
| hEx44_Ac5 | 76.8 | 1.4 | 0.3 | 82.8 |
| hEx44_Ac6 | 83.9 | 2.1 | 0.5 | 89.6 |
| hEx44_Ac7 | 91.3 | 3.0 | 0.5 | 96.8 |

TABLE 10-continued

| PMO | Max % skipping | EC 50 (μM) | $K_d$ (mM) | $B_{max}$ |
|---|---|---|---|---|
| hEx44_Ac8 | 83.4 | 4.3 | 0.5 | 89.8 |
| hEx44_Ac9 | 77.7 | No fit | 0.3 | 82.3 |
| hEx44_Ac10 | 85.5 | 8.7 | 1.0 | 100.1 |
| hEx44_Ac14 | 85.6 | 2.0 | 0.3 | 81.7 |

Results

Figure 2:
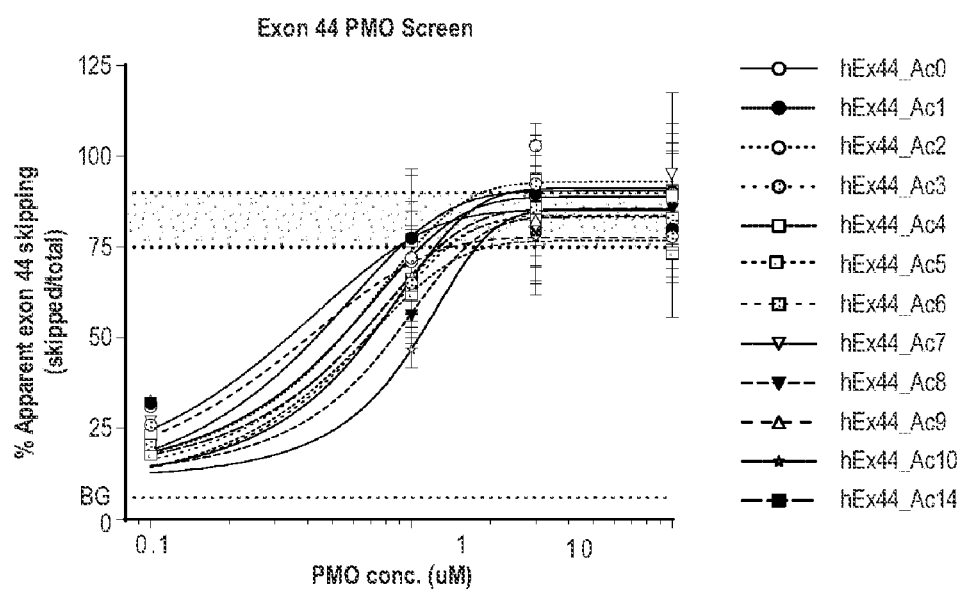
FIG. 2 is a plot of the dose response curve of the relative levels of exon 44 skipping in response to increasing concentrations of 12 different 30-mer PMOs in human immortalized myoblasts.

FIG. 2 shows the dose dependent response of the exon 44 skipping activity of the selected 12 PMOs (30-mers) targeting the acceptor site of human DMD exon 44 in healthy primary human skeletal muscle cells (hSkMCs).

The results of the assay in HSkMCs indicate that the maximal hDMD exon 44 skipping activity of the tested PMOs was greater than 75% confirming their predicted activities as shown in Table 10 and FIG. 2. In addition, the dose response of exon 44 skipping activity cells for the selected 12 PMOs (30-mers) all showed similar binding affinities (Kd) as shown in Table 10 (0.3-1.0 mM; single site, specific binding algorithm).

Overall, the in vitro assays for the activities of the selected 12 PMOs confirm their predicted exon 44 skipping activities.

Example 3: Selection of Length-Optimized Exon 44 Skipping PMO in Human Healthy Immortalized Myoblasts In order to select PMOs with an optimal length/activity ratio, shorter PMO oligonucleotides targeting Ac0-Ac10 sites were analyzed for their predicted free binding energy (ΔG) targeting the exon 44 acceptor site. Table 11 shows the predicted free binding energy (ΔG (kcal/mol)) of PMOs of various lengths targeting the exon 44 acceptor site of hDMD. ΔG was calculated using DNA-DNA oligonucleotide hybridization as first approximation (IDT oligo analyzer).

TABLE 11

| Target Site | PMO Length | | | | |
|---|---|---|---|---|---|
| | 25-mer | 26-mer | 27-mer | 28-mer | 30-mer |
| Ac0 | −44.2 | −45.6 | −47.6 | −50.7 | −57.4 |
| Ac1 | −42.5 | −44.5 | −47.5 | −50.7 | −57.3 |
| Ac2 | −40.8 | −43.9 | −47 | −50.7 | −56.9 |
| Ac3 | −42.3 | −45.5 | −50.7 | −52.2 | −58.9 |
| Ac4 | −44 | −47.6 | −50.7 | −53.8 | −58.8 |
| Ac5 | −45.7 | −48.7 | −51.9 | −55.5 | −58.8 |
| Ac6 | −46.8 | −49.9 | −53.6 | −54.9 | −58.8 |
| Ac7 | −48 | −51.6 | −52.9 | −54.9 | −58.8 |
| Ac8 | −50 | −51.4 | −53.3 | −55.3 | −56.8 |
| Ac9 | −50 | −52 | −53.9 | −55.9 | −59.4 |
| Ac10 | −50 | −52 | −53.9 | −55.5 | −58.9 |
| Ac23 | −49 | −50 | −51.9 | −53.9 | −57 |
| Ac24 | −48 | −50 | −51.9 | −53.5 | −56.6 |
| Ac25 | −48.5 | −50.4 | −52 | −53.6 | −56 |
| Ac26 | −48.5 | −50.1 | −51.7 | −53.1 | −55.6 |

Results

The relationship between PMO molecule length and the predicted free binding energy (ΔG) to the DMD target mRNA was characterized to identify PMO oligonucleotides that retain maximal activity with sequence lengths less than 30-mer. Shorter sequences were predicted to have lower binding energy relative to the 30-mer parent sequence (Table 11). From the predicted free binding energy (ΔG (kcal/mol)) of PMOs in Table 11, 13 different PMOs targeting acceptor site positions between +2 and +10 with lengths between 26-28 oligonucleotides and apparent ΔG<−50 kcal/mol were selected for synthesis (see boxes in Table 11). They include PMOs (hEx_44_Ac24_28, hEx_44_Ac25_28, and hEx_44_Ac28) with predicted hDMD exon 44 skipping activities of >50% (data not shown). The sequence for each of the 13 PMOs are shown in Table 2. In addition, the shorter 25-mer PMO hEx_44_Ac2_25 with the predicted binding energy (ΔG) of −40.8 kcal/mol was included as an internal control (see Table 11). The selected 13 PMOs that ranged from 26- to 28-mer with free binding energy (ΔG) of <−50 kcal/mol and the 25-mer as control were synthesized for further in vitro screening for exon 44 skipping activity in primary and immortalized human skeletal muscle cells (hSkMCs).

In Vitro Exon 44 Skipping Screening Assay

A human myoblast cell line was obtained from the Association Institut de Myologie-Centre de Recherche en Myologie (UMRS 787 INSERM and Sorbonne Universite, France) through MyoBank, affiliated with EuroBioBank (authorization ref AC-2019-3502). The myoblast cell line was derived from the fascia lata of a 20-year old healthy male donor (AB1167C20FL). Cells were grown in Promocell Growth Medium (C-23160), supplemented with 5% FBS, at a cell density below 80%. Immortalized myoblasts were seeded into 24-well plates at 50000 cells/well in growth medium, grown to confluency and then differentiated. To induce differentiation into myotubes, cells were rinsed with DMEM, and then incubated in Differentiation Medium (DMEM, 50 ug/mL gentamycin, 10 µg/mL insulin) for 3-4 days. Cells were incubated without antibiotics for 24 h prior to transfection. The PMOs were synthesized by GeneTools and were formulated in water, heated at 65-70° C. for 5 minutes, diluted into warm medium together with 2 µM Endo-Porter (Gene Tools, #EP6P1-1) to facilitate PMO uptake into cells. The experiments were conducted with 0.3, 1, 3.3 and 10 µM PMO. After 48 hours, cells were harvested, and RNA isolation and cDNA synthesis was performed as previously described. For quantification by qPCR, PCR reactions were cycled 40 times and amplification of total and exon 44-skipped PCR products monitored using QuantStudio 6 or 7 Flex Real-Time PCR instruments (Applied Biosystems). Data were analyzed by QuantStudio™ Real-Time PCR Software v1.3 (Applied Biosystems). The % Exon 44-skipped mRNA was calculated as 100*2(CT(total)-CT(skipped)). Primers used: hDMD TaqMan assay Hs01049401_m1 (VIC-MGB, Thermo Fisher Scientific) or a custom-made TaqMan assay specific for the hDMD exon 43/45 junction (FAM-MGB, Forward: 5'-CTGTGGAAAGGGTGAAGCTA-3' (SEQ ID NO:90), Reverse: 5'-GACAAGGGAACTCCAGGATG-3' (SEQ ID NO:91), Probe: 5'-AGCTCTCTCCCAGCTTGATTTCCA-3' (SEQ ID NO:92). The dose-responses of the selected PMOs were fitted with a specific binding algorithm (single site). Total DMD mRNAs and exon 44 skipped DMD mRNAs were monitored by RT-qPCR. The dose-responses of the selected lead PMOs were fitted with a specific binding algorithm (single site).

Figure 3:
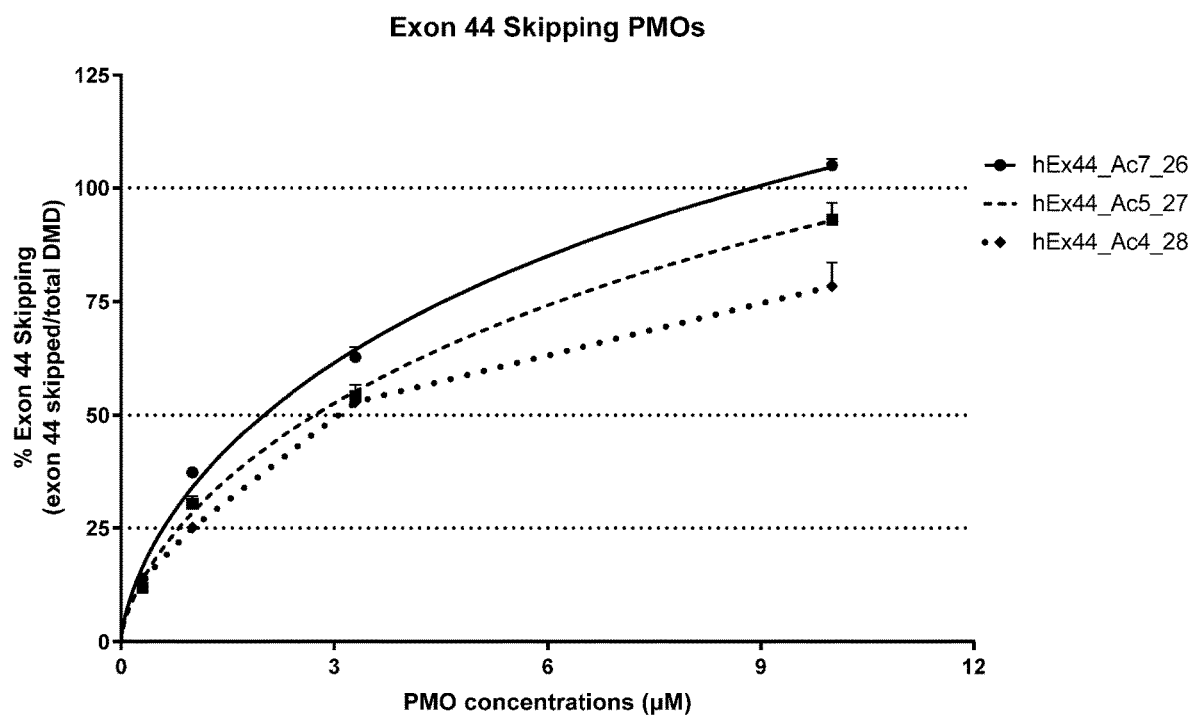
FIG. 3 is a plot of the dose response curve of the relative levels of exon 44 skipping in response to increasing concentrations of 3 different PMOs: hEx44_Ac7_26, hEx44_Ac5_27, and hEx44_Ac4_28.

The transfection of the selected PMOs into myotubes derived from healthy immortalized hSkMCs revealed that 3 different PMOs of various sizes had superior exon 44 skipping activity to that of the other PMOs. The 26-mer hEx44_Ac7_26 targeting the acceptor site 7, the 27-mer hEx44_Ac5_27 targeting the acceptor site 5, and the 28-mer hEx44_Ac4_28 targeting the acceptor site 4, show at least 75% or greater exon 44 skipping activity at the concentration of 10 µM (FIG. 3). Among the 3 PMOs, the PMO hEx44_Ac7-26-mer displayed the best length/activity ratio and was selected as the PMO molecule for further evaluations with in vitro and in vivo assays.

Based on the exon 44 skipping activity myotubes derived from healthy immortalized hSkMCs, the 26-mer PMO hEx44_Ac7-26 (5'-CGCCGCCATTTCTCAACAGATCTGTC-3' (SEQ ID NO: 118) had the best exon 44 skipping activity among the 3 PMOs.

Example 4: hEx44_Ac7_26 Induces Exon 44 Skipping Activity in Healthy Human Cells and DMD-Patient Derived Cells Immortalized and primary human Skeletal Muscle Cells (HSkMCs) (DMD cell: AB1323-immortalized; 47811-primary; 47898-primary; healthy cell: AB1167-immortalized; MB07-primary; MB09-primary) were obtained from Institut de Myologie (IoM), Paris, France (Immortalized) and from Besta Institute, Italy (primary). The 2 primary cells and 1 immortalized cell line are each derived from a DMD patient with an exon 45 deletion. Immortalized cells were grown in skeletal muscle growth media (Promocell, C-23160). Primary cells were grown in GM composed by DMEM+Glutamax (Gibco, Cat #10566-016), supplemented with 20% FBS (Corning), 1% Pen/Strep (ThermoFisher), 10 ug/ml Insulin (Sigma), 25 ng/ml hFGF (Stemcell Technologies), 10 ng/ml EGF (Stemcell Technologies) and plated on 1% Matrigel coated 24-well plates (20000 cells/well). Myoblasts were induced to form myotubes in DMEM+Glutamax (Gibco) supplemented with Skeletal Muscle Cell Differentiation Medium Supplement Mix (Promocell, Cat C-39366) and 1% Pen/Strep for 2 days according to the manufacturer's instructions. PMOs were synthesized by GeneTools. PMOs were formulated in water, heated at 65-70° C. for 5-10 minutes, diluted into warm medium. Cells were harvested 48 h post transfection. Cells were collected in Trizol and stored at −80° C. until processing for RNA isolation using Directzol-96 RNA isolation kit (Zymo) according to the manufacturer's instructions. Total RNA concentration was quantified spectroscopically. cDNA was prepared from 100-500 ng of purified RNA using the High-Capacity cDNA Reverse Transcription Kit (Applied Biosciences) in a SimpliAmp Thermal Cycler (Applied Biosystems). 40 ng of cDNA was partitioned into droplets, in triplicate, in the QX200 Automated Droplet Generator (BioRad) in combination with Taqman probes (ThermoFischer), 2×ddPCR Supermix (no dUTP) (BioRad), and BamHI restriction enzyme (BioRad). Following droplet generation, the mixture was loaded into a deep well C1000 Touch Thermal Cycler (BioRad) for PCR amplification. Absolute quantification of the target RNA molecules was measured in the QX200 Droplet Digital PCR System (BioRad) using the QX Manager software (BioRad). Percent Exon Skipping was calculated by normalizing the counts of the targeted exon to the total gene expression. Primers used: hDMD TaqMan assay Hs01049401_m1 (VIC-MGB, Thermo Fisher Scientific) or a custom-made TaqMan assay specific for the hDMD exon 43/45 junction (FAM-MGB, Forward:
(SEQ ID NO: 90)
5'-CTGTGGAAAGGGTGAAGCTA-3', Reverse:
(SEQ ID NO: 91)
5'-GACAAGGGAACTCCAGGATG-3', Probe:
(SEQ ID NO: 92))
5'-AGCTCTCTCCCAGCTTGATTTCCA-3'.

Results

Figure 4A:
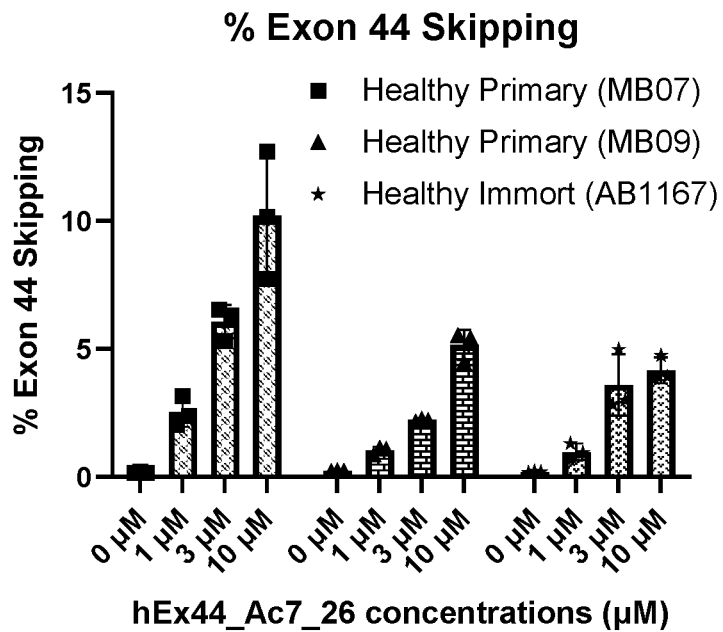
FIGS. 4A-4C illustrate plots of the dose response curve of the relative levels of exon 44 skipping in response to increasing concentrations of hEx44_Ac7_26 in myotube cells.
Figure 4B:
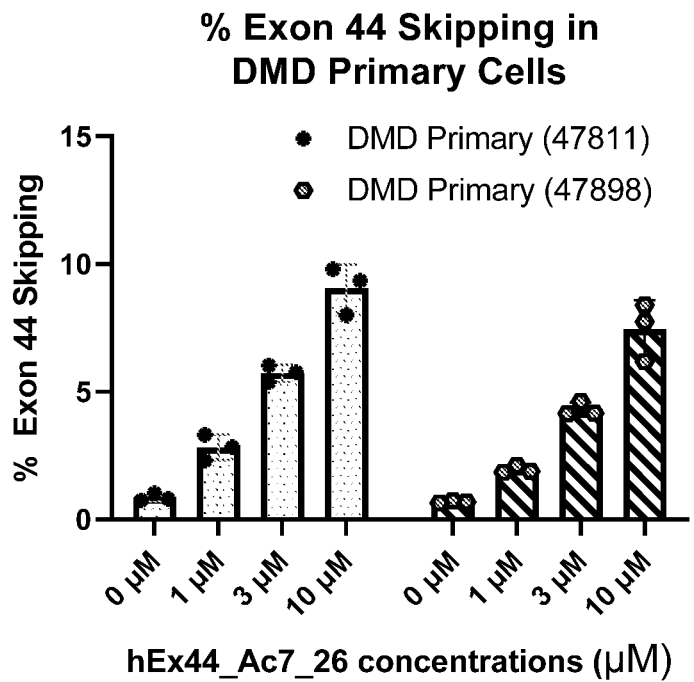
Figure 4C:
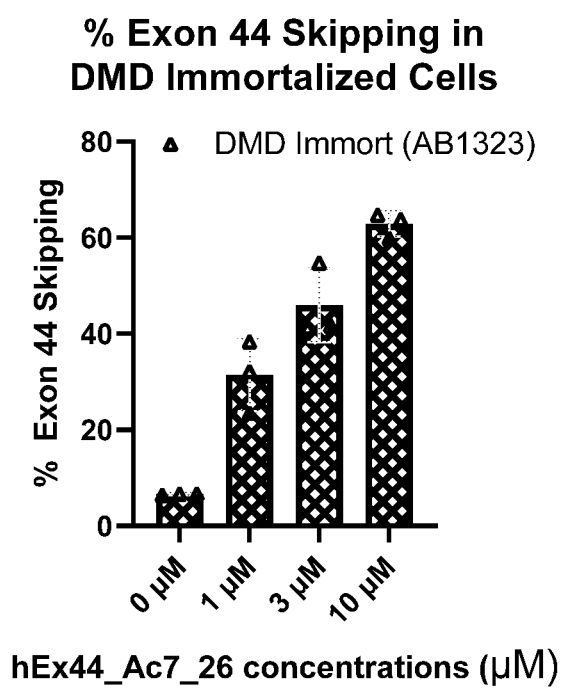

Exon 44 skipping activity in primary and immortalized healthy or DMD patient were evaluated using an exon 45 deletion derived myotubes transfected with hEx44_Ac7_26 by using ddPCR, which is a sensitive and highly accurate method for exon skipping quantification. These in vitro assays with hEx44_Ac7_26 were performed in myotubes derived from healthy and DMD patients harboring deletion of exon 45, which is amenable to exon 44 skipping therapy. As shown in FIG. 4C, the hEx44_Ac7_26 was able to induce exon 44 skipping in healthy and DMD-patient derived myotubes, and the exon 44 skipping activity in these cells was dose dependent. Interestingly, the results indicate that hEx44_Ac7_26 has higher exon 44 skipping activity in DMD cells than in the healthy cells. Exon 44 skipping activity in DMD-derived patient cells transfected with hEx44_Ac7_26 is up to 60% (FIG. 4C) while exon 44 skipping activity in healthy primary or immortalized cells is only up to 10% (FIGS. 4A-B). Without being bound to any particular theory, it may be that the skipping of a specific exon in dystrophin pre-mRNA in healthy cells could lead to a destabilization of the skipped mRNA and reduction of the total dystrophin mRNA while the hEx44_Ac7_26 induces frameshift restoration in DMD-derived patient cells and significant increase levels in skipped DMD transcripts, which highly correlate with the increase of total dystrophin mRNA expression levels to WT levels.

Overall, the hEx44_Ac7_26 was able to induce exon 44 skipping in healthy human cells and DMD patient-derived cells and exon 44 skipping activity in DMD-patient derived cells is greater than that of the healthy human cells.

Example 5: hEx44_Ac7_26 Induces Dystrophin Restoration in DMD-Patient Derived Myotubes Human primary myoblasts from healthy and DMD patients were amplified in Skeletal Muscle Growth medium (GM; Zenbio). At day 0, 15000 of human primary myoblasts per well were seeded in GM in 96-well MyoScreen CYTOO plates (CYTOO) coated with 10 μg/ml fibronectin (Invitrogen). The day after the seeding (day 1), growth medium was changed to differentiation medium (DM) composed of Dulbecco's Modified Eagle Medium: Nutrient Mixture F12 (DMEM/F12; Invitrogen), 2% horse serum (HS; GE Healthcare), 100 U/ml penicillin, and 100 μg/ml streptomycin (Invitrogen). At day 3 or day 6, compounds (PMOs and AOC) were added to the DMD cells without medium refresh for respectively 6 or 3 days. For PMO treatment, PMOs were synthesized by GeneTools. PMOs were heated for 5 minutes at 70° C. then cooled down slowly before addition to the medium. In this specific condition, Endo-Porter (GeneTools) was added simultaneously to the wells at 1 μM as delivery reagent. For each experiment a mock condition corresponding to vehicle +/− Endo-Porter was included to be used as negative control. At day 9, following 30 min fixation with 10% formalin (Sigma-Aldrich), myotubes were washed three times in Dulbecco's Phosphate-Buffered Saline (DPBS; Invitrogen) and permeabilized in 0.5% Triton X-100 (Sigma-Aldrich). After blocking in 1% bovine serum albumin (BSA; Sigma-Aldrich), cells were incubated with primary antibodies prepared in blocking solution: myotubes were stained with a troponin T specific antibody (ab45932 Abcam) or a myosin heavy chain specific antibody (14-6503-82 Thermo Fisher). C-terminal and N-terminal dystrophins were stained using respectively NCL-Dys2 and NCL-DysB antibodies (Leica). Secondary antibodies prepared in BSA 1% were then added with Hoechst 33342 to the wells after three washes with DPBS. Cells were finally washed three times in DPBS before acquisition. Quantitative microscopy was performed using the Operetta HCS imaging system with a 10×/0.3 NA objective (PerkinElmer). Images were analyzed using scripts developed in Acapella software (PerkinElmer), including customized segmentation of myotubes and nuclei. Myotubes were defined as areas positive for skeletal muscle differentiation marker troponin-T or myosin heavy chain (MHC) and conforming to specific filters optimized such as the min/max area, maximum orientation, minimum elongation, and min/max length of myotubes. A nuclei count was performed to define the total number of nuclei. The fusion index (FI) was calculated as the number of nuclei within the myotube staining area divided by the total number of nuclei and expressed as a percentage. After exclusion of myotubes touching the image borders, whole entire myotubes were finally used to extract myotube area and dystrophin mean intensity. Three healthy donors were included in each experiment. The mean intensity of dystrophin expression in these healthy myotubes was calculated and was used as a reference to assess the percentage of dystrophin restoration in DMD treated conditions calculated with the equation: % of dystrophin restoration= (IDMD treated−IDMDmock)/(Imean Healthy−IDMDmock). The percentage of positive myotubes was determined for each condition as the percentage of myotubes that expressed a dystrophin intensity superior to a threshold determined using mock respective condition.

Jess Capillary Western Blot

Patient derived Human Immortalized Skeletal Muscle Myoblasts with exon 45 deletion and Healthy Human Immortalized Skeletal Muscle Myoblasts were seeded on 1% Matrigel coated 24-well plates at a starting density of 20,000 cells/well in General Media (Skeletal Muscle Growth Media, Promocell c-23160, Gentamycin 5%, Gibco 15710064). Differentiation from myoblasts to myotubes was initiated 3 days after seeding by adding differentiation media (DMEM+Glutmax Gibco 10566-016, Insulin Promocell C-39366). Four days after differentiation and two days after PMO treatment myoblasts were collected. On ice, myoblasts went through two wash cycles of cold DPBS (Gibco 14190144) and then a 5 min incubation with M-PER lysis buffer (Thermo Fisher, 78501) and Halt Protease inhibitors (Thermo Fisher, 78429). Each well was then individually scraped for 20 seconds. The suspension was then collected and centrifuged at 14000 g for 15 minutes at 4° C. The supernatant was collected, and total protein concentration was measured using the Pierce BCA Protein assay kit (Thermo Scientific, 23227), according to the manufacturer's instructions. Samples were normalized to 300 μg/mL. Samples were then flash frozen in liquid nitrogen prior to quantification on the Jess Capillary Western Blot. Dystrophin protein quantification was measured by capillary western blot analysis using the protein simple Jess system with a 66-440 kDA Separation Module (Protein Simple, SM-W008), the Anti-Rabbit Detection Module (Protein- Simple, DM-001), and the Replex Module (Protein Simple, RP-001). Anti-dystrophin rabbit monoclonal antibody (Abcam, AB154168) specific dystrophin to was diluted 1:5000 in Antibody Dilution Buffer 2 (Protein Simple). The Anti-Rabbit Detection Module included blocking reagent (antibody diluent), HRP-conjugated anti-rabbit secondary antibody, and chemiluminescent substrate. The Replex Module included total protein normalization agent and a biotinylating agent. These reagents were plated following the manufactures protocol. Sample proteins diluted to appropriate concentration in sample buffer (100× diluted '10× Sample Buffer' from the Separation Module) were separated in the capillaries and were analyzed by chemiluminescent signal. Dystrophin signal was determined by the Compass Software (Protein Simple). The following criteria were used to discriminate low dystrophin signals from background: The peak signal-to-noise (S/N) ratio given by the software must be ≥10, and the peak height/baseline ratio (calculated manually from the peak height and baseline values given by the software) must be ≥3 (Adapted from Beekman et al., 2018). The signal was normalized to the total protein of each sample in the final quantification.

Results

Figure 5A:
FIGS. 5A-5C depict levels of dystrophin protein in response to increasing concentrations of hEx44_Ac7_26 in DMD patient-derived cultured myotubes.

The dystrophin restoration assay was performed using the MyoScreen platform. This platform uses optimized culture conditions for differentiation, maturation, and longevity of cultured myotubes, and allows the quantification of dystrophin restoration by immunofluorescence. FIG. 5A shows pictures of healthy cells and DMD patient-derived cells on the MyoScreen platform that were immunofluorescently stained for dystrophin positive fibers. Healthy cells (left panel) and DMD patient-derived cells transfected with hEx44_Ac7_26 (right panel) showed presence of dystrophin as indicated by the positive cellular immunofluorescence staining while the DMD patient-derived cells did not express any dystrophin as evidenced by the lack of immunofluorescence staining (central panel).

Figure 5B:
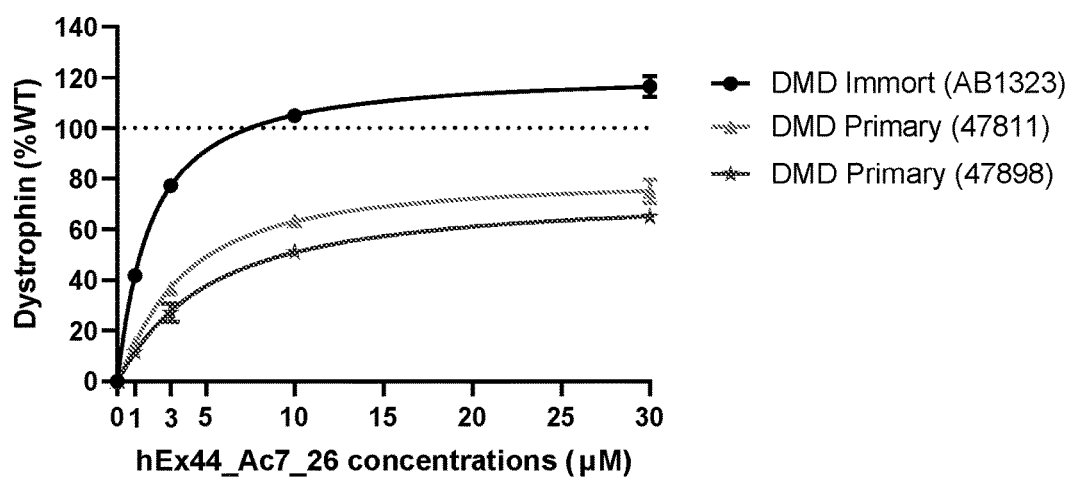

The quantitative analysis of immunofluorescence staining for dystrophin restoration in patient-derived cells transfected with PMO44 indicated that hEx44_Ac7_26 efficiently restored dystrophin in a dose-dependent manner in primary myotubes derived from 3 patients (2 primary cells and 1 immortalized cell line with an exon 45 deletion) (FIG. 5B). hEx44_Ac7_26 was able to restore up 100% of dystrophin in immortalized DMD patient derived cell line compared to that of wild-type cells (healthy primary cells) while hEx44_Ac7_26 was able to induce up 70% dystrophin restoration in the 2 primary DMD-patient derived cells compared to that of wild-type cells. Variation in the levels of dystrophin restoration may be dependent on the DMD donor cells.

Figure 5C:
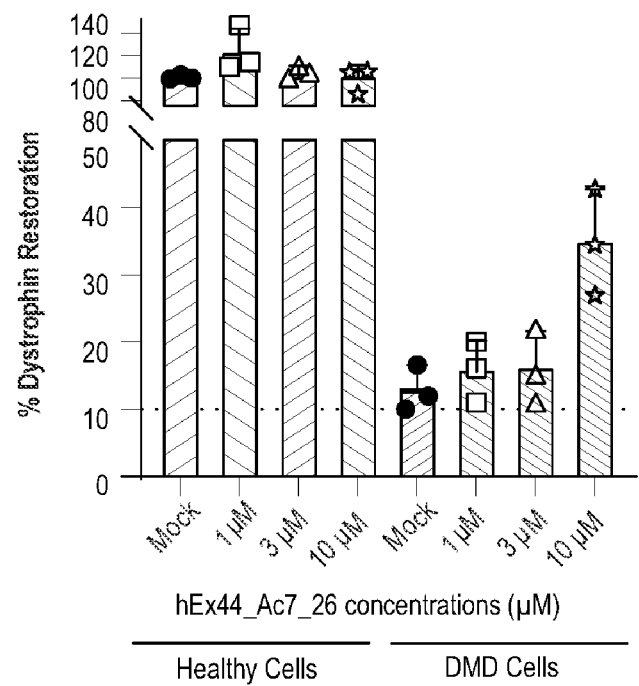

In addition, levels of dystrophin restoration were also quantified using Jess capillary western blotting in the healthy cells and immortalized DMD patient derived cells (FIG. 5C). The results indicate that hEx44_Ac7_26 is able to restore dystrophin expression levels in DMD-patient derived cells up to 50% compared the levels of dystrophin in healthy primary cells.

Overall, hEx44_Ac7_26 is able to restore dystrophin and DAPC in primary and immortalized DMD patient derived cells, and the degree of restoration of dystrophin was dependent on the DMD donor cells.

Example 6: In Vitro Dose-Dependent Exon 44 Skipping Activity in Wild Type Monkey Myotubes Treated with hEx44_Ac7_26

Wild type cynomolgus monkey primary skeletal muscle cells (Lot #SKM110414) were obtained from Worldwide Primate (WWP). Cells were grown in Zenbio GM media (SKM-M) and plated on 1% Matrigel (Corning) coated 24-well plates (20,000 cells/well). Myoblasts were induced to form myotubes in Zenbio DM media (SKM-D) for 2 days according to the manufacturer's instructions. PMOs were synthesized by GeneTools. PMOs were formulated in water, heated at 65-70° C. for 5-10 minutes, diluted into warm medium together with 1 µM Endo-Porter (Gene Tools, #EP6P1-1) to facilitate PMO uptake into cells. Cells were harvested 48 hours post-transfection. Cells were collected in Trizol and stored at −80° C. until processing for RNA isolation using Direct-zol-96 RNA isolation kit (Zymo) according to the manufacturer's instructions. Total RNA concentration was quantified spectroscopically. cDNA was prepared from 100-500 ng of purified RNA using the High-Capacity cDNA Reverse Transcription Kit (Applied Biosciences) in a SimpliAmp Thermal Cycler (Applied Biosystems). 40 ng of cDNA was partitioned into droplets, in triplicate, in the QX200 Automated Droplet Generator (Bio-Rad) in combination with 60× Taqman probes targeting skipped DMD spanning the exon 43-45 junction (ID No. AP7DUYJ) and total DMD spanning the exon 39-40 junction (ID No. Mf01049436 ml) (ThermoFischer), Taqman probes (ThermoFischer), 2×ddPCR Supermix (no dUTP) (BioRad), and BamHI restriction enzyme (BioRad). Following droplet generation, the mixture was loaded into a deep well C1000 Touch Thermal Cycler (BioRad) for PCR amplification. Absolute quantification of the target RNA molecules was measured in the QX200 Droplet Digital PCR System (BioRad) using the QX Manager software (BioRad). Percent of dystrophin exon skipping was calculated by normalizing the counts of the targeted exon to the total gene expression.

Results

Figure 6A:
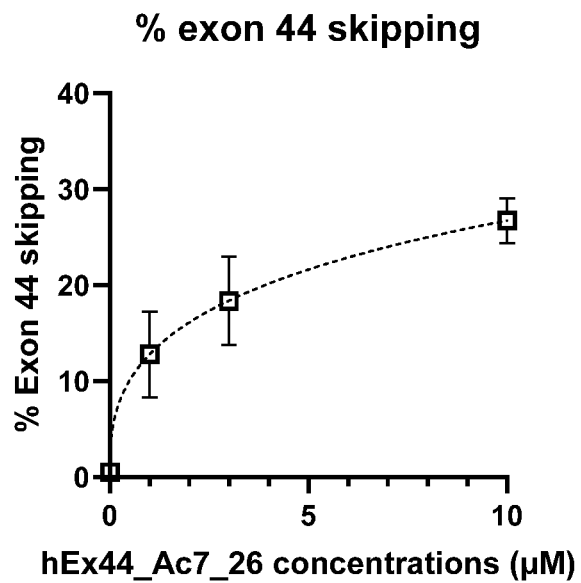
FIGS. 6A-6C are plots of the dose responses of the relative levels of exon 44 skipping in response to increasing concentrations of hEx44_Ac7_26 in non-human primate myotubes.
Figure 6B:
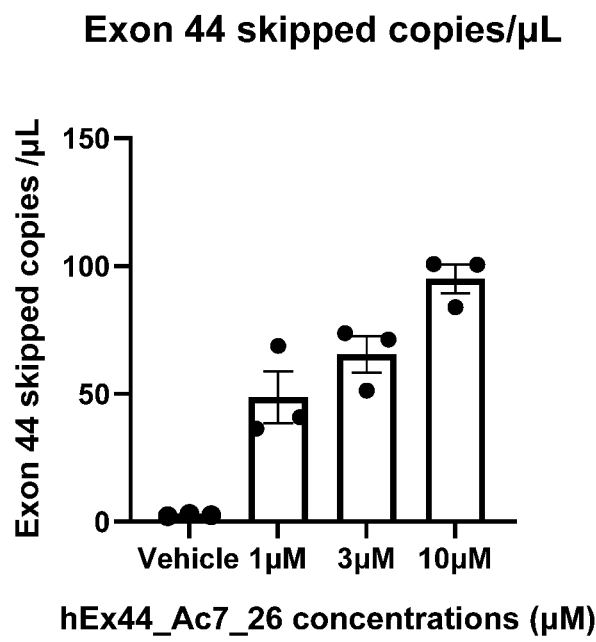
Figure 6C:
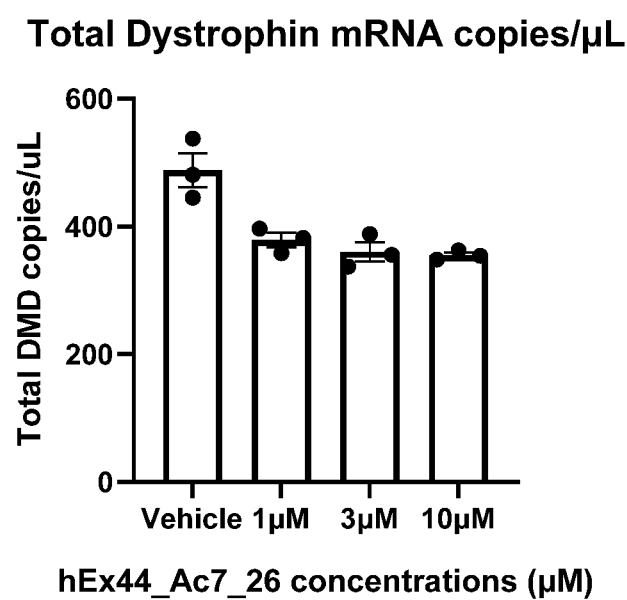

Since the acceptor sequence for exon 44 in monkey DMD gene is identical to the human one, we evaluated exon 44 skipping activity in primary healthy monkey myotubes treated with increasing concentrations of hEx44_Ac7_26 using ddPCR. As shown in FIGS. 6A-B, hEx44_Ac7_26 induces a strong dose-dependent response of exon 44 skipping in primary healthy monkey myotubes in vitro. hEx44_Ac7_26 induces greater than 25% exon 44 skipping (FIG. 6A) and up to 100 exon 44 skipped copies/µl in healthy monkey myotubes (FIG. 6B). Interestingly, hEx44_Ac7_26 reduced the total number of DMD copies/µl to less than 400 when compared to the dystrophin mRNA copies in the control group. Similar to healthy human myotubes (see Example 4), the reduction in total dystrophin mRNA copies in healthy monkey cells transfected by hEx44_Ac7_26 was up to 25% compared to DMD cells and may be due to out-of-frame mutation of the dystrophin mRNA resulting in the destabilization of the skipped exon mRNA.

Overall, these results demonstrate that hEx44_Ac7_26 is able to reduce DMD mRNA levels in primary healthy monkey cells and exon 44 skipping induced by PMO in healthy cells decrease DMD gene expression that may be caused by out-of-frame mutation of the DMD mRNA.

Example 7: Biodistribution of Exon 44 Skipping Copies in Muscle and Non-Muscle Tissues of Cynomolgus Monkey that have been Administered a Single Dose of hEx44_Ac7_26-AOC at the Dose of 159.9 mg/kg at Day 0 Corresponding to the PMO (hEx44-Ac7-26) Dose Level of 30 mg/kg Scheme 1: Synthesis and Purification of hEx44_Ac7_26-AOC An anti-human transferrin receptor antibody was produced. The hEx44_Ac7_26 PMO was synthesized by Gene- Tools. Antibody (10 mg/ml) in borate buffer (25 mM sodium tetraborate, 25 mM NaCl, 1 mM Diethylene triamine pentaacetic acid, pH 8.0) was reduced by adding 4 equivalents of tris(2-carboxyethyl)phosphine (TCEP) in water and incubating at 37° C. for 4 hours. 4(N-Maleimidomethyl)cyclohexanecarboxylic acid N-hydroxysuccinimide ester (SMCC) was coupled to the primary amine on the 3' end of the hEx44_Ac7_26 PMO by incubating the hEx44_Ac7_26 PMO (50 mg/ml) in DMSO with 10 equivalents of SMCC (10 mg/ml) in DMSO for one hour. Unconjugated SMCC was removed by ultrafiltration using Amicon Ultra-15 centrifugal filter units with a MWCO of 3 kDa. The hEx44_Ac7_26 PMO-SMCC was washed three times with acetate buffer (10 mM sodium acetate, pH 6.0) and used immediately. The reduced antibody was mixed with 2.25 equivalents of hEx44_Ac7_26 PMO-SMCC and incubated overnight at 4° C. The pH of the reaction mixture was then reduced to 7.5 and 8 equivalents of N-Ethylmaleimide was added to the mixture at room temperature for 30 minutes to quench unreacted cysteines.

The reaction mixture was purified with an AKTA Explorer FPLC using HIC method-1. Dependent on the conjugate, fractions containing either conjugates with a drug to antibody ratio of one (DAR 1), two (DAR 2), three (DAR 3), four (DAR 4), five (DAR 5), six (DAR 6), seven (DAR 7), eight (DAR 8) or fractions containing conjugates with a drug to antibody ratio of 3+(DAR 3+), 4+(DAR 4+), 5+(DAR 5+), 6+(DAR 6+), 7+(DAR 7+), (DAR 8+), or fractions containing either conjugates with an average drug to antibody ratio of one (DAR 1), two (DAR 2), three (DAR 3), four (DAR 4), five (DAR 5), six (DAR 6), seven (DAR 7), or eight (DAR 8) were combined and concentrated with Amicon Ultra-15 centrifugal filter units with a MWCO of 50 kDa. Concentrated conjugates were buffer exchanged with PBS (pH 7.4) using Amicon Ultra-15 centrifugal filter units prior to analysis.

Hydrophobic Interaction Chromatography (HIC) Method-1
   Column: GE, HiScreen Butyl HP, 4.7 ml
     Solvent A: 50 mM phosphate buffer, 0.7M Ammonium Sulfate, pH 7.0; Solvent B: 80% 50 mM phosphate buffer, 20% IPA, pH 7.0; Flow Rate: 1.0 ml/min

| Gradient: | | |
|---|---|---|
| % A | % B | Column Volume |
| 100 | 0 | 1 |
| 70 | 30 | 25 |
| 0 | 100 | 1 |
| 0 | 100 | 2 | hEx44_Ac7_26-AOC was quantified via BCA and analyzed by HIC (Avg DAR≈3.8-4.0),
SEC (3.3% HMW), and LAL (<0.025 EU/mg anti-transferrin receptor antibody). The product was stored at 4° C.

Scheme 2: Synthesis and Purification of hEx44_Ac7_26-AOC

An anti-human transferrin receptor antibody was produced. The hEx44_Ac7_26 PMO was synthesized. Antibody (20.4 mg/ml) in citrate buffer (50 mM sodium citrate, 300 mM sucrose pH 6.5) was combined with ethylenediaminetetraacetic acid (EDTA, 0.5 M, 0.591 mL) and was reduced by adding 2 equivalents of tris(2-carboxyethyl)phosphine (TCEP) in water and incubating at 37° C. for 2 hours. 4(N-Maleimidomethyl)cyclohexanecarboxylic acid N-hydroxysuccinimide ester (SMCC) was coupled to the primary amine on the 3' end of the hEx44_Ac7_26 PMO by incubating the hEx44_Ac7_26 PMO (50 mg/ml) in 50 mM phosphate buffer pH 7.2 with 3 equivalents of SMCC (50 mg/ml) in DMSO for one hour. Unconjugated SMCC was removed by tangential flow filtration (TFF) with a membrane MWCO of 3 kDa with acetate buffer (10 mM sodium acetate, pH 6.0). The reduced antibody was mixed with 4.75 equivalents of hEx44_Ac7_26 PMO-SMCC and incubated 1 hour at room temperature. N-Ethylmaleimide (10 equivalents, 15 mg/ml in DMSO, 25 mg) was added to the mixture at room temperature for 30 minutes to quench unreacted cysteines. The reaction was diluted to 1 L with endotoxin free water. Excess PMO and NEM were removed via SCX purification (GE SP/HP 16 10 resin) using SCX method-1. The combined fractions were buffer exchanged via TFF into citrate buffer (50 mM sodium citrate, 60 mM NaCl, pH 5.5) and concentrated to approximately 25 mg Ab/mL. The solution was sterile filtered with a 0.22 um membrane.

Strong Cation Chromatography (SCX) Method-1
   Column: GE HiScale 50, HiPrep SP HP, 200 ml
   Solvent A: 25 mM acetate, 25 mM PB, pH 6; Solvent B: 25 mM acetate, 25 mM PB, pH 6, 0.5 mM NaCl; Flow Rate: 30 ml/min

| Gradient: | | |
|---|---|---|
| % A | % B | Column Volume |
| 100 | 0 | 3 |
| 40 | 60 | 1.5 |
| 0 | 100 | 0.2 |
| 0 | 100 | 1 | hEx44_Ac7_26-AOC was quantified via BCA and analyzed by HIC (Avg DAR≈3.8-4.0),
SEC (3.3% HMW), and LAL (<0.025 EU/mg anti-transferrin receptor antibody). The product was stored at 4° C.

Scheme 3: Synthesis and Purification of hEx44_Ac7_26-AOC

Figure 7:
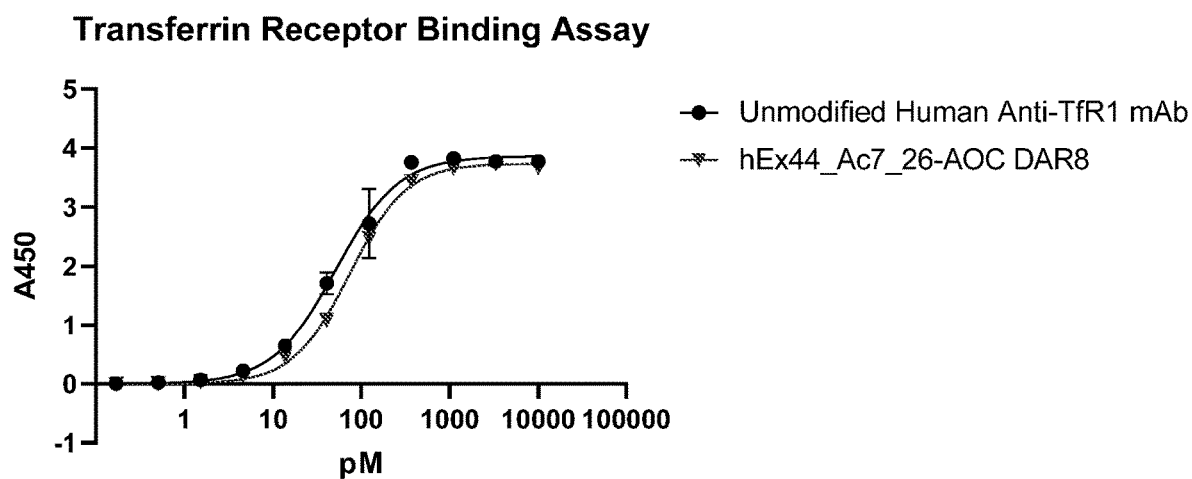
FIG. 7 is a graph illustrating the binding assay of the DAR8 hEx44_Ac7_26 AOC or the unmodified anti-transferrin receptor monoclonal antibody to the transferrin receptor by ELISA.

An anti-human transferrin receptor antibody was produced in citrate buffer (50 mM sodium citrate, 300 mM sucrose pH 6.5). The hEx44_Ac7_26 PMO-SMCC was synthesized by coupling 4(N-Maleimidomethyl)cyclohexanecarboxylic acid N-hydroxysuccinimide ester (SMCC) to the primary amine on the 3' end of the hEx44_Ac7_26 PMO. Ethylenediaminetetraacetic acid (EDTA, 0.5 M, 0.05 mL) was added to the antibody and the solution was thoroughly mixed. The antibody was reduced by the addition of tris(2-carboxyethyl)phosphine (TCEP, 20 mg/mL in H20, 10 equiv., 19.5 mg, 0.973 mL) and the solution was incubated at 37° C. for two hours. The reduced antibody solution was removed from the incubator and cooled to room temperature. The hEx44_Ac7_26 PMO-SMCC solution (12 equiv., 27.4 mg/ml in 10 mM acetate pH 6, 26.1 mL) was added to the reduced antibody solution and mixed thoroughly. The reaction proceeded at room temperature for one hour. n-ethylmaleimide (NEM) solution (10 equiv., 25 mg/mL in DMSO, 8.5 mg, 0.34 ml) was added to the reaction mixture and the reaction proceeded for 30 minutes at room temperature to quench unreacted cysteines. The reaction mixture was diluted to 0.2 L with endotoxin free water. Excess PMO and NEM were removed via strong cation chromatography purification SCX method-1. The combined fractions were buffer exchanged via using spin filtration into histidine buffer (20 mM histidine, 10 mM methionine, 120 mM sucrose, pH 6.0) and was quantified via a BCA assay (0.79 g, 79% yield). The solution was sterile filtered with a 0.22 μm membrane. PMO44-AOC was quantified via BCA and analyzed by hydrophobic interaction chromatography (average DAR≈8), size exclusion chromatography (3.3% HMW), reducing capillary gel electrophoresis (average DAR≈7.8-8.0), and ELISA binding affinity to the human transferrin receptor (74.5 pM Kd). The affinity of hEx44_Ac7_26-AOC DAR8 AOC was equivalent to unconjugated anti-transferrin receptor antibody as shown in FIG. 7.

Exon 44 Skipping Assay

Cynomolgus monkeys received a single intravenous (IV) infusion of hEx44_Ac7_26-AOC at 159.9 mg/kg, which corresponded to a PMO dose level of 30 mg/kg. Muscle tissue and non-muscle biopsy samples were obtained from the cynomolgus monkeys on day 43/44 (prior to necropsy). In the vehicle control group, the animals did not receive any of hEx44_Ac7_26-AOC. 4 male animals per group were analyzed.

Cynomolgus monkey muscle tissue and non-muscle samples ranging from 20-50 mg were homogenized in 1 mL of TRIzol (Thermo Fisher) on the OMNI Bead Ruptor Elite system (OMNI International). RNA was isolated from tissue homogenate supernatant using the Direct-zol-96 RNA kit (Zymo Research) according to the manufacturer's instructions. 250 ng of purified RNA was converted to cDNA using the High-Capacity cDNA Reverse Transcription Kit (Applied Biosystems) and SimpliAmp Thermal Cycler (Applied Biosystems). ddPCR was performed on 50 ng of cDNA in a reaction containing the commercially available Total DMD Taqman Assay (Mf01049436_m1 VIC-MGB, Thermo Fisher), custom Skipped DMD Taqman Assay (Forward Primer: AAGGACCGACAAGGGAACT (SEQ ID NO: 93); Probe (FAM-MGB): TTCTGACAACAGTTTGCCGCTGC (SEQ ID NO: 94); Reverse Primer: GCTGAATTAT-TTCTTCCGCAGTTG (SEQ ID NO: 95), Thermo Fisher), ddPCR Supermix for probes (no dUTP, Bio-Rad), BamHI-HF restriction enzyme (New England BioLabs), and Ambion nuclease free water (Thermo Fisher). Each sample, run in triplicates, was partitioned into droplets in the QX200 Automated Droplet Generator (Bio-Rad). Following droplet generation, samples were transferred to a C1000 Touch Thermal Cycler with 96-Deep Well Reaction Module (Bio-Rad). After PCR amplification, samples were loaded into the QX200 Droplet Reader (Bio-Rad). Data were analyzed using QX Manager Software, Standard Edition, Version 1.2 (Bio-Rad). Discrimination between positive and negative droplets was achieved by manually applying a fluorescence amplitude threshold. Percent exon skipping was calculated as 100*(number of skipped exon 44 copies per μL/Total DMD copies per μL).

Results

Figure 8:
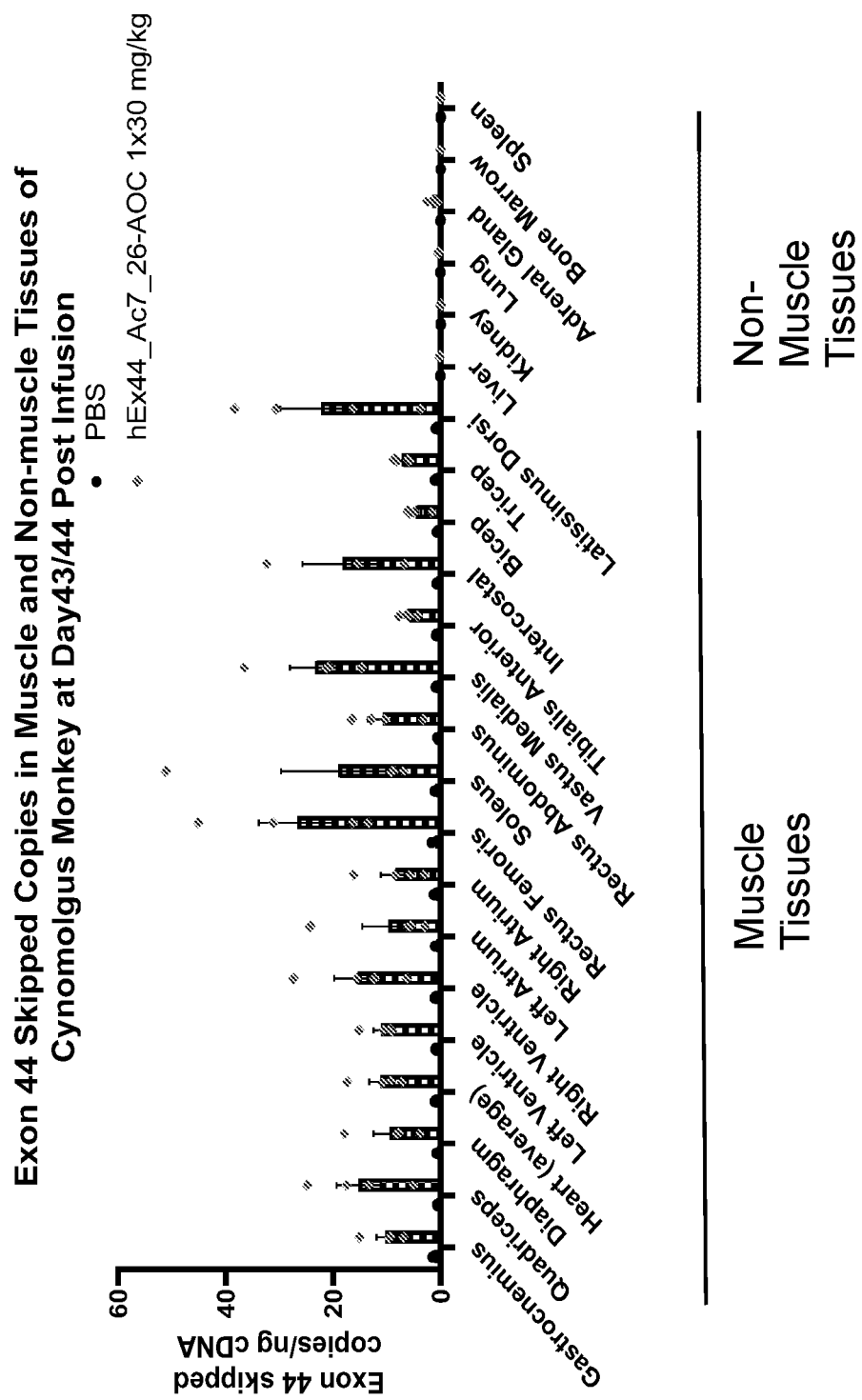
FIG. 8 is a bar graph illustrating the number of exon 44 skipped copies in muscle and non-muscles tissues obtained from cynomolgus monkeys at day 43/44 that have been administered a single infusion of hEx44_Ac7_26-AOC at the dose of 159.9 mg/kg at day 0.

Cynomolgus monkeys received a single IV infusion of hEx44-Ac7-26-AOC at Day 0 at the dose of 159.9 mg/kg at Day 0 corresponded to the PMO (hEx44-Ac7-26) dose level of 30 mg/kg. Muscle and non-muscle tissues from the animals were collected at 43/44 days post-dose and the number of exon 44 skipped copies in these tissues was measured by ddPCR. No exon 44 skipping activity was detected in the PBS injected samples. After 44 days post IV infusion of a single dose of hEx44_Ac7_26-AOC at 159.9 mg/kg, exon 44 skipping activity was detected in all muscle tissues, but it was not detected in non-muscle tissues, which include the liver and kidney (see FIG. 8). Exon 44 skipping activity in muscles was detected in skeletal muscles as well as cardiac muscles. The highest level of exon 44 skipping activity in muscle tissue was detected in the rectus femoris muscle with greater than 25 exon 44 skipped copies per ng of cDNA, and the lowest one was detected in the biceps with less than 5 copies per ng of cDNA. In addition, exon 44 skipping activities in the atria and ventricles of the heart were measured with an average of approximately 7 exon 44 skipped copies per ng of cDNA. These results indicate that hEx44_Ac7_26-AOC specifically targets muscle tissues, both skeletal and cardiac muscles, and induces exon 44 skipping in these specific tissues. Exon 44 skipping activities were detected 43 days after the single IV infusion of hEx44_Ac7_26-AOC confirming its long-lasting activity in the targeted tissues. Overall, exon 44 skipping activity induced by hEx44_Ac7_26-AOC is specific to muscle tissues, and the hEx44_Ac7_26-AOC has long lasting exon 44 skipping activities in muscle tissues.

While preferred aspects of the present disclosure have been shown and described herein, it will be obvious to those skilled in the art that such aspects are provided by way of example only. Numerous variations, changes, and substitutions will now occur to those skilled in the art without departing from the disclosure. It should be understood that various alternatives to the aspects of the disclosure described herein may be employed in practicing the disclosure. It is intended that the following claims define the scope of the disclosure and that methods and structures within the scope of these claims and their equivalents be covered thereby.

What is claimed is:

1. A phosphorodiamidate morpholino oligonucleotide (PMO) conjugate comprising an anti-transferrin receptor antibody or antigen binding fragment thereof conjugated to a PMO molecule, wherein the PMO molecule consists of a sequence selected from the group consisting of SEQ ID NOs: 116-119.

2. The PMO conjugate of claim 1, wherein the anti-transferrin receptor antibody or antigen binding fragment thereof comprises a humanized antibody or antigen binding fragment thereof, chimeric antibody or antigen binding fragment thereof, monoclonal antibody or antigen binding fragment thereof, monovalent Fab', divalent $Fab_2$, single chain variable fragment (scFv), diabody, minibody, nanobody, single domain antibody (sdAb), or camelid antibody or antigen binding fragment thereof.

3. The PMO conjugate of claim 1, wherein the PMO molecule is conjugated to the anti-transferrin receptor antibody or antigen binding fragment thereof via a linker.

4. The PMO conjugate of claim 3, wherein the linker is a cleavable linker or a non-cleavable linker, wherein the linker is a heterobifunctional linker or a homobifunctional linker, and wherein the linker comprises a maleimide group, a dipeptide moiety, a benzoic acid group or derivatives thereof, a $C_1$-$C_6$ alkyl group, or a combination thereof.

5. The PMO conjugate of claim 1, wherein the PMO conjugate has a PMO molecule to antibody ratio (DAR) of 1:1, 2:1, 3:1, 4:1% 5:1, 6:1, 7:1, 8:1 or higher.

6. The PMO conjugate of claim 1, wherein the PMO conjugate has an average DAR of 1, 2, 3, 4, 5, 6, 7, 8 or higher.

7. The PMO conjugate of claim 1, wherein the PMO conjugate has an average DAR in the range of 3.5-4.5 or 7.5-8.5.

8. The PMO conjugate of claim 1, wherein the PMO conjugate has an average DAR of 4 or 8.

9. The PMO conjugate of claim 1, wherein the PMO conjugate has a DAR of 4 or 8.

10. A method of treating muscular dystrophy in a subject in need thereof comprising administering to said subject a phosphorodiamidate morpholino oligonucleotide (PMO) conjugate comprising an anti-transferrin receptor antibody or antigen binding fragment thereof conjugated to a PMO molecule comprising a sequence selected from the group consisting of SEQ ID NOs: 116-119, wherein the PMO molecule induces exon 44 skipping in a pre-mRNA transcript of a DMD gene to generate an mRNA transcript encoding a truncated dystrophin protein.

11. The method of claim 10, wherein the PMO molecule is delivered into a muscle cell.

12. The method of claim 10, wherein the anti-transferrin receptor antibody or antigen binding fragment thereof comprises a humanized antibody or antigen binding fragment thereof, chimeric antibody or antigen binding fragment thereof, monoclonal antibody or antigen binding fragment thereof, monovalent Fab', divalent $Fab_2$, single chain variable fragment (scFv), diabody, minibody, nanobody, single domain antibody (sdAb), or camelid antibody or antigen binding fragment thereof.

13. The method of claim 10, wherein the PMO molecule is conjugated to the anti-transferrin receptor antibody or antigen binding fragment thereof via a linker.

14. The method of claim 13, wherein the linker is a cleavable linker or a non-cleavable linker, wherein the linker is a heterobifunctional linker or a homobifunctional linker, and wherein the linker comprises a maleimide group, a dipeptide moiety, a benzoic acid group or derivatives thereof, a $C_1$-$C_6$ alkyl group, or a combination thereof.

15. The method of claim 10, wherein the PMO conjugate has an average of PMO molecule to antibody ratio (DAR) of 1:1, 2:1, 3:1, 4:1, 5:1, 6:1, 7:1, or 8:1.

16. The method of claim 10, wherein the PMO conjugate has an average DAR in the range of 3.5-4.5 or 7.5-8.5.

17. The method of claim 10, wherein the PMO conjugate has an average DAR of 4 or 8.

18. The method of claim 10, wherein the PMO conjugate is administered parenterally.

19. The method of claim 10, wherein the truncated dystrophin protein modulates muscular dystrophy.

20. The method of claim 19, wherein the muscular dystrophy is Duchenne muscular dystrophy or Becker muscular dystrophy.

21. A method of inducing exon 44 skipping in a targeted pre-mRNA transcript of DMD gene, comprising:
  a) contacting a muscle cell with a phosphorodiamidate morpholino oligonucleotide (PMO)-antibody conjugate, wherein the PMO-antibody conjugate comprises an anti-transferrin receptor antibody or antigen binding fragment thereof, and a PMO molecule consisting of a sequence selected from the group consisting of SEQ ID NOs: 116-119; wherein the PMO molecule induces exon 44 skipping in the targeted pre-mRNA transcript, and wherein the PMO-antibody conjugate is preferentially delivered into the muscle cell;
  b) hybridizing the PMO molecule to the targeted pre-mRNA transcript to induce exon 44 skipping in the targeted pre-mRNA transcript; and
  c) translating an mRNA transcript produced from the targeted pre-mRNA transcript processed in step b) in the muscle cell to generate a truncated dystrophin protein.

* * * * *

SEQUENCE LISTING

```
Sequence total quantity: 134
SEQ ID NO: 1            moltype =    length =
SEQUENCE: 1
000

SEQ ID NO: 2            moltype =    length =
SEQUENCE: 2
000

SEQ ID NO: 3            moltype =    length =
SEQUENCE: 3
000

SEQ ID NO: 4            moltype =    length =
SEQUENCE: 4
000
```

```
SEQ ID NO: 5           moltype =    length =
SEQUENCE: 5
000

SEQ ID NO: 6           moltype =    length =
SEQUENCE: 6
000

SEQ ID NO: 7           moltype =    length =
SEQUENCE: 7
000

SEQ ID NO: 8           moltype =    length =
SEQUENCE: 8
000

SEQ ID NO: 9           moltype =    length =
SEQUENCE: 9
000

SEQ ID NO: 10          moltype =    length =
SEQUENCE: 10
000

SEQ ID NO: 11          moltype =    length =
SEQUENCE: 11
000

SEQ ID NO: 12          moltype = AA   length = 17
FEATURE                Location/Qualifiers
source                 1..17
                       mol_type = protein
                       organism = synthetic construct
VARIANT                6
                       note = N or Q
SEQUENCE: 12
EINPIXGRSN YAZKFQG                                                  17

SEQ ID NO: 13          moltype = AA   length = 11
FEATURE                Location/Qualifiers
source                 1..11
                       mol_type = protein
                       organism = synthetic construct
VARIANT                8
                       note = N or S
SEQUENCE: 13
RTSENIYXNL A                                                        11

SEQ ID NO: 14          moltype = AA   length = 7
FEATURE                Location/Qualifiers
source                 1..7
                       mol_type = protein
                       organism = synthetic construct
VARIANT                2
                       note = A or G
VARIANT                7
                       note = D or E
SEQUENCE: 14
AXTNLAX                                                             7

SEQ ID NO: 15          moltype = AA   length = 10
FEATURE                Location/Qualifiers
source                 1..10
                       mol_type = protein
                       organism = synthetic construct
VARIANT                10
                       note = May be deleted
SEQUENCE: 15
QHFWGTPLTF                                                          10

SEQ ID NO: 16          moltype = AA   length = 7
FEATURE                Location/Qualifiers
source                 1..7
                       mol_type = protein
                       organism = synthetic construct
VARIANT                7
                       note = D or E
SEQUENCE: 16
```

```
AATNLAX                                                                  7

SEQ ID NO: 17           moltype = AA  length = 9
FEATURE                 Location/Qualifiers
source                  1..9
                        mol_type = protein
                        organism = synthetic construct SEQUENCE: 17
YTFTNYWMH                                                                9

SEQ ID NO: 18           moltype = AA  length = 17
FEATURE                 Location/Qualifiers
source                  1..17
                        mol_type = protein
                        organism = synthetic construct SEQUENCE: 18
EINPINGRSN YAQKFQG                                                      17

SEQ ID NO: 19           moltype = AA  length = 7
FEATURE                 Location/Qualifiers
source                  1..7
                        mol_type = protein
                        organism = synthetic construct SEQUENCE: 19
GTRAMHY                                                                  7

SEQ ID NO: 20           moltype = AA  length = 17
FEATURE                 Location/Qualifiers
source                  1..17
                        mol_type = protein
                        organism = synthetic construct SEQUENCE: 20
EINPINGRSN YAEKFQG                                                      17

SEQ ID NO: 21           moltype = AA  length = 17
FEATURE                 Location/Qualifiers
source                  1..17
                        mol_type = protein
                        organism = synthetic construct SEQUENCE: 21
EINPIQGRSN YAEKFQG                                                      17

SEQ ID NO: 22           moltype = AA  length = 11
FEATURE                 Location/Qualifiers
source                  1..11
                        mol_type = protein
                        organism = synthetic construct SEQUENCE: 22
RTSENIYNNL A                                                            11

SEQ ID NO: 23           moltype = AA  length = 7
FEATURE                 Location/Qualifiers
source                  1..7
                        mol_type = protein
                        organism = synthetic construct SEQUENCE: 23
AATNLAD                                                                  7

SEQ ID NO: 24           moltype = AA  length = 9
FEATURE                 Location/Qualifiers
source                  1..9
                        mol_type = protein
                        organism = synthetic construct SEQUENCE: 24
QHFWGTPLT                                                                9

SEQ ID NO: 25           moltype = AA  length = 7
FEATURE                 Location/Qualifiers
source                  1..7
                        mol_type = protein
                        organism = synthetic construct SEQUENCE: 25
AATNLAE                                                                  7

SEQ ID NO: 26           moltype = AA  length = 10
FEATURE                 Location/Qualifiers
source                  1..10
                        mol_type = protein
                        organism = synthetic construct
```

```
SEQUENCE: 26
QHFWGTPLTF                                                              10

SEQ ID NO: 27           moltype = AA  length = 11
FEATURE                 Location/Qualifiers
source                  1..11
                        mol_type = protein
                        organism = synthetic construct
SEQUENCE: 27
RTSENIYSNL A                                                            11

SEQ ID NO: 28           moltype = AA  length = 7
FEATURE                 Location/Qualifiers
source                  1..7
                        mol_type = protein
                        organism = synthetic construct
SEQUENCE: 28
AGTNLAD                                                                 7

SEQ ID NO: 29           moltype = AA  length = 116
FEATURE                 Location/Qualifiers
source                  1..116
                        mol_type = protein
                        organism = synthetic construct
SEQUENCE: 29
QVQLVQSGAE VKKPGASVKV SCKASGYTFT NYWMHWVRQA PGQGLEWMGE INPINGRSNY        60
AQKFQGRVTL TVDTSISTAY MELSRLRSDD TAVYYCARGT RAMHYWGQGT LVTVSS            116

SEQ ID NO: 30           moltype = AA  length = 116
FEATURE                 Location/Qualifiers
source                  1..116
                        mol_type = protein
                        organism = synthetic construct
SEQUENCE: 30
QVQLVQSGAE VKKPGASVKV SCKASGYTFT NYWMHWVRQA PGQGLEWIGE INPINGRSNY        60
AEKFQGRVTL TVDTSSSTAY MELSRLRSDD TAVYYCARGT RAMHYWGQGT LVTVSS            116

SEQ ID NO: 31           moltype = AA  length = 116
FEATURE                 Location/Qualifiers
source                  1..116
                        mol_type = protein
                        organism = synthetic construct
SEQUENCE: 31
QVQLVQSGAE VKKPGASVKV SCKASGYTFT NYWMHWVRQA PGQGLEWMGE INPIQGRSNY        60
AEKFQGRVTL TVDTSSSTAY MELSSLRSED TATYYCARGT RAMHYWGQGT LVTVSS            116

SEQ ID NO: 32           moltype = AA  length = 116
FEATURE                 Location/Qualifiers
source                  1..116
                        mol_type = protein
                        organism = synthetic construct
SEQUENCE: 32
QVQLVQSGAE VKKPGASVKV SCKASGYTFT NYWMHWVRQA PGQGLEWMGE INPINGRSNY        60
AEKFQGRVTL TVDTSSSTAY MELSSLRSED TATYYCARGT RAMHYWGQGT LVTVSS            116

SEQ ID NO: 33           moltype = AA  length = 116
FEATURE                 Location/Qualifiers
source                  1..116
                        mol_type = protein
                        organism = synthetic construct
SEQUENCE: 33
QVQLQQPGAE LVKPGASVKL SCKASGYTFT NYWMHWVKQR PGQGLEWIGE INPINGRSNY        60
GERFKTKATL TVDKSSSTAY MQLSSLTSED SAVYYCARGT RAMHYWGQGT SVTVSS            116

SEQ ID NO: 34           moltype = AA  length = 107
FEATURE                 Location/Qualifiers
source                  1..107
                        mol_type = protein
                        organism = synthetic construct
SEQUENCE: 34
DIQMTQSPSS LSASVGDRVT ITCRTSENIY NNLAWYQQKP GKSPKLLIYA ATNLADGVPS        60
RFSGSGSGTD YTLTISSLQP EDFATYYCQH FWGTPLTFGG GTKVEIK                     107

SEQ ID NO: 35           moltype = AA  length = 107
FEATURE                 Location/Qualifiers
source                  1..107
                        mol_type = protein
                        organism = synthetic construct
SEQUENCE: 35
```

```
DIQMTQSPSS LSASVGDRVT ITCRTSENIY NNLAWYQQKP GKAPKLLIYA ATNLADGVPS    60
RFSGSGSGTD YTLTISSLQP EDFATYYCQH FWGTPLTFGG GTKVEIK                 107

SEQ ID NO: 36              moltype = AA  length = 107
FEATURE                    Location/Qualifiers
source                     1..107
                           mol_type = protein
                           organism = synthetic construct
SEQUENCE: 36
DIQMTQSPSS LSASVGDRVT ITCRTSENIY NNLAWYQQKP GKAPKLLIYA ATNLAEGVPS    60
RFSGSGSGTD YTLTISSLQP EDFATYYCQH FWGTPLTFGG GTKVEIK                 107

SEQ ID NO: 37              moltype = AA  length = 107
FEATURE                    Location/Qualifiers
source                     1..107
                           mol_type = protein
                           organism = synthetic construct
SEQUENCE: 37
DIQMTQSPSS LSASVGDRVT ITCRTSENIY SNLAWYQQKP GKAPKLLIYA GTNLADGVPS    60
RFSGSGSGTD YTLTISSLQP EDFANYYCQH FWGTPLTFGG GTKVEIK                 107

SEQ ID NO: 38              moltype = AA  length = 107
FEATURE                    Location/Qualifiers
source                     1..107
                           mol_type = protein
                           organism = synthetic construct
SEQUENCE: 38
DIQMTQSPAS LSVSVGETVT ITCRTSENIY NNLAWYQQKQ GKSPQLLVYA ATNLADGVPS    60
RFSGSGSGTQ YSLKINSLQS EDFGNYYCQH FWGTPLTFGA GTKLELK                 107

SEQ ID NO: 39              moltype = AA  length = 445
FEATURE                    Location/Qualifiers
source                     1..445
                           mol_type = protein
                           organism = synthetic construct
SEQUENCE: 39
QVQLVQSGAE VKKPGASVKV SCKASGYTFT NYWMHWVRQA PGQGLEWMGE INPINGRSNY    60
AQKFQGRVTL TVDTSISTAY MELSRLRSDD TAVYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 40              moltype = AA  length = 445
FEATURE                    Location/Qualifiers
source                     1..445
                           mol_type = protein
                           organism = synthetic construct
SEQUENCE: 40
QVQLVQSGAE VKKPGASVKV SCKASGYTFT NYWMHWVRQA PGQGLEWMGE INPINGRSNY    60
AQKFQGRVTL TVDTSISTAY MELSRLRSDD TAVYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 41              moltype = AA  length = 445
FEATURE                    Location/Qualifiers
source                     1..445
                           mol_type = protein
                           organism = synthetic construct
SEQUENCE: 41
QVQLVQSGAE VKKPGASVKV SCKASGYTFT NYWMHWVRQA PGQGLEWMGE INPINGRSNY    60
AQKFQGRVTL TVDTSISTAY MELSRLRSDD TAVYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC GVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 42              moltype = AA  length = 445
FEATURE                    Location/Qualifiers
source                     1..445
                           mol_type = protein
```

```
SEQUENCE: 42
QVQLVQSGAE VKKPGASVKV SCKASGYTFT NYWMHWVRQA PGQGLEWMGE INPINGRSNY      60
AQKFQGRVTL TVDTSISTAY MELSRLRSDD TAVYYCARGT RAMHYWGQGT LVTVSSASTK     120
GPSVFPLAPS SKSTSGGTAA LGCLVKDYFP EPVTVSWNSG ALTSGVHTFP AVLQSSGLYS     180
LSSVVTVPSS SLGTQTYICN VNHKPSNTKV DKRVEPKSCD KTHTCPPCPA PEAAGGPSVF     240
LFPPKPKDTL MISRTPEVTC VVVDVSHEDP EVKFNWYVDG VEVHNAKTKP REEQYNSTYR     300
VVSVLTVLHQ DWLNGKEYKC KVSNKARPAP IEKTISKAKG QPREPQVYTL PPSREEMTKN     360
QVSLTCLVKG FYPSDIAVEW ESNGQPENNY KTTPPVLDSD GSFFLYSKLT VDKSRWQQGN     420
VFSCSVMHEA LHNHYTQKSL SLSPG                                          445

SEQ ID NO: 43           moltype = AA  length = 445
FEATURE                 Location/Qualifiers
source                  1..445
                        mol_type = protein
                        organism = synthetic construct
SEQUENCE: 43
QVQLVQSGAE VKKPGASVKV SCKASGYTFT NYWMHWVRQA PGQGLEWMGE INPINGRSNY      60
AQKFQGRVTL TVDTSISTAY MELSRLRSDD TAVYYCARGT RAMHYWGQGT LVTVSSASTK     120
GPSVFPLAPS SKSTSGGTAA LGCLVKDYFP EPVTVSWNSG ALTSGVHTFP AVLQSSGLYS     180
LSSVVTVPSS SLGTQTYICN VNHKPSNTKV DKRVEPKSCD KTHTCPPCPA PEAAGGPSVF     240
LFPPKPKDTL MISRTPEVTC VVVDVSHEDP EVKFNWYVDG VEVHNAKTKP REEQYNSTYR     300
VVSVLTVLHQ DWLNGKEYKC KVSNKALGAP IEKTISKAKG QPREPQVYTL PPSREEMTKN     360
QVSLTCLVKG FYPSDIAVEW ESNGQPENNY KTTPPVLDSD GSFFLYSKLT VDKSRWQQGN     420
VFSCSVMHEA LHNHYTQKSL SLSPG                                          445

SEQ ID NO: 44           moltype = AA  length = 445
FEATURE                 Location/Qualifiers
source                  1..445
                        mol_type = protein
                        organism = synthetic construct
SEQUENCE: 44
QVQLVQSGAE VKKPGASVKV SCKASGYTFT NYWMHWVRQA PGQGLEWMGE INPINGRSNY      60
AQKFQGRVTL TVDTSISTAY MELSRLRSDD TAVYYCARGT RAMHYWGQGT LVTVSSASTK     120
GPSVFPLAPS SKSTSGGTAA LGCLVKDYFP EPVTVSWNSG ALTSGVHTFP AVLQSSGLYS     180
LSSVVTVPSS SLGTQTYICN VNHKPSNTKV DKRVEPKSCD KTHTCPPCPA PELLGGPSVF     240
LFPPKPKDTL MISRTPEVTC VVVAVSHEDP EVKFNWYVDG VEVHNAKTKP REEQYGSTYR     300
VVSVLTVLHQ DWLNGKEYKC KVSNKALPAP IEKTISKAKG QPREPQVYTL PPSREEMTKN     360
QVSLTCLVKG FYPSDIAVEW ESNGQPENNY KTTPPVLDSD GSFFLYSKLT VDKSRWQQGN     420
VFSCSVMHEA LHNHYTQKSL SLSPG                                          445

SEQ ID NO: 45           moltype = AA  length = 445
FEATURE                 Location/Qualifiers
source                  1..445
                        mol_type = protein
                        organism = synthetic construct
SEQUENCE: 45
QVQLVQSGAE VKKPGASVKV SCKASGYTFT NYWMHWVRQA PGQGLEWIGE INPINGRSNY      60
AEKFQGRVTL TVDTSSSTAY MELSRLRSDD TAVYYCARGT RAMHYWGQGT LVTVSSASTK     120
GPSVFPLAPS SKSTSGGTAA LGCLVKDYFP EPVTVSWNSG ALTSGVHTFP AVLQSSGLYS     180
LSSVVTVPSS SLGTQTYICN VNHKPSNTKV DKRVEPKSCD KTHTCPPCPA PELLGGPSVF     240
LFPPKPKDTL MISRTPEVTC VVVDVSHEDP EVKFNWYVDG VEVHNAKTKP REEQYNSTYR     300
VVSVLTVLHQ DWLNGKEYKC KVSNKALPAP IEKTISKAKG QPREPQVYTL PPSREEMTKN     360
QVSLTCLVKG FYPSDIAVEW ESNGQPENNY KTTPPVLDSD GSFFLYSKLT VDKSRWQQGN     420
VFSCSVMHEA LHNHYTQKSL SLSPG                                          445

SEQ ID NO: 46           moltype = AA  length = 445
FEATURE                 Location/Qualifiers
source                  1..445
                        mol_type = protein
                        organism = synthetic construct
SEQUENCE: 46
QVQLVQSGAE VKKPGASVKV SCKASGYTFT NYWMHWVRQA PGQGLEWIGE INPINGRSNY      60
AEKFQGRVTL TVDTSSSTAY MELSRLRSDD TAVYYCARGT RAMHYWGQGT LVTVSSASTK     120
GPSVFPLAPS SKSTSGGTAA LGCLVKDYFP EPVTVSWNSG ALTSGVHTFP AVLQSSGLYS     180
LSSVVTVPSS SLGTQTYICN VNHKPSNTKV DKRVEPKSCD KTHTCPPCPA PEAAGGPSVF     240
LFPPKPKDTL MISRTPEVTC VVVDVSHEDP EVKFNWYVDG VEVHNAKTKP REEQYNSTYR     300
VVSVLTVLHQ DWLNGKEYKC KVSNKALPAP IEKTISKAKG QPREPQVYTL PPSREEMTKN     360
QVSLTCLVKG FYPSDIAVEW ESNGQPENNY KTTPPVLDSD GSFFLYSKLT VDKSRWQQGN     420
VFSCSVMHEA LHNHYTQKSL SLSPG                                          445

SEQ ID NO: 47           moltype = AA  length = 445
FEATURE                 Location/Qualifiers
source                  1..445
                        mol_type = protein
                        organism = synthetic construct
SEQUENCE: 47
QVQLVQSGAE VKKPGASVKV SCKASGYTFT NYWMHWVRQA PGQGLEWIGE INPINGRSNY      60
AEKFQGRVTL TVDTSSSTAY MELSRLRSDD TAVYYCARGT RAMHYWGQGT LVTVSSASTK     120
```

```
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC GVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 48           moltype = AA  length = 445
FEATURE                 Location/Qualifiers
source                  1..445
                        mol_type = protein
                        organism = synthetic construct
SEQUENCE: 48
QVQLVQSGAE VKKPGASVKV SCKASGYTFT NYWMHWVRQA PGQGLEWIGE INPINGRSNY    60
AEKFQGRVTL TVDTSSSTAY MELSRLRSDD TAVYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKARPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 49           moltype = AA  length = 445
FEATURE                 Location/Qualifiers
source                  1..445
                        mol_type = protein
                        organism = synthetic construct
SEQUENCE: 49
QVQLVQSGAE VKKPGASVKV SCKASGYTFT NYWMHWVRQA PGQGLEWIGE INPINGRSNY    60
AEKFQGRVTL TVDTSSSTAY MELSRLRSDD TAVYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALGAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 50           moltype = AA  length = 445
FEATURE                 Location/Qualifiers
source                  1..445
                        mol_type = protein
                        organism = synthetic construct
SEQUENCE: 50
QVQLVQSGAE VKKPGASVKV SCKASGYTFT NYWMHWVRQA PGQGLEWIGE INPINGRSNY    60
AEKFQGRVTL TVDTSSSTAY MELSRLRSDD TAVYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PELLGGPSVF   240
LFPPKPKDTL MISRTPEVTC VVVAVSHEDP EVKFNWYVDG VEVHNAKTKP REEQYGSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 51           moltype = AA  length = 445
FEATURE                 Location/Qualifiers
source                  1..445
                        mol_type = protein
                        organism = synthetic construct
SEQUENCE: 51
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 52           moltype = AA  length = 445
FEATURE                 Location/Qualifiers
source                  1..445
                        mol_type = protein
                        organism = synthetic construct
SEQUENCE: 52
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
```

-continued

```
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 53            moltype = AA  length = 445
FEATURE                  Location/Qualifiers
source                   1..445
                         mol_type = protein
                         organism = synthetic construct
SEQUENCE: 53
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC GVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 54            moltype = AA  length = 445
FEATURE                  Location/Qualifiers
source                   1..445
                         mol_type = protein
                         organism = synthetic construct
SEQUENCE: 54
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKARPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 55            moltype = AA  length = 445
FEATURE                  Location/Qualifiers
source                   1..445
                         mol_type = protein
                         organism = synthetic construct
SEQUENCE: 55
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALGAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 56            moltype = AA  length = 445
FEATURE                  Location/Qualifiers
source                   1..445
                         mol_type = protein
                         organism = synthetic construct
SEQUENCE: 56
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PELLGGPSVF    240
LFPPKPKDTL MISRTPEVTC VVVAVSHEDP EVKFNWYVDG VEVHNAKTKP REEQYGSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 57            moltype = AA  length = 445
FEATURE                  Location/Qualifiers
source                   1..445
                         mol_type = protein
                         organism = synthetic construct
SEQUENCE: 57
QVQLVQSGAE VKKPGASVKV SCKASGYTFT NYWMHWVRQA PGQGLEWMGE INPINGRSNY    60
AEKFQGRVTL TVDTSSSTAY MELSSLRSED TATYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 58            moltype = AA  length = 445
```

```
FEATURE                 Location/Qualifiers
source                  1..445
                        mol_type = protein
                        organism = synthetic construct
SEQUENCE: 58
QVQLVQSGAE VKKPGASVKV SCKASGYTFT NYWMHWVRQA PGQGLEWMGE INPINGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 59           moltype = AA  length = 445
FEATURE                 Location/Qualifiers
source                  1..445
                        mol_type = protein
                        organism = synthetic construct
SEQUENCE: 59
QVQLVQSGAE VKKPGASVKV SCKASGYTFT NYWMHWVRQA PGQGLEWMGE INPINGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC GVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 60           moltype = AA  length = 445
FEATURE                 Location/Qualifiers
source                  1..445
                        mol_type = protein
                        organism = synthetic construct
SEQUENCE: 60
QVQLVQSGAE VKKPGASVKV SCKASGYTFT NYWMHWVRQA PGQGLEWMGE INPINGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKARPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 61           moltype = AA  length = 445
FEATURE                 Location/Qualifiers
source                  1..445
                        mol_type = protein
                        organism = synthetic construct
SEQUENCE: 61
QVQLVQSGAE VKKPGASVKV SCKASGYTFT NYWMHWVRQA PGQGLEWMGE INPINGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALGAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 62           moltype = AA  length = 445
FEATURE                 Location/Qualifiers
source                  1..445
                        mol_type = protein
                        organism = synthetic construct
SEQUENCE: 62
QVQLVQSGAE VKKPGASVKV SCKASGYTFT NYWMHWVRQA PGQGLEWMGE INPINGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PELLGGPSVF   240
LFPPKPKDTL MISRTPEVTC VVVAVSHEDP EVKFNWYVDG VEVHNAKTKP REEQYGSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 63           moltype = AA  length = 214
FEATURE                 Location/Qualifiers
source                  1..214
                        mol_type = protein
                        organism = synthetic construct
```

```
SEQUENCE: 63
DIQMTQSPSS LSASVGDRVT ITCRTSENIY NNLAWYQQKP GKSPKLLIYA ATNLADGVPS    60
RFSGSGSGTD YTLTISSLQP EDFATYYCQH FWGTPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 64           moltype = AA  length = 214
FEATURE                 Location/Qualifiers
source                  1..214
                        mol_type = protein
                        organism = synthetic construct
SEQUENCE: 64
DIQMTQSPSS LSASVGDRVT ITCRTSENIY NNLAWYQQKP GKAPKLLIYA ATNLADGVPS    60
RFSGSGSGTD YTLTISSLQP EDFATYYCQH FWGTPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 65           moltype = AA  length = 214
FEATURE                 Location/Qualifiers
source                  1..214
                        mol_type = protein
                        organism = synthetic construct
SEQUENCE: 65
DIQMTQSPSS LSASVGDRVT ITCRTSENIY NNLAWYQQKP GKAPKLLIYA ATNLAEGVPS    60
RFSGSGSGTD YTLTISSLQP EDFATYYCQH FWGTPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 66           moltype = AA  length = 214
FEATURE                 Location/Qualifiers
source                  1..214
                        mol_type = protein
                        organism = synthetic construct
SEQUENCE: 66
DIQMTQSPSS LSASVGDRVT ITCRTSENIY SNLAWYQQKP GKAPKLLIYA GTNLADGVPS    60
RFSGSGSGTD YTLTISSLQP EDFANYYCQH FWGTPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 67           moltype =     length =
SEQUENCE: 67
000

SEQ ID NO: 68           moltype =     length =
SEQUENCE: 68
000

SEQ ID NO: 69           moltype =     length =
SEQUENCE: 69
000

SEQ ID NO: 70           moltype =     length =
SEQUENCE: 70
000

SEQ ID NO: 71           moltype =     length =
SEQUENCE: 71
000

SEQ ID NO: 72           moltype =     length =
SEQUENCE: 72
000

SEQ ID NO: 73           moltype =     length =
SEQUENCE: 73
000

SEQ ID NO: 74           moltype =     length =
SEQUENCE: 74
000

SEQ ID NO: 75           moltype =     length =
SEQUENCE: 75
000

SEQ ID NO: 76           moltype =     length =
SEQUENCE: 76
000
```

-continued

| | | |
|---|---|---|
| SEQ ID NO: 77<br>SEQUENCE: 77<br>000 | moltype = | length = |
| SEQ ID NO: 78<br>SEQUENCE: 78<br>000 | moltype = | length = |
| SEQ ID NO: 79<br>SEQUENCE: 79<br>000 | moltype = | length = |
| SEQ ID NO: 80<br>SEQUENCE: 80<br>000 | moltype = | length = |
| SEQ ID NO: 81<br>SEQUENCE: 81<br>000 | moltype = | length = |
| SEQ ID NO: 82<br>SEQUENCE: 82<br>000 | moltype = | length = |
| SEQ ID NO: 83<br>SEQUENCE: 83<br>000 | moltype = | length = |
| SEQ ID NO: 84<br>SEQUENCE: 84<br>000 | moltype = | length = |
| SEQ ID NO: 85<br>SEQUENCE: 85<br>000 | moltype = | length = |
| SEQ ID NO: 86<br>SEQUENCE: 86<br>000 | moltype = | length = |
| SEQ ID NO: 87<br>SEQUENCE: 87<br>000 | moltype = | length = |
| SEQ ID NO: 88<br>SEQUENCE: 88<br>000 | moltype = | length = |
| SEQ ID NO: 89<br>SEQUENCE: 89<br>000 | moltype = | length = |

SEQ ID NO: 90          moltype = DNA   length = 20
FEATURE                Location/Qualifiers
source                 1..20
                       mol_type = other DNA
                       organism = synthetic construct
SEQUENCE: 90
ctgtggaaag ggtgaagcta                                           20

SEQ ID NO: 91          moltype = DNA   length = 20
FEATURE                Location/Qualifiers
source                 1..20
                       mol_type = other DNA
                       organism = synthetic construct
SEQUENCE: 91
gacaagggaa ctccaggatg                                           20

SEQ ID NO: 92          moltype = DNA   length = 24
FEATURE                Location/Qualifiers
source                 1..24
                       mol_type = other DNA
                       organism = synthetic construct
SEQUENCE: 92
agctctctcc cagcttgatt tcca                                      24

SEQ ID NO: 93          moltype = DNA   length = 19
FEATURE                Location/Qualifiers
source                 1..19

```
                        mol_type = other DNA
                        organism = synthetic construct
SEQUENCE: 93
aaggaccgac aagggaact                                            19

SEQ ID NO: 94           moltype = DNA   length = 23
FEATURE                 Location/Qualifiers
source                  1..23
                        mol_type = other DNA
                        organism = synthetic construct
SEQUENCE: 94
ttctgacaac agtttgccgc tgc                                       23

SEQ ID NO: 95           moltype = DNA   length = 24
FEATURE                 Location/Qualifiers
source                  1..24
                        mol_type = other DNA
                        organism = synthetic construct
SEQUENCE: 95
gctgaattat ttcttccgca gttg                                      24

SEQ ID NO: 96           moltype = AA   length = 4
FEATURE                 Location/Qualifiers
source                  1..4
                        mol_type = protein
                        organism = synthetic construct
SEQUENCE: 96
GGFG                                                            4

SEQ ID NO: 97           moltype = AA   length = 4
FEATURE                 Location/Qualifiers
source                  1..4
                        mol_type = protein
                        organism = synthetic construct
SEQUENCE: 97
ALAL                                                            4

SEQ ID NO: 98           moltype = AA   length = 4
FEATURE                 Location/Qualifiers
source                  1..4
                        mol_type = protein
                        organism = synthetic construct
SEQUENCE: 98
GFLG                                                            4

SEQ ID NO: 99           moltype =    length =
SEQUENCE: 99
000

SEQ ID NO: 100          moltype = DNA   length = 30
FEATURE                 Location/Qualifiers
source                  1..30
                        mol_type = other DNA
                        organism = synthetic construct
SEQUENCE: 100
cgccatttct caacagatct gtcaaatcgc                                30

SEQ ID NO: 101          moltype = DNA   length = 30
FEATURE                 Location/Qualifiers
source                  1..30
                        mol_type = other DNA
                        organism = synthetic construct
SEQUENCE: 101
ccgccatttc tcaacagatc tgtcaaatcg                                30

SEQ ID NO: 102          moltype = DNA   length = 30
FEATURE                 Location/Qualifiers
source                  1..30
                        mol_type = other DNA
                        organism = synthetic construct
SEQUENCE: 102
gccgccattt ctcaacagat ctgtcaaatc                                30

SEQ ID NO: 103          moltype = DNA   length = 30
FEATURE                 Location/Qualifiers
source                  1..30
                        mol_type = other DNA
                        organism = synthetic construct
SEQUENCE: 103
```
agccgccatt tctcaacaga tctgtcaaat                                         30

SEQ ID NO: 104          moltype = DNA   length = 30
FEATURE                 Location/Qualifiers
source                  1..30
                        mol_type = other DNA
                        organism = synthetic construct
SEQUENCE: 104
aagccgccat ttctcaacag atctgtcaaa                                         30

SEQ ID NO: 105          moltype = DNA   length = 30
FEATURE                 Location/Qualifiers
source                  1..30
                        mol_type = other DNA
                        organism = synthetic construct
SEQUENCE: 105
aaagccgcca tttctcaaca gatctgtcaa                                         30

SEQ ID NO: 106          moltype = DNA   length = 30
FEATURE                 Location/Qualifiers
source                  1..30
                        mol_type = other DNA
                        organism = synthetic construct
SEQUENCE: 106
aaaagccgcc atttctcaac agatctgtca                                         30

SEQ ID NO: 107          moltype = DNA   length = 30
FEATURE                 Location/Qualifiers
source                  1..30
                        mol_type = other DNA
                        organism = synthetic construct
SEQUENCE: 107
aaaacgccgc catttctcaa cagatctgtc                                         30

SEQ ID NO: 108          moltype = DNA   length = 30
FEATURE                 Location/Qualifiers
source                  1..30
                        mol_type = other DNA
                        organism = synthetic construct
SEQUENCE: 108
gaaaacgccg ccatttctca acagatctgt                                         30

SEQ ID NO: 109          moltype = DNA   length = 30
FEATURE                 Location/Qualifiers
source                  1..30
                        mol_type = other DNA
                        organism = synthetic construct
SEQUENCE: 109
tgaaaacgcc gccatttctc aacagatctg                                         30

SEQ ID NO: 110          moltype = DNA   length = 30
FEATURE                 Location/Qualifiers
source                  1..30
                        mol_type = other DNA
                        organism = synthetic construct
SEQUENCE: 110
atgaaaacgc cgccatttct caacagatct                                         30

SEQ ID NO: 111          moltype = DNA   length = 30
FEATURE                 Location/Qualifiers
source                  1..30
                        mol_type = other DNA
                        organism = synthetic construct
SEQUENCE: 111
cataatgaaa acgccgccat ttctcaacag                                         30

SEQ ID NO: 112          moltype = DNA   length = 25
FEATURE                 Location/Qualifiers
source                  1..25
                        mol_type = other DNA
                        organism = synthetic construct
SEQUENCE: 112
catttctcaa cagatctgtc aaatc                                              25

SEQ ID NO: 113          moltype = DNA   length = 25
FEATURE                 Location/Qualifiers
source                  1..25
                        mol_type = other DNA
                        organism = synthetic construct -continued

```
SEQUENCE: 113
gccatttctc aacagatctg tcaaa                                              25

SEQ ID NO: 114         moltype = DNA   length = 25
FEATURE                Location/Qualifiers
source                 1..25
                       mol_type = other DNA
                       organism = synthetic construct
SEQUENCE: 114
cgccatttct caacagatct gtcaa                                              25

SEQ ID NO: 115         moltype = DNA   length = 25
FEATURE                Location/Qualifiers
source                 1..25
                       mol_type = other DNA
                       organism = synthetic construct
SEQUENCE: 115
gccgccattt ctcaacagat ctgtc                                              25

SEQ ID NO: 116         moltype = DNA   length = 26
FEATURE                Location/Qualifiers
source                 1..26
                       mol_type = other DNA
                       organism = synthetic construct
SEQUENCE: 116
cgccatttct caacagatct gtcaaa                                             26

SEQ ID NO: 117         moltype = DNA   length = 26
FEATURE                Location/Qualifiers
source                 1..26
                       mol_type = other DNA
                       organism = synthetic construct
SEQUENCE: 117
ccgccatttc tcaacagatc tgtcaa                                             26

SEQ ID NO: 118         moltype = DNA   length = 26
FEATURE                Location/Qualifiers
source                 1..26
                       mol_type = other DNA
                       organism = synthetic construct
SEQUENCE: 118
cgccgccatt tctcaacaga tctgtc                                             26

SEQ ID NO: 119         moltype = DNA   length = 26
FEATURE                Location/Qualifiers
source                 1..26
                       mol_type = other DNA
                       organism = synthetic construct
SEQUENCE: 119
acgccgccat ttctcaacag atctgt                                             26

SEQ ID NO: 120         moltype = DNA   length = 27
FEATURE                Location/Qualifiers
source                 1..27
                       mol_type = other DNA
                       organism = synthetic construct
SEQUENCE: 120
ccgccatttc tcaacagatc tgtcaaa                                            27

SEQ ID NO: 121         moltype = DNA   length = 27
FEATURE                Location/Qualifiers
source                 1..27
                       mol_type = other DNA
                       organism = synthetic construct
SEQUENCE: 121
gccgccattt ctcaacagat ctgtcaa                                            27

SEQ ID NO: 122         moltype = DNA   length = 27
FEATURE                Location/Qualifiers
source                 1..27
                       mol_type = other DNA
                       organism = synthetic construct
SEQUENCE: 122
cgccgccatt tctcaacaga tctgtca                                            27

SEQ ID NO: 123         moltype = DNA   length = 27
FEATURE                Location/Qualifiers
source                 1..27
                       mol_type = other DNA
```

```
                        organism = synthetic construct
SEQUENCE: 123
acgccgccat ttctcaacag atctgtc                                               27

SEQ ID NO: 124          moltype = DNA  length = 28
FEATURE                 Location/Qualifiers
source                  1..28
                        mol_type = other DNA
                        organism = synthetic construct
SEQUENCE: 124
cgccatttct caacagatct gtcaaatc                                              28

SEQ ID NO: 125          moltype = DNA  length = 28
FEATURE                 Location/Qualifiers
source                  1..28
                        mol_type = other DNA
                        organism = synthetic construct
SEQUENCE: 125
ccgccatttc tcaacagatc tgtcaaat                                              28

SEQ ID NO: 126          moltype = DNA  length = 28
FEATURE                 Location/Qualifiers
source                  1..28
                        mol_type = other DNA
                        organism = synthetic construct
SEQUENCE: 126
gccgccattt ctcaacagat ctgtcaaa                                              28

SEQ ID NO: 127          moltype = DNA  length = 28
FEATURE                 Location/Qualifiers
source                  1..28
                        mol_type = other DNA
                        organism = synthetic construct
SEQUENCE: 127
cgccgccatt tctcaacaga tctgtcaa                                              28

SEQ ID NO: 128          moltype = DNA  length = 28
FEATURE                 Location/Qualifiers
source                  1..28
                        mol_type = other DNA
                        organism = synthetic construct
SEQUENCE: 128
acgccgccat ttctcaacag atctgtca                                              28

SEQ ID NO: 129          moltype = DNA  length = 28
FEATURE                 Location/Qualifiers
source                  1..28
                        mol_type = other DNA
                        organism = synthetic construct
SEQUENCE: 129
aacgccgcca tttctcaaca gatctgtc                                              28

SEQ ID NO: 130          moltype = DNA  length = 28
FEATURE                 Location/Qualifiers
source                  1..28
                        mol_type = other DNA
                        organism = synthetic construct
SEQUENCE: 130
ctttatatca taatgaaaac gccgccat                                              28

SEQ ID NO: 131          moltype = DNA  length = 28
FEATURE                 Location/Qualifiers
source                  1..28
                        mol_type = other DNA
                        organism = synthetic construct
SEQUENCE: 131
tctttatatc ataatgaaaa cgccgcca                                              28

SEQ ID NO: 132          moltype = DNA  length = 28
FEATURE                 Location/Qualifiers
source                  1..28
                        mol_type = other DNA
                        organism = synthetic construct
SEQUENCE: 132
atctttatat cataatgaaa acgccgcc                                              28

SEQ ID NO: 133          moltype = DNA  length = 25
FEATURE                 Location/Qualifiers
source                  1..25
```

-continued

```
                        mol_type = other DNA
                        organism = synthetic construct
SEQUENCE: 133
gccgccattt ctcaacagat ctgtc                                      25

SEQ ID NO: 134          moltype = RNA   length = 148
FEATURE                 Location/Qualifiers
source                  1..148
                        mol_type = mRNA
                        organism = Homo sapiens
SEQUENCE: 134
gcgatttgac agatctgttg agaaatggcg gcgttttcat tatgatataa agatatttaa    60
tcagtggcta acagaagctg aacagtttct cagaaagaca caaattcctg agaattggga   120
acatgctaaa tacaaatggt atcttaag                                     148
```